(12) United States Patent
Maeshima et al.

(10) Patent No.: US 9,988,499 B2
(45) Date of Patent: Jun. 5, 2018

(54) METHOD FOR PRODUCING LIQUID HIGH-PURITY SUGAR DERIVATIVE-MODIFIED SILICONE OR COMPOSITION THEREOF

(71) Applicant: Dow Corning Toray Co., Ltd., Tokyo (JP)

(72) Inventors: Hideko Maeshima, Chiba (JP); Sayuri Sawayama, Chiba (JP); Tatsuo Souda, Chiba (JP); Seiki Tamura, Chiba (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 0 days. days.

(21) Appl. No.: 15/310,250

(22) PCT Filed: Apr. 20, 2015

(86) PCT No.: PCT/JP2015/002151
§ 371 (c)(1),
(2) Date: Dec. 25, 2016

(87) PCT Pub. No.: WO2015/162904
PCT Pub. Date: Oct. 29, 2015

(65) Prior Publication Data
US 2017/0218129 A1    Aug. 3, 2017

(30) Foreign Application Priority Data
Apr. 21, 2014 (JP) .................................. 2014-087711

(51) Int. Cl.
| | | |
|---|---|---|
| C07F 7/00 | (2006.01) | |
| C08G 77/34 | (2006.01) | |
| C08G 77/38 | (2006.01) | |
| A61K 8/892 | (2006.01) | |
| A61Q 19/00 | (2006.01) | |
| A61Q 17/04 | (2006.01) | |
| A61Q 1/02 | (2006.01) | |
| B01J 20/14 | (2006.01) | |
| B01D 15/00 | (2006.01) | |
| B01D 29/01 | (2006.01) | |
| C08G 77/00 | (2006.01) | |

(52) U.S. Cl.
CPC .............. *C08G 77/34* (2013.01); *A61K 8/892* (2013.01); *A61Q 1/02* (2013.01); *A61Q 17/04* (2013.01); *A61Q 19/00* (2013.01); *B01D 15/00* (2013.01); *B01D 29/016* (2013.01); *B01J 20/14* (2013.01); *C08G 77/38* (2013.01); *A61K 2800/10* (2013.01); *C08G 77/70* (2013.01)

(58) Field of Classification Search
CPC ........ C08G 77/34; C08G 77/38; A61K 8/892; A61Q 1/02; A61Q 17/04; A61Q 19/00; B01D 15/00; B01D 29/016; B01J 20/14

USPC .......................................................... 556/434
See application file for complete search history.

(56) References Cited

U.S. PATENT DOCUMENTS

| | | |
|---|---|---|
| 5,583,244 A | 12/1996 | Uchida et al. |
| 5,747,016 A | 5/1998 | Yui et al. |
| 5,831,080 A | 11/1998 | Sejpka et al. |
| 5,891,977 A | 4/1999 | Dietz et al. |
| 6,066,727 A | 5/2000 | Yamamoto et al. |
| 6,218,560 B1 | 4/2001 | Abele et al. |
| 6,307,000 B1 | 10/2001 | Wong |
| 2004/0146472 A1 | 7/2004 | Nakanishi |
| 2005/0043365 A1 | 2/2005 | Yoshitake et al. |
| 2006/0183877 A1 | 8/2006 | Yoshitake et al. |
| 2008/0200612 A1 | 8/2008 | Joffre et al. |
| 2010/0113731 A1 | 5/2010 | Hayashi et al. |
| 2013/0102686 A1 | 4/2013 | Tamura et al. |
| 2013/0177516 A1* | 7/2013 | Tamura ................. A61K 8/894 424/70.12 |
| 2013/0210930 A1 | 8/2013 | Souda et al. |
| 2014/0187649 A1 | 7/2014 | Tamura et al. |
| 2014/0371330 A1 | 12/2014 | Hayashi et al. |

(Continued)

FOREIGN PATENT DOCUMENTS

| | | |
|---|---|---|
| EP | 0523738 A1 | 1/1993 |
| JP | S57209295 A | 12/1982 |
| JP | S6268820 A | 3/1987 |

(Continued)

OTHER PUBLICATIONS

PCT/JP2015/002151 International Search Report dated Jun. 23, 2015, 2 pages.

English language abstract and machine translation for JPS57209295(A) extracted from https://www.j-platpat.inpit.go.jp and from http://worldwide.espacenet.com database on Feb. 10, 2017, 7 pages.

(Continued)

*Primary Examiner* — Sudhakar Katakam
*Assistant Examiner* — Kofi Adzamli
(74) *Attorney, Agent, or Firm* — Warner Norcross & Judd LLP

(57) ABSTRACT

A production method for a liquid high purity sugar derivative-modified silicone or a composition thereof is disclosed. The method comprises the steps of: 1) capturing hydrophilic impurities in solid particles by causing an impurity containing composition containing liquid sugar derivative-modified silicone and the hydrophilic impurities derived from a sugar derivative to contact the solid particles, the sugar derivative being a hydrophilic modifier of the sugar derivative-modified silicone, and the solid particles being able to capture the hydrophilic impurities; and 2) separating the sugar derivative-modified silicone and the solid particles. The method is useful for production of the liquid high purity sugar derivative-modified silicone and the composition thereof on a commercial scale.

13 Claims, No Drawings

(56) References Cited

U.S. PATENT DOCUMENTS

| | | | |
|---|---|---|---|
| 2015/0011656 A1 | 1/2015 | Tamura et al. | |
| 2015/0080480 A1 | 5/2015 | Tamura et al. | |

FOREIGN PATENT DOCUMENTS

| | | |
|---|---|---|
| JP | H05186596 A | 7/1993 |
| JP | H06145201 A | 5/1994 |
| JP | H06316590 A | 11/1994 |
| JP | H07133352 A | 5/1995 |
| JP | H08134103 A | 5/1996 |
| JP | H08269204 A | 10/1996 |
| JP | H08283302 A | 10/1996 |
| JP | H08283304 A | 10/1996 |
| JP | H10259186 A | 9/1998 |
| JP | 10330489 A | 12/1998 |
| JP | H1192490 A | 4/1999 |
| JP | 11349601 A | 12/1999 |
| JP | 2000186150 A | 7/2000 |
| JP | 2001240605 A | 9/2001 |
| JP | 2002119840 A | 4/2002 |
| JP | 2002179798 A | 6/2002 |
| JP | 2003503520 A | 1/2003 |
| JP | 2003146991 A | 5/2003 |
| JP | 2003147082 A | 5/2003 |
| JP | 2008179578 A | 8/2008 |
| JP | 2008274241 A | 11/2008 |
| JP | 2008542474 A | 11/2008 |
| JP | 2011246705 A | 12/2011 |
| JP | 2011246706 A | 12/2011 |
| JP | 201246508 A | 3/2012 |
| JP | 2012246445 A | 12/2012 |
| JP | 2012246446 A | 12/2012 |
| JP | 2013151657 A | 8/2013 |
| JP | 2013151658 A | 8/2013 |
| JP | 2013151659 A | 8/2013 |
| WO | WO2011136394 A1 | 11/2011 |

OTHER PUBLICATIONS

English language abstract and machine translation for JPS6268820(A) extracted from https://www.j-platpat.inpit.go.jp database on Feb. 10, 2017, 5 pages.

English language abstract and machine translation for JPH05186596(A) extracted from http://worldwide.espacenet.com database on Nov. 22, 2016, 27 pages.

English language abstract and machine translation for JPH06145201(A) extracted from http://worldwide.espacenet.com database on Nov. 22, 2016, 12 pages.

English language abstract and machine translation for JPH08283302(A) extracted from http://worldwide.espacenet.com database on Nov. 22, 2016, 12 pages.

English language abstract and machine translation for JPH08269204(A) extracted from http://worldwide.espacenet.com database on Nov. 22, 2016, 16 pages.

English language abstract and machine translation for JPH10259186(A) extracted from http://worldwide.espacenet.com database on Nov. 22, 2016, 25 pages.

English language abstract and machine translation for JPH1192490(A) extracted from http://worldwide.espacenet.com database on Nov. 23, 2016, 33 pages.

English language abstract and machine translation for JP2001240605(A) extracted from http://worldwide.espacenet.com database on Nov. 22, 2016, 12 pages.

English language abstract and machine translation for JP2002119840(A) extracted from http://worldwide.espacenet.com database on Nov. 23, 2016, 14 pages.

English language abstract and machine translation for JP2008179578(A) extracted from http://worldwide.espacenet.com database on Nov. 23, 2016, 9 pages.

English language abstract and machine translation for JP2012246445(A) extracted from http://worldwide.espacenet.com database on Nov. 23, 2016, 129 pages.

* cited by examiner

METHOD FOR PRODUCING LIQUID HIGH-PURITY SUGAR DERIVATIVE-MODIFIED SILICONE OR COMPOSITION THEREOF

CROSS-REFERENCE TO RELATED APPLICATIONS

This application is the National Stage of International Application No. PCT/JP2015/002151 filed on 20 Apr. 2015, which claims priority to and all advantages of Japanese Patent Application No. 2014-087711 filed on 21 Apr. 2014, the content of which is hereby incorporated by reference.

TECHNICAL FIELD

The present invention relates to a production method for liquid high-purity sugar derivative-modified silicone or a composition thereof. The present invention further relates to the use of the liquid high purity sugar derivative-modified silicone and the composition thereof in external use preparations, cosmetic compositions, and various industrial materials.

BACKGROUND ART

As saccharide and silicone compounds, silicone-modified polysaccharides of a type in which polysaccharides are modified by silicone (main skeleton of the molecule is polysaccharide, refer to Patent Documents 1 to 6) and sugar derivative-modified silicones of a type in which a relatively short monosaccharide or oligosaccharide chain is bonded to a silicone chain or a silicone skeleton (main skeleton of the molecule is silicone, refer to Patent Documents 7 to 30) are known.

The former is often a powdery solid and the latter is often a viscous liquid. In general, opacity on the exterior of a powdered product is not a problem, but when a liquid product is cloudy, there may often be a problem of appearance or potential phase separation. Many considerations have been made as described above relating to a chemical structure or the production method of the liquid sugar derivative-modified silicone, but due to the high production difficulty on a commercial scale, there are extremely few commercial products. That is, in general, since there are almost no cases in which an introduction reaction of sugar derivatives with respect to the silicone skeleton proceeds at a chemical equivalent (molar equivalent), normally, the introduction reaction is completed by excessively loading the sugar derivative. Accordingly, an unreacted sugar modifier (sugar derivative) other than a sugar derivative-modified silicone copolymer that is a product remains in a reaction system causing turbidity. Since the sugar derivative has a high boiling point or high molecular weight, purification by stripping is totally ineffective. Therefore, it was extremely difficult to obtain high purity sugar-modified silicones on a commercial scale.

As the production method of the sugar derivative-modified silicone, methods are known in which a sugar derivative having a reactive unsaturated group is added to organohydrogensiloxane (Patent Documents 8 to 10, 13, 17 to 19, and 23 to 28). When molecular weight or weight ratio of silicone moiety in the sugar derivative-modified silicone structure is small, it is easy to obtain a product with little turbidity since the remaining sugar derivative and the sugar derivative-modified silicone are compatible (Patent Documents 10, 18, 19, and 23), but there is a problem in that a range of use is limited since a designable structure is limited. Normally, in many sugar derivative-modified silicones, miscibility of remaining sugar derivatives and sugar derivative-modified silicone products may be low, and the appearance of the product may be cloudy and nonuniform, leading to phase separation during storage after production. Therefore, a purification treatment of removing the remaining sugar derivatives is performed using a technique such as solvent extraction, column chromatography, dialysis, film separation (microfiltration or ultrafiltration), and reprecipitation (Patent Documents 9, 13, and 17 and Comparative Manufacturing Example 6 of Patent Document 30). However, since a large volume of organic solvent or water is necessary for the purification techniques, there is a large problem for waste disposal and efficiency aspects. In addition, there is a problem of limiting the application to a laboratory scale device and not being suitable for mass production on a commercial scale. Microfiltration is one method of filtering fine particles such as colloidal particles that are not able to be filtered using filter paper or the like. There are problems in that since a porous polymer membrane is used, the film tends to be obstructed for a short time at which pore size is small, and that it is necessary to dilute in a large excess of solvent when silicone is generally applied with high viscosity since time is necessary for filtration.

An example is indicated in Patent Document 24 of a compound in which the hydroxyl group is protected is used as the sugar derivative. However, the problem of separation described above is unavoidable even with this technique since deprotection is necessary after the reaction of organohydrogensiloxane ends. A technique for performing deprotection after the protected sugar derivative is introduced to the silicone chain is performing hydrolysis under an environment in which hydrophobicity is increased due to the silicone, and is extremely inefficient. Accordingly, acidizing conditions for deprotection are inevitably harsh and breakage of the silicone backbone occurs. As a result, there is a new problem that the desired product is not obtainable with good reproducibility.

In Example 1 in Patent Document 29, it is reported that xylitol (sugar derivative) co-modified organopolysiloxane that has low viscosity and low HLB is obtained as a transparent liquid by distilling a low boiling point fraction and subjecting to filtration treatment after a hydrosilylation reaction. Since the sugar derivative-modified silicone has extremely low HLB and low viscosity, the affinity between a residual sugar derivative starting material and the produced sugar derivative-modified silicone is extremely poor in a reaction mixture and the residual starting material precipitating due to two layer separation upon leaving to stand for one to two days on a laboratory scale. Therefore, it is possible to obtain good transparency by collecting and filtrating only the phase of a supernatant sugar derivative-modified silicone main body. Accordingly, there are problems of low yield or needing a long time for production and an applicable structure range being narrow. Furthermore, since volume (height) of a reaction mixture is increased in a case of mass production on a commercial scale, there is a problem that a time up to two layer separation is reached is much longer than the laboratory scale and a problem in that an operation in which only the supernatant is filtered is difficult.

As another production method of sugar derivative-modified silicone, techniques are known in which amino-modified silicones are set as a starting material and caused to react (carry out Michael addition) with the sugar derivative containing sugar lactone or an α,β-unsaturated carbonyl group (Patent Documents 7, 11, 12, 16, and 22). However, there is a problem in that an amide bond formed by reaction of an amino group of amino-modified silicone with a sugar lactone is unstable and hydrolysis tends to occur. Since a secondary or tertiary amino group is formed in the reaction of amino-modified silicone and sugar derivatives containing an α,β-unsaturated carbonyl group, there is a concern such as compatibility with formulations thereof and skin irritation.

Patent Document 14 discloses a technique in which epoxy-modified silicone is set as the starting material and reacted with sugar derivatives having the amino groups. Thereby, although stability of hydrolysis is improved, the obtained sugar derivative-modified silicone has a problem in that compounding with a cosmetic product and the like is difficult since coloring is strong and a strong odor of ammonia tends to occur over time. Since the secondary or tertiary amino group is formed, there is a concern such as compatibility with formulations thereof and skin irritation.

Patent Documents 15, 20, and 21 also disclose production methods of special sugar derivative-modified silicone and techniques of purification, but the methods are extremely complex and mass production on a commercial scale is difficult.

As described above, there have been practically no known useful methods for stably producing liquid high-purity sugar derivative-modified silicone or a composition including the same on a commercial scale. Further, there has also been no known technique of increasing purification of liquid sugar derivative-modified silicones which are applicable regardless of the type of sugar modifier and can reasonably accommodate production on a commercial scale. Accordingly, there has been demand for development of a high purity sugar derivative-modified silicone or a composition including the same that is easily produced, and stable as a liquid such that no phase separation or sedimentation of unreacted starting material, or the like occurs after production, and exhibits almost no turbidity, and a method for producing the same.

CITATION LIST

Patent Literature

Patent Document 1: Japanese Unexamined Patent Application Publication No. H06-145201A
Patent Document 2: Japanese Unexamined Patent Application Publication No. H08-283302A
Patent Document 3: Japanese Unexamined Patent Application Publication No. H08-134103A
Patent Document: Japanese Unexamined Patent Application Publication No. H08-283304A
Patent Document 5: Japanese Unexamined Patent Application Publication No. H11-349601A
Patent Document 6: Japanese Unexamined Patent Application Publication No. 2001-240605A
Patent Document 7: Japanese Unexamined Patent Application Publication No. 562-068820A
Patent Document 8: Japanese Unexamined Patent Application Publication No. S62-037039A
Patent Document 9: Japanese Unexamined Patent Application Publication No. H05-186596A
Patent Document 10: Japanese Unexamined Patent Application Publication No. H06-316590A
Patent Document 11: Japanese Unexamined Patent Application Publication No. H07-133352A
Patent Document 12: Japanese Unexamined Patent Application Publication No. H08-269204A
Patent Document 13: Japanese Unexamined Patent Application Publication No. H10-259186A
Patent Document 14: Japanese Unexamined Patent Application Publication No. H10-330489A
Patent Document 15: Japanese Unexamined Patent Application Publication No. H11-092490A
Patent Document 16: Japanese Unexamined Patent Application Publication No. 2000-186150A
Patent Document 17: Japanese Unexamined Patent Application Publication (Translation of PCT Application) No. 2003-503520A
Patent Document 18: Japanese Unexamined Patent Application Publication No. 2002-119840A
Patent Document 19: Japanese Unexamined Patent Application Publication No. 2002-179798A
Patent Document 20: Japanese Unexamined Patent Application Publication No. 2003-147082A
Patent Document 21: Japanese Unexamined Patent Application Publication No. 2003-146991A
Patent Document 22: Japanese Unexamined Patent Application Publication (Translation of PCT Application) No. 2008-542474A
Patent Document 23: Japanese Unexamined Patent Application Publication No. 2008-179578A
Patent Document 24: Japanese Unexamined Patent Application Publication No. 2008-274241A
Patent Document 25: Japanese Unexamined Patent Application Publication No. 2011-246705A
Patent Document 26: Japanese Unexamined Patent Application Publication No. 2011-246706A
Patent Document 27: Japanese Unexamined Patent Application Publication No. 2012-246445A
Patent Document 28: Japanese Unexamined Patent Application Publication No. 2012-246446A
Patent Document 29: Japanese Unexamined Patent Application Publication No. 2013-151657A
Patent Document 30: Japanese Unexamined Patent Application Publication No. 2013-151659A
Patent Document 31: Japanese Unexamined Patent Application Publication No. 2012-046508A

SUMMARY OF INVENTION

Technical Problem

The present invention is carried out in order to solve the problems described above and has the object of providing a production method of a liquid high-purity sugar derivative-modified silicone or a composition thereof useful for production on a commercial scale.

In particular, the present invention has the object of providing a technique for increasing purification of liquid sugar derivative-modified silicones which are applicable regardless of the type of sugar modifier (sugar derivative) and can easily accommodate production on a commercial scale.

Another object of the present invention is to provide liquid high purity sugar derivative-modified silicone or a composition thereof with transparent or translucent appearance since hydrophilic impurities are mostly removed.

In particular, the present invention has the object of providing high purity liquid sugar derivative-modified silicone or a composition thereof in which transparency is high and the transparency is maintained with respect to temperature history and after long term storage, and separation, precipitation, or the like tends not to occur while in the liquid state.

Yet another object of the present invention is to use such liquid high purity sugar derivative-modified silicone or a composition thereof in an external use preparation, cosmetic compositions, or various industrial materials.

Solution to Problem

The object of the present invention is achieved by
a production method for a liquid high purity sugar derivative-modified silicone or a composition thereof, the method including the steps of:

capturing hydrophilic impurities in solid particles by causing an impurity containing composition containing liquid sugar derivative-modified silicone and the hydrophilic impurities derived from a sugar derivative to contact the solid particles, the sugar derivative being a hydrophilic modifier of the sugar derivative-modified silicone, and the solid particles being able to capture the hydrophilic impurities; and separating the sugar derivative-modified silicone and the solid particles.

It is preferable that the solid particles include one or more material selected from a silicon atom-free low molecular organic compound, a silicon atom-free non-crosslinked hydrophilic high molecular organic compound, a silicon atom-free crosslinked hydrophilic high molecular organic compound, a salt, a mineral derived material, and activated carbon.

It is preferable that the solid particles include the silicon atom-free crosslinked hydrophilic high molecular organic compound. It is particularly preferable that the crosslinked hydrophilic high molecular organic compound is one type or more selected from crosslinked polyacrylates such as carboxyvinyl polymers (carbomers) or salts thereof, partially neutralized products, alkyl-modified crosslinked polyacrylates such as alkyl-modified carboxyvinyl polymers (acrylate/C10-30 alkyl acrylate crosspolymers) or salts thereof, partially neutralized products, crosslinked polyacrylamide, a crosslinked poly (2-acrylamido-2-methylpropanesulfonic acid) polymer, and the like.

It is preferable that the solid particles are porous.

It is preferable that the solid particles include silicon dioxide.

It is preferable that the solid particles include at least one type of hydrogen bond forming substance and/or at least one type of ionic bond forming substance and/or a hydrate thereof.

It is preferable that the separating step includes filtering using filtration material (a filter).

It is preferable that the impurity containing compositions are caused to come into contact with the solid particles in the capturing step after dilution using a solvent, that is a good solvent for the sugar derivative-modified silicone and a poor solvent for the hydrophilic impurities. In this case, it is preferable that the production method of the present invention includes heating and/or depressurizing the composition and removing the solvent after the separating step.

The sugar derivative-modified silicone is preferably a sugar derivative-modified silicone represented by the following general formula (1):

[Chemical Formula 1]

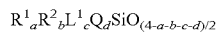

(1)

(wherein, $R^{11}$ represents a monovalent organic group (however, excluding $R^2$, L, and Q), a hydrogen atom or a hydroxyl group, and $R^2$ is a substituted or unsubstituted, straight or branched monovalent hydrocarbon group having from 9 to 60 carbons, or a chain organosiloxane group represented by the following general formula (2-1):

[Chemical Formula 2]

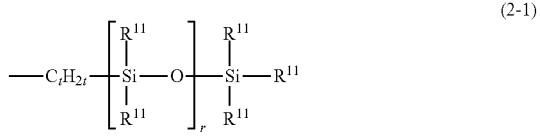

(2-1)

(wherein, $R^{11}$ is independently a substituted or unsubstituted monovalent hydrocarbon group having from 1 to 30 carbons, hydroxyl groups, or hydrogen atoms, and at least one of the $R^{11}$ is the monovalent hydrocarbon group. t is a number in a range of 2 to 10, and r is a number in a range of 1 to 500), or the following general formula (2-2):

[Chemical Formula 3]

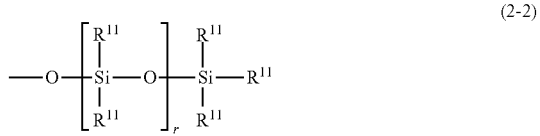

(2-2)

(wherein, $R^{11}$ and r are as described above), and $L^1$ represents a silylalkyl group having a siloxane dendron structure and represented by the following general formula (3) when i=1:

[Chemical Formula 4]

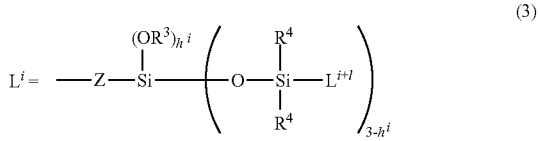

(3)

(wherein, each $R^3$ independently represents a substituted or unsubstituted, straight or branched monovalent hydrocarbon group having from 1 to 30 carbons, each $R^4$ independently represents an alkyl group or phenyl group having from 1 to 6 carbons, Z represents a divalent organic group, i represents a generation of the silylalkyl group represented by $L^i$ and is an integer of 1 to k when k is a number of generations that is a number of repetitions of the silylalkyl group, the number of generations k is an integer from 1 to 10, $L^{i+1}$ is the silylalkyl group when i is less than k, and $R^4$ when i=k, and $h^i$ is a number in a range of 0 to 3), Q represents a sugar derivative group, and a, b, c, and d are numbers respectively in ranges of $1.0 \leq a \leq 2.5$, $0 \leq b \leq 1.5$, $0 \leq c \leq 1.5$, and $0.0001 \leq d \leq 1.5$).

It is preferable that the sugar derivative group is a group derived from monosaccharides, disaccharides, or oligosaccharides.

It is preferable that the sugar derivative group is a sugar alcohol group-containing organic group.

It is preferable that the sugar derivative-modified silicone is modified using a sugar alcohol group-containing organic group represented by the following general formula (4-1):

[Chemical Formula 5]

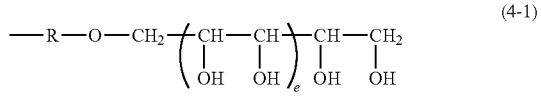
(4-1)

(wherein, R represents a divalent organic group, and e is 1 or 2), or the following general formula (4-2):

[Chemical Formula 6]

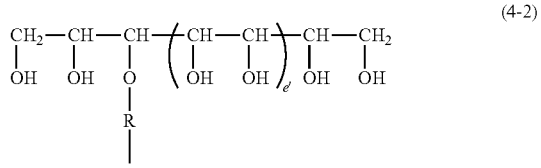
(4-2)

(wherein, R is as described above, and e' is 0 or 1).

The sugar derivative-modified silicone may be a sugar derivative-modified crosslinked silicone.

The present invention also relates to a transparent or translucent liquid high purity sugar derivative-modified silicone or a composition thereof obtained by the production method of the present invention.

The objects of the present invention are also achieved by an external use preparation, a cosmetic composition, or an industrial material containing a transparent or translucent liquid high purity sugar derivative-modified silicone or a composition thereof obtained by the production method of the present invention.

Advantageous Effects of Invention

The production method of the present invention is useful in production on a commercial scale of a liquid high purity sugar derivative-modified silicone or a composition including the same.

In particular, the present invention is applicable regardless of the type of sugar modifier, and can easily accommodate production on a commercial scale of the liquid high purity sugar derivative-modified silicone or the composition including the same.

For example, the present invention can stably produce the liquid high purity sugar derivative-modified silicone or the composition including the same on a commercial scale even when the boiling point of the sugar modifier, which is difficult to purify by distillation, is high, or the sugar modifier is a polymer compound.

When the composition contains a solvent of the sugar derivative-modified silicone, a solution of a high purity sugar derivative-modified silicone can be produced easily, and production of the solution has excellent yield and productivity, so the method is also suitable for production on a commercial scale.

The production method of the present invention can provide the liquid high purity sugar derivative-modified silicones or compositions including the same with advantageous transparent or translucent appearance since hydrophilic impurities are mostly removed.

In the high purity sugar derivative-modified silicone obtained by the production method of the present invention or the composition including the same, impurities, in particular, impurities derived from a hydrophilic sugar modifier are removed, and therefore phase separation, precipitation of the unreacted starting material, or the like tends not to occur after production. Accordingly, the composition is chemically and/or physically stable.

Accordingly, the production method of the present invention can provide the high purity liquid sugar derivative-modified silicones and the composition including the same in which transparency is high and the transparency is maintained with respect to temperature history and after long term storage, and separation, precipitation, or the like tends not to occur while in the liquid state.

The high purity sugar derivative-modified silicone produced by the present invention or the composition including the same are able to be suitably used in external use preparations or cosmetic compositions and are able to further be widely used in various industrial materials.

DESCRIPTION OF EMBODIMENTS

A first aspect of the present invention is a production method for a liquid high purity sugar derivative-modified silicone or a composition thereof, the method including the steps of: capturing hydrophilic impurities in solid particles by causing an impurity containing composition containing liquid sugar derivative-modified silicone and the hydrophilic impurities derived from a sugar derivative to contact the solid particles, the sugar derivative being a hydrophilic modifier of the sugar derivative-modified silicone, and the solid particles being able to capture the hydrophilic impurities; and separating the sugar derivative-modified silicone and the solid particles.

In the present invention, it is preferable that the sugar derivative-modified silicone is a sugar alcohol-modified silicone.

In the first aspect of the present invention, when the liquid high purity sugar derivative-modified silicone and the composition thereof are produced, a mixture containing the liquid sugar derivative-modified silicone and hydrophilic impurities is caused to come into contact with solid particles that can capture the hydrophilic impurities, the hydrophilic impurities are selectively captured in the solid particles and the liquid sugar derivative-modified silicone and the hydrophilic impurities are separated. The solid particles may be one type or two or more types of solid particles may be used in combination.

"Solid" described above has a meaning of being solid under an environment coming into contact with the impurities, is preferably solid within a range of 20 to 100° C., more preferably solid within a range of 20 to 80° C., and is even more preferably solid at room temperature (25° C.) to 60° C.

The aspect of "contact" described above is not limited, the mixture may be caused to come into contact with the solid particles in some form, for example, may be a form of a layer of the solid particles through which the mixture passes, and the mixture and the solid particles may be in a form of being mixed and stirred.

In a principle of the first aspect of the present invention, the hydrophilic impurities within the mixture containing the liquid sugar derivative-modified silicone and the hydrophilic impurities are such that the hydrophilic impurities causing turbidity of the mixture are effectively captured in the solid particles by treating the hydrophilic impurities that are capturable by the solid particles, are introduced to the solid particle group, absorbed, or held in the solid particle group, and solidified such that solid-liquid separation is possible from a main component that is liquid (high purity sugar derivative-modified silicone). That is, the solid particles selectively gel or solidify the hydrophilic impurities. The solidified hydrophilic impurities can be separated from the liquid sugar derivative-modified silicone by ordinary solid-liquid separation. Accordingly, it is possible to easily obtain the high purity liquid sugar derivative-modified silicone.

"Capture" described above has a meaning of bonding the hydrophilic impurities in some form to the solid particles, and examples include adherence of the hydrophilic impurities to the surface of the solid particles, absorption of the hydrophilic impurities to the inside of the solid particles, introduction to a network formed by the solid particle group, and the like. The bonding may be either physical or chemical bonding. For example, the hydrophilic impurities may be physically bonded to the solid particles, due to intermolecular force, such as Van der Waals force, may be chemically bonded by electrostatic interaction such as ionic bonding or covalent bonding, or may be bonded due to intermolecular force based on polarization such as hydrogen bonding. That is, the solid particles can interact with the impurities. When the hydrophilic impurities are soluble within liquid or the mixture, it is preferable that the hydrophilic impurities themselves are solidified and integrated with the solid particles by gelling and the like by introducing to a network formed by the solid particle group.

For example, it is possible to easily solidify and separate the hydrophilic impurities from the sugar derivative-modified silicone by adding the hydrophilic or ionic crystal particles as the solid particles in the mixture containing the sugar derivative-modified silicone and the hydrophilic impurities and by using these as the core, aggregating the hydrophilic impurities, and growing the crystal particles in bulk.

The hydrophilic impurities may be immobilized as a solid or a gel and easily separated from the sugar derivative-modified silicone by adding crosslinked hydrophilic polymer solid particles as the solid particles in the mixture containing the sugar derivative-modified silicone and the hydrophilic impurities and by absorbing and holding impurities within the three-dimensional network structure of the polymer or within the network formed by the group of solid particles.

The hydrophilic impurities may be solidified and easily separated from the sugar derivative-modified silicone by adding non-crosslinked hydrophilic polymer solid particles as the solid particles in the mixture containing the sugar derivative-modified silicone and the hydrophilic impurities and by, for example, the impurities penetrating within the polymer structure or being absorbed and held, or by impurities being trapped within the aggregated network by intermolecular interactions of the polymer.

The hydrophilic impurities may be easily solidified and separated from the sugar derivative-modified silicone liquid by adding porous solid particles as the solid particles in the mixture containing the sugar derivative-modified silicone and the hydrophilic impurities and by introducing and holding the hydrophilic impurities by a capillary phenomenon or the like within pores, gaps between particles, or the like.

The solid particles can capture the hydrophilic impurities, but the liquid sugar derivative-modified silicone is not captured. Accordingly, only the hydrophilic impurities are captured in the solid particles due to the mixture being caused to come into contact with the solid particles. Therefore it is possible to separate the hydrophilic impurities from the liquid sugar derivative-modified silicone.

Configuring materials of the solid particles are not particularly limited to being able to capture hydrophilic impurities, and it is possible to configure from various inorganic materials, organic materials, or mixtures thereof. The solid particles may be surface treated, and may not be surface treated, but a hydrophilization treatment is preferable when performing surface treatment. It is preferable that the configuring materials of the solid particles have a chemical structure and/or a physical form that can connect with the hydrophilic impurities via intermolecular force or electrostatic interaction, or a covalent bond. The hydrophilic high molecular organic compound is particularly preferable as the configuring material of the solid particles, and a crosslinked hydrophilic high molecular organic compound is most preferable in terms of an effect of increasing purification. The hydrophilic high molecular organic compounds may contain silicon atoms, but preferably the silicon atoms are not contained within the structure. The form of the solid particles is not limited, and may be a spherical form, a cubic form, a rod form, a needle form, a plate form, a column form, a flake form, a granular form, a porous form, an irregular form, a spindle form, a cocoon form, a fibrous form, a bulk form, a dendritic form, a spongy form, a corner form, an angular form, a round form, or a form in which the particles are aggregated in a tuft form or the like. Examples of the inorganic substance include a single inorganic material such as carbon and silicon, and metal oxides such as silicon dioxide, titanium oxide, zirconium oxide, magnesium oxide, calcium oxide, zinc oxide, and alumina. As the inorganic substance, metal oxide is preferable and silicon dioxide is more preferable.

It is preferable that the solid particles include one or more material selected from a silicon atom-free low molecular organic compound, a silicon atom-free non-crosslinked hydrophilic high molecular organic compound, a silicon atom-free crosslinked hydrophilic high molecular organic compound, a salt, a mineral derived material, and activated carbon. Examples of silicon atom-free low molecular organic compound include organic acids such as divalent or higher carboxylic acids or hydroxy acid, or monosaccharides, disaccharides, oligosaccharides, low molecular weight polyphenols, flavonoids having a phenolic hydroxyl group, gallic acid, or esters thereof, nucleic acid bases, derivatives thereof, and the like. A silicon atom-free non-crosslinked hydrophilic polymer compound may have a chain shape structure or a branched chain structure, examples of which include a water-soluble organic polymer such as polysaccharides, polyvinyl alcohol or polyethylene oxide, polyethylene glycol, polyacrylic acid, polyacrylamide, derivatives thereof, and the like. Examples of the silicon atom-free crosslinked hydrophilic polymer organic compound include, but not limited to crosslinked polyacrylates such as carboxyvinyl polymers (carbomers) or salts thereof, partially neutralized products, alkyl-modified crosslinked polyacrylates such as alkyl-modified carboxyvinyl polymers (acrylate/C10-30 alkyl acrylate crosspolymers) or salts thereof, partially neutralized products, crosslinked polyacrylamide, a crosslinked poly (2-acrylamido-2-methylpropanesulfonic acid) polymer, and the like. Examples of the salt include inorganic salt such as sulfate or organic salt such as carboxylic acid salt, various amine salts, and the like. Examples of a mineral derived starting material include layered clay mineral, diatomaceous earth, pearlite, and the like. In particular, a crosslinked hydrophilic organic polymer such as carboxyvinyl polymer (carbomer) and the like is preferable. The solid particles are preferably particulates at room temperature.

The solid particles including a low molecular organic compound can favorably capture impurities with a low molecular weight, and the solid particles including a high molecular organic compound can favorably capture impurities with high molecular weight. The solid particles including a high molecular organic compound can favorably capture impurities with a low molecular weight, but the solid particles including a low molecular organic compound tend not to capture impurities with high molecular weight. Since a sugar modifier generally has high molecular weight, solid particles including a high molecular organic compound has high captureability of hydrophilic impurities.

It is preferable that the solid particles are porous. Examples of a porous inorganic substance include activated carbon, zeolite, diatomaceous earth, perlite, and the like. Examples of the porous organic substance include a porous body of water absorbent resin such as a starch-acrylic acid graft base, a polyacrylate base, a polyvinyl alcohol base, a vinyl acetate-acrylate base, an isobutylene-maleic acid base, and a poly N-vinylacetamide base. Solid particles that include the porous inorganic substance are preferable, or in particular, diatomaceous earth is preferable. The solid particles preferably include the porous organic substance, and in particular, polyacrylate-based superabsorbent resin is preferable.

It is preferable that the solid particles include at least one type of hydrogen bond forming substance and/or at least one type of ionic bond forming substance and/or a hydrate thereof. Many hydrophilic impurities are hydrophilic, and therefore have a hydrogen bond forming property and/or an ionic bond forming property, when the solid particles include a hydrogen bond forming substance and/or the ionic bond forming substance, it is possible to effectively capture the hydrophilic impurities by hydrogen bonding and/or ionic bonding. A hydrate can interact with the hydrophilic impurities, and in particular, can capture moisture within the mixture or an environment and the moisture can bond to the hydrophilic impurities through hydrogen bonding. However, it is preferable that the solid particles include at least one type of hydrogen bond forming substance and/or at least one type of ionic bond forming substance from the viewpoint of affinity with hydrophilic impurities. The hydrogen bond forming substance or the ionic bond forming substance may have a hydrate form having one or more hydration water molecule within its compositional formula.

The hydrogen bond forming substance is not particularly limited as long as the substance is solid that can form hydrogen bonds, but examples include a silicon atom-free hydrophilic low molecular organic compound, a silicon atom-free hydrophilic non-crosslinked high molecular organic compound, a silicon atom-free hydrophilic cross-linked polymer compound, and the like. In particular, a hydrophilic hydrogen bond forming substance is preferable, and a hydrogen bond forming substance that can form two or more hydrogen bonds between molecules is preferable.

The hydrogen bond forming substance preferably has a hydrogen bondable functional group such as a hydroxyl group, a carboxyl group, an aldehyde group, a carbonyl group, an amino group, an amide group, an ether group, and the like. The hydrogen bond forming substance can be selected from, for example, sugars, sugar alcohols, polysaccharides, hydroxyl group-containing polymers, phenols, aldehydes, ketones, carboxylic acids, esters, ethers, amino acids, amines, amides, or salts thereof, or mixtures thereof.

The hydrogen bond forming substance is preferably a solid particulate at room temperature (25° C.) to 60° C.

Examples of the sugar include monosaccharides such as glucose, fructose, galactose, mannose, talose, sorbose, xylose, lyxose, fucose, arabinose, rhamnose, ribose, ribulose, xylulose or sorbitol; disaccharides such as maltose, lactose, cellobiose, trehalose and sucrose; trisaccharides such as maltotriose, galacto-oligosaccharides, fructo-oligos, mannan oligosaccharides, and the like.

Examples of the sugar alcohol include erythritol, threitol, arabinitol, xylitol, mannitol, and the like.

Examples of polysaccharide include starch such as corn starch or derivatives thereof, alginic acid, cellulose, dextrin, glucan, inulin, chitosan, hyaluronic acid, chondroitin sulfate, and the like. It is preferable to use a material that has low crystallinity as the polysaccharide. When hydrophilic impurities are acidic, it is preferable to use a basic polysaccharide such as chitosan, and when hydrophilic impurities are basic, it is preferable to use an acidic polysaccharide such as alginic acid, hyaluronic acid, and chondroitin sulfate from the perspective of increasing purification.

Examples of the hydroxyl group-containing polymer include glycols such as polyethylene glycol, polyethylene oxide, polyethylene glycol/polypropylene glycol copolymers, polyethylene oxide/polypropylene oxide copolymers, and polymers or copolymers of polyvinyl alcohol, hydroxyethyl acrylate, and the like.

Examples of the phenols include phenol, catechol, resorcinol, and hydroquinone; pyrogallol, and the like. However, from the perspective of safety it is preferable to use polyphenols such as gallic acid, catechin, flavonoids, quercetin, anthocyanin, and ellagic acid. The (poly)phenols are particularly excellent in an effect of increasing purification when hydrophilic impurities are basic.

Examples of the aldehydes include glyceraldehyde and the like.

Examples of the ketones include dihydroxyacetone, polyvinylpyrrolidone, and the like.

Examples of the carboxylic acid include saturated mono fatty acids such as capric acid, myristic acid, lauric acid, palmitic acid, stearic acid, and the like; unsaturated mono fatty acids such as trans-crotonic acid; hydroxy acids such as lactic acid, malic acid, glycolic acid, tartaric acid, and citric acid; aromatic carboxylic acids such as benzoic acid, phthalic acid, salicylic acid, gallic acid; dicarboxylic acids such as oxalic acid, malonic acid, succinic acid, glutaric acid, adipic acid, fumaric acid, and maleic acid; polycarboxylic acids such as poly (meth) acrylic acid, polyglutamic acid, polyaspartic acid, and non-crosslinked poly (meth) acrylic acid, crosslinked polyacrylates such as carbomer, alkyl modified crosslinked polyacrylates such as alkyl modified carboxyvinyl polymer (acrylate/C10-30 alkyl acrylate crosspolymer), and anhydrides thereof.

Examples of the esters include hydrophilic or water-soluble polyester polymers, (meth) acrylic acid/(meth) acrylate ester copolymers, crosslinked (meth) acrylic acid/(meth) acrylate ester copolymers, glycolic acid polymers or copolymers, and the like.

Examples of the ethers include glycols such as epoxy resin, polyethylene glycol, polyethylene oxide, polyethylene glycol/polypropylene glycol copolymers, polyethylene oxide/polypropylene oxide copolymers, and the like. In particular, epoxy resin powder is excellent in an effect of trapping the impurities by epoxy-amine reaction when the hydrophilic impurities have amino groups and by epoxy-carboxylic acid reaction when the hydrophilic impurities have carboxylic acid groups, and thus it is useful in a purification-increasing treatment of the present invention.

Examples of the amino acids include alanine, arginine, asparagine, aspartic acid, cysteine, glutamine, glutamic acid, glycine, histidine, leucine, isoleucine, lysine, phenylalanine, proline, serine, threonine, tryptophan, tyrosine, valine, aspartame, pyrrolidonecarboxylic acid, and the like. When the hydrophilic impurities are acidic, it is preferable to use basic amino acids such as lysine, arginine, histidine, tryptophan, ornithine, and when the hydrophilic impurities are basic, it is preferable to use acidic amino acids such as glutamic acid and aspartic acid from the perspective of increasing purification.

Examples of amines include purine bases such as adenine and guanine; pyrimidine bases such as cytosine, various amino resins and amino group-containing polymers, and the like. The amines are particularly superior in an effect of increasing purification where the hydrophilic impurities are basic.

Examples of amides include polyamide, polyacrylamide, crosslinked polyacrylamide, polyoxazoline, nylon powder, and the like.

It is preferable that the hydrogen bond forming substance has a crystal form, but is not limited thereto. As described above, the hydrogen bond forming substance may be in a hydrate form of which compositional formula has a hydration water molecule.

The ionic bond forming substance is not particularly limited as long as the substance is solid that can form ion bonds, but is preferably selected from a silicon atom-free hydrophilic low molecular organic compound, a silicon atom-free hydrophilic non-crosslinked high molecular organic compound, a silicon atom-free hydrophilic crosslinked polymer compound, and the like. As described above, the hydrogen bond forming substance may be in a hydrate form of which compositional formula has a hydration water molecule.

The ionic bond forming substance preferably has an ion-bondable functional group such as a carboxyl group, an amino group, a carboxylate anion group, a sulfonate anion group, and a quaternary ammonium cation group, and may be salts configured from metal elements (mainly cations) and nonmetallic elements (mainly anions), salts comprising metal element (cations) and nonmetal polyatomic ions (anions), and salts comprising nonmetallic polyatomic ions (cations) and nonmetallic elements (anions). The ionic bond forming substance can be selected from, for example, inorganic salts, organic acid salts, quaternary ammonium salts, betaine compounds, polyacrylate salt polymers, vinyl acetate-acrylate polymers, isobutylene-maleate polymers, acrylamide/(meth) acrylate polymers, quaternary ammoniumated polymers of acrylamide/dimethylaminoethyl (meth) acrylate copolymers, salts and partially neutralized products of crosslinked polyacrylates such as carboxyvinyl polymers (carbomers) and the like, salts and partially neutralized products of alkyl modified crosslinked polyacrylates such as alkyl modified carboxyvinyl polymers (acrylates/C10-30 alkyl acrylate crosspolymers), salts and partially neutralized products of crosslinked poly (2-acrylamide-2-methylpropanesulfonic acid) polymers, or mixtures thereof. The ionic bond forming substance is preferably a solid particulate at room temperature.

The hydrate of the hydrogen bond forming substance and the ionic bond forming substance are substances including water molecules within the structure, and can be advantageously used as the solid particles of the present invention. In detail, the substance may be an organic compound or inorganic compound, and is preferably exemplified as trehalose dihydrate, gallic acid monohydrate, citric acid 3 Na dihydrate, catechin hydrate, ellagic acid dihydrate, and the like. Other than this, for example, hydratable inorganic salt is also preferable. The hydratable inorganic salt is an inorganic salt that has a hydration function, and may take the form of an anhydrous salt or may take the form of a hydratable salt. Examples of the hydratable inorganic salt include sulfates such as sodium sulfate, calcium sulfate, and copper sulfate; carbonates such as sodium carbonate; nitrates such as nickel nitrate; phosphates such as calcium phosphate; chlorides such as calcium chloride and magnesium chloride, and the like. The inorganic salt may be water soluble or water insoluble as long as the inorganic salt is solid under an environment of coming into contact with hydrophilic impurities.

The diameter of the solid particles is not particularly limited. The reason for this is as follows. The form of most particles is such that it is not possible to simply and quantitatively be expressed in, for example, spheres or cubes, and the form is complex and irregular, and therefore it is not possible to directly define the particle diameter. Accordingly, if the measurement principle is different, since the definition of diameter, that is, the scale serving as a measurement reference is different, generally, the particle size distribution of solid particles depends on the measurement principle. Further, there is considered to be a difference in a suitable diameter according to the type or nature of the utilized solid particles. As the measurement principle of the particle size distribution of solid particles, it is possible to utilize known methods such as an image analysis method, a Coulter method, a centrifugal sedimentation method, and a laser diffraction/scattering method, when the particle size of an integrated value of 50% in a cumulative weight percentage is considered as a median particle size (median diameter), as a guide, it is preferable that the median particle size is within a range of 1 µm or greater to 1 mm or less. In detail, the median particle size of the solid particles is preferably in the range of 1 to 500 µm, more preferably 5 to 200 µm, and even more preferably 10 to 100 µm. In a case of a large particle (group) such that the median particle size exceeds 1 mm, a removal capability of hydrophilic impurities lowers since total surface area of the particles per unit mass is small. Conversely, in a case of a fine particle group such that the median particle size does not reach 1 µm, clogging tends to occur while the particle has excellent removal capability to the hydrophilic impurities since the total surface area becomes extremely large. Therefore, time, cost, and additional work are needed for filtering out from sugar derivative-modified silicones, and thus, appeal is lowered from the perspective of mass production on a commercial scale. Further, "median particle size" here means median diameter in the volume (weight) particle size distribution measured using a laser diffraction/scattering type particle size distribution measurement instrument.

As an example of the solid particles, a preferable diameter of diatomaceous earth that is one mineral derived material is described. As the diatomaceous earth, it is possible to preferably utilize a dry product, a baked product, a flux fired product, or an acidizing purified product thereof, but a product with large median particle size barely has the effect of the purification-increasing treatment of the present invention, and is not equivalent to the solid particles of the present invention. For example, while the diatomaceous earth solid particle group having the median particle size exceeding 40 µm exhibits almost no effect, the purification-increasing effect of the present invention is recognized in the diatomaceous earth solid particle group in which the median particle size is 30 µm. The diatomaceous earth solid particle group with the median particle size of approximately 20 to approximately 10 µm has an excellent purification-increasing effect. Accordingly, as the diatomaceous earth, it is preferable to have a median particle size of 1 to 35 µm, it is more preferable to have a median particle size of 5 to 30 µm, and it is most preferable to have a median particle size of 10 to 20 µm.

The solid particles preferably finally have a layer form. For example, it is possible to form a layer of the solid particles by mixing and stirring a mixture containing liquid sugar derivative-modified silicones and hydrophilic impurities and the solid particles, leaving for a predetermined time, and sedimenting the solid particles. Thereby, it is possible to effectively capture the hydrophilic impurities using the solid particles, introduce the hydrophilic impurities that cause turbidity of the mixture into the layer, or absorb and hold the hydrophilic impurities within the layer. Even in a method and the like in which the solid particles are filled inside a casing having an entrance and exit in advance, a filter is set in the entrance and exit such that there is no leakage, and the mixture containing the liquid sugar derivative-modified silicones and hydrophilic impurities repeatedly passing within the casing, it is possible to capture the hydrophilic impurities using the solid particles. In this case, the layer of the solid particles is formed in advance in the casing.

The solid particles that capture the hydrophilic impurities are preferably separated from the liquid sugar derivative-modified silicones by suitable means. Since the solid particles are solid and the sugar derivative-modified silicones are liquid, it is possible to use known solid-liquid separation means such as filtration and centrifugation as the separation means. Filtration is preferable in implementation on a commercial scale. Accordingly, as a step in which the sugar derivative-modified silicone and the hydrophilic impurities are separated in the present invention, a filtration step including a filtration material is preferable, and it is more preferable to filter the solid particles and separate from the liquid sugar derivative-modified silicones using the filtration material.

For example, it is possible to separate the liquid sugar derivative-modified silicone and the solid particles by the filtration materials that can remove the particles of 0.5 µm or greater when the solid particles have the particle distribution in a range of 0.5 µm. In detail, after the mixture is caused to come into contact with the solid particles, it is possible to separate the solid particles from the mixture by filtering the solid particles using the filtration material. Since the hydrophilic impurities are captured by the solid particles, it is possible to separate the hydrophilic impurities from the mixture.

The filtration material that separates the solid particles from the liquid sugar derivative-modified silicone is not particularly limited, and examples include filter paper, woven fabric, non-woven fabric, and the like configured by various fibers made of natural fibers such as cellulose, synthetic fibers such as nylon, polypropylene, polyethersulfone, cellulose acetate, PTFE, polyethylene terephthalate, stainless steel, glass fiber, or a mixture thereof, and various filters comprising the porous inorganic substances or the porous organic substances, and the like.

In the filtration step, it is preferable to further use a filter aid. The filter aid is preferably powder or fiber, and more preferably uses one or more selected from activated carbon, diatomaceous earth, pearlite, glass (particles or fibers), cellulose (powder or fibers), and derivatives thereof. It is also possible to use the solid particles as the filter aid.

When the filter aid is powder, it is preferable that the median particle size is 5 µm or greater. In detail, the median particle size of the filter aid is preferably in the range of 5 to 100 µm, more preferably 10 to 60 µm, and even more preferably 20 to 50 µm. The median particle size can be measured by a known measurement instrument that uses the image analysis method, the Coulter method, the centrifugal sedimentation method, the laser diffraction/scattering method, and the like. Further, "median particle size" here means median diameter in the volume (weight) particle size distribution measured using a laser diffraction/scattering type particle size distribution measurement instrument.

A separation step is preferably implemented in a range of 0 to 100° C., more preferably in a range of 15 to 80° C., and even more preferably in a range of room temperature (25° C.) to 60° C.

In the present invention, in the first aspect, it is preferable that the mixture of the liquid sugar derivative-modified silicone and the hydrophilic impurities are caused to come into contact with the solid particles in the capturing step after dilution using a solvent that is a good solvent for the sugar derivative-modified silicone and a poor solvent for the hydrophilic impurities.

The solvent may be selected from the good solvent for the liquid sugar derivative-modified silicone and the poor solvent for the hydrophilic impurities, and may be, for example, a hydrophobic solvent. Diluting the mixture containing the liquid sugar derivative-modified silicone and the hydrophilic impurities with the solvent has an effect of aggregating the hydrophilic impurities with each other, increasing the size thereof, tending to capture the hydrophilic impurities in the solid particles, and tending to separate the hydrophilic impurities from the liquid sugar derivative-modified silicone. Since it is possible to effectively lower viscosity of the extremely viscous sugar derivative-modified silicone in an undiluted state by diluting the liquid sugar derivative-modified silicone in the solvent, a solid and liquid separation operation is easy.

As the solvent that is the good solvent for the liquid sugar derivative-modified silicone and the poor solvent for the hydrophilic impurities, hydrophobic solvent is preferable, and examples include aliphatic hydrocarbons such as pentane and heptane; aromatic hydrocarbons such as benzene and toluene; silicones such as dimethylpolysiloxane, methylphenylpolysiloxane, cyclic silicone, and caprylyl methicone, and the like. The solvent is preferably volatile.

In a case of dilution in the solvent, it is possible to easily produce a high purity sugar derivative-modified silicone solvent, and the solvent is advantageous in production on a commercial scale of a high purity sugar derivative-modified silicone composition.

Meanwhile, the production method of the present invention may include a step of heating and/or depressurizing the mixture and removing the solvent after the separating step. The heating temperature is not particularly limited, and for example, the heating temperature can be set to 40 to 120° C. The degree of depressurization is not particularly limited, and for example, the degree of depressurization can be set to 0.01 to 0.8 atmospheric pressure. Heating time and the degree of depressurization is not particularly limited, but for example, can be set to 10 minutes to 24 hours.

In a case of removing the solvent, it is possible to easily produce a high purity sugar derivative-modified silicone, and it is advantageous in production on a commercial scale of a high purity sugar derivative-modified silicone composition.

The first aspect of the present invention, for example, can be implemented by filtering a composition obtained by mixing the solid particles in an impurity containing composition (mixture) containing the liquid sugar derivative-modified silicone and the hydrophilic impurities and removing the solid particles from the composition, and thereby, it is possible to separate the liquid sugar derivative-modified silicone and the hydrophilic impurities.

The hydrophilic impurities are not particularly limited as long as the hydrophilic impurities are hydrophilic, but typically, are a sugar derivative (sugar modifier) or a derivative thereof that is one production starting material of the sugar derivative-modified silicone. Examples of the sugar derivative include, as will be described later, the sugar derivative having one reactive unsaturated group per molecule such as a sugar derivative having a carbon-carbon double bond at the end of the molecular chain, and preferably, a sugar monounsaturated ether compound. Sugar is given as the material derived from the sugar derivative. For example, when the sugar modifier is a monoallyl etherified sugar, most of the surplus of the modifier is isomerized to a monopropenyl etherified sugar causing odorization after a synthesis reaction with the sugar derivative-modified silicone, and therefore, after a synthesis step, it is preferable to implement an acidizing step described later and subject a propenyl ether to hydrolysis and convert the product to sugar. Accordingly, after the acidizing step, sugar itself is included in the hydrophilic impurities. Since sugar itself has low affinity to the sugar derivative-modified silicone as compared to the sugar monounsaturated ether compound, the sugar itself is barely dissolved within the modified silicone. Accordingly, it is possible to achieve more excellent high-purification by more effectively capturing and removing the hydrophilic impurities by implementing the high-purification treatment using the solid particles of the present invention after the acidizing step.

The liquid sugar derivative-modified silicone of the present invention will be described below.

Sugar Derivative-modified Silicone

The sugar derivative-modified silicone to which the present invention can be applied is a silicone compound modified with a sugar derivative and is a liquid composition, and it is preferably a liquid at least at a temperature of 100° C. The chemical structure or the like is not particularly limited as long as the composition satisfies this condition.

In the present invention, a "liquid form" or a "liquid" means that after the liquid surface of an organopolysiloxane in a prescribed container is placed horizontally and the vessel is then inclined, the liquid surface can once again become horizontal after 1 hour, preferably after 30 minutes, and more preferably after 10 minutes. Here, "horizontal" means to form a plane that intersects the direction of gravitational force at a right angle. The sugar derivative-modified silicone is preferably a liquid at least at 100° C. but more preferably also exhibits liquidity in a range of 100° C. or lower to room temperature. Specifically, the sugar derivative-modified silicone is preferably a liquid at 80° C., more preferably a liquid at 40° C., and even more preferably a liquid at room temperature (25° C.). Compositions that are in the liquid state at a temperature of not lower than 100° C. are, of course, included in the scope of the liquid sugar derivative-modified silicone, but sugar derivative-modified silicones that demonstrate liquidity when heated to, for example, 100° C. even if they are in a semi-gelatinous form or a soft solid form without fluidity at room temperature (25° C.) or lower are also included.

The sugar derivative-modified silicone may be a sugar derivative-modified silicone represented by the following general formula (1):

[Chemical Formula 7]

$$R^1_a R^2_b L^1_c Q_d SiO_{(4-a-b-c-d)/2} \quad (1)$$

(wherein, $R^1$ represents a monovalent organic group (however, excluding $R^2$, L, and Q), a hydrogen atom or a hydroxyl group, and $R^2$ is a substituted or unsubstituted, straight or branched monovalent hydrocarbon group having from 9 to 60 carbons, or a chain organosiloxane group represented by the following general formula (2-1):

[Chemical Formula 8]

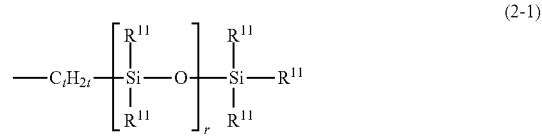

(2-1)

(wherein, $R^{11}$ is independently a substituted or unsubstituted monovalent hydrocarbon group having from 1 to 30 carbons, hydroxyl groups, or hydrogen atoms, and at least one of the $R^{11}$ is the monovalent hydrocarbon group. t is a number in a range of 2 to 10, and r is a number in a range of 1 to 500), or the following general formula (2-2):

[Chemical Formula 9]

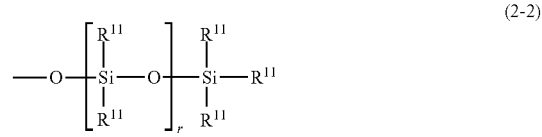

(2-2)

(wherein, $R^{11}$ and r are as described above), and $L^1$ represents a silylalkyl group having a siloxane dendron structure and represented by the following general formula (3) when i=1:

[Chemical Formula 10]

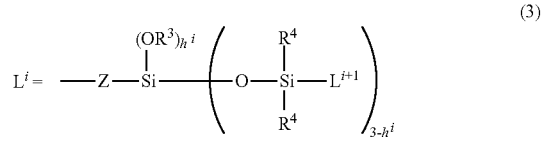

(3)

(wherein, each $R^3$ independently represents a substituted or unsubstituted, straight or branched monovalent hydrocarbon group having from 1 to 30 carbons, each $R^4$ independently represents an alkyl group or phenyl group having from 1 to 6 carbons, Z represents a divalent organic group, i represents a generation of the silylalkyl group represented by $L^i$ and is an integer of 1 to k when k is a number of generations that is a number of repetitions of the silylalkyl group, the number of generations k is an integer from 1 to 10, $L^{i+1}$ is the silylalkyl group when i is less than k, and $R^4$ when i=k, and $h^i$ is a number in a range of 0 to 3), Q represents a sugar derivative group, and a, b, c, and d are numbers respectively in ranges of 1.0≤a≤2.5, 0≤b≤1.5, 0≤c≤1.5, and 0.0001≤d≤1.5).

Here, when the sugar derivative-modified silicone represented by general formula (1) has the long chain organic group or the chain organosiloxane group represented by $R^2$ as described above, b is a number greater than 0, preferably 0.0001≤b≤1.5, and more preferably 0.001≤b≤1.5. Similarly, when the sugar derivative-modified silicone represented by general formula (1) has a silylalkyl group having the siloxane dendron structure represented by $L^1$ as described above, c is a number greater than 0, preferably 0.0001≤c≤1.5, and more preferably 0.001≤c≤1.5.

The sugar derivative-modified silicone preferably has a long chain organic group or chain organosiloxane group represented by $R^2$ or a silylalkyl group having a siloxane dendron structure represented by $L^1$ together with the sugar derivative group serving as Q.

At this time, the suitable values of b and c are represented as follows by essential functional groups.

(1) In the case of having a group represented by $R^2$: 0.001≤b≤1.5 and 0≤c≤1.5.

(2) In the case of having a group represented by $L^1$: 0≤b≤1.5 and 0.001≤c≤1.5.

(3) In the case of having both a group represented by $R^2$ and a group represented by $L^1$: 0.001≤b≤1.5 and 0.001≤c≤1.5.

The monovalent organic groups represented by $R^1$ in general formula (1) can be the same or different and are not particularly limited as long as the groups are not the functional groups of $R^2$, $L^1$, and Q. However, the groups are preferably a substituted or unsubstituted, straight-chain or branched monovalent hydrocarbon group having from 1 to 8 carbons, a (poly)oxyalkylene group represented by —$R^5$O(AO)$_n$R$^6$ (in the formula, AO represents an oxyalkylene group having from 2 to 4 carbons; $R^5$ represents a substituted or unsubstituted, straight-chain or branched divalent hydrocarbon group having from 3 to 5 carbons; $R^6$ represents a substituted or unsubstituted, straight-chain or branched monovalent hydrocarbon group having from 1 to 24 carbons and hydrogen atoms or a substituted or unsubstituted, straight-chain or branched acyl group having from 2 to 24 carbons; and n is from 1 to 100), an alkoxy group, a hydroxyl group, or a hydrogen atom. However, not all of the $R^1$ are hydroxyl groups, hydrogen atoms, alkoxy groups, or (poly) oxyalkylene groups.

Examples of a monovalent hydrocarbon group having from 1 to 8 carbons include alkyl groups such as a methyl group, ethyl group, propyl group, butyl group, pentyl group, hexyl group, heptyl group, octyl group, and the like; cycloalkyl groups such as a cyclopentyl group, cyclohexyl group, and the like; alkenyl groups such as a vinyl group, allyl group, butenyl group, and the like; aryl groups such as a phenyl group, tolyl group, and the like; aralkyl groups such as a benzyl group; and groups wherein the hydrogen atoms bonded to the carbon atoms of these groups are substituted at least partially by fluorine or a similar halogen atom, or an organic group including an epoxy group, a glycidyl group, an acyl group, a carboxyl group, an amino group, a (meth) acryl group, a mercapto group, or the like (however, the total number of carbons is from 1 to 8). The monovalent hydrocarbon group is preferably a group other than an alkenyl group, and is particularly preferably a methyl group, an ethyl group, or a phenyl group. Additionally, examples of the alkoxy group include lower alkoxy groups such as methoxy groups, ethoxy groups, isopropoxy groups, and butoxy groups and higher alkoxy groups such as lauryl alkoxy groups, myristyl alkoxy groups, palmityl alkoxy groups, oleyl alkoxy groups, stearyl alkoxy groups, and behenyl alkoxy groups.

In particular, the $R^1$ are preferably monovalent hydrocarbon groups having from 1 to 8 carbons and that are free of unsaturated aliphatic bonds or monovalent fluorinated hydrocarbon groups. Examples of the monovalent hydrocarbon group not having unsaturated aliphatic bonds belonging to the $R^1$ include alkyl groups such as methyl groups, ethyl groups, propyl groups, butyl groups, pentyl groups, and hexyl groups; aryl groups such as phenyl groups, tolyl groups, and xylyl groups; and aralkyl groups such as benzyl groups. Examples of the monovalent fluorinated hydrocarbon group include perfluoroalkyl groups such as trifluoropropyl groups, and pentafluoroethyl groups. From an industrial perspective, $R^1$ is preferably a methyl group, an ethyl group, or a phenyl group, and more preferably from 90 mol % to 100 mol % of all the $R^1$ are selected from methyl groups, ethyl groups, or phenyl groups.

A sugar derivative-modified silicone aims at imparting additional functionality, and it is possible to introduce or design a modified group other than a sugar derivative group (-Q), particularly a short chain or medium chain hydrocarbon based group, as $R^1$. Specifically, when $R^1$ is a substituted monovalent hydrocarbon group, it is possible to appropriately select a substituent in accordance with desired characteristics and uses. For example, when using the sugar derivative-modified silicone as a cosmetic composition or a fiber treating agent starting material, it is possible to introduce an amino group, amide group, aminoethyl aminopropyl group, carboxyl group, and the like, as the substituted group of a monovalent hydrocarbon group, for the purpose of improving the sensation during use, feeling to touch, persistence, and the like.

The substituted or unsubstituted, straight or branched monovalent hydrocarbon group having from 9 to 60 carbons of $R^2$ of general formula (1) is a long chain hydrocarbon group or a chain organosiloxane group represented by general formula (2-1) or (2-2). By introducing this group at the main chain and/or side chain of polysiloxane, it is possible to further improve the affinity, emulsifiability, and dispersibility, and further improve the sensation during use of various components such as an oil agent, powder, or the like incorporated in an external use preparation or a cosmetic composition. Furthermore, because the monovalent long chain hydrocarbon group or chain organopolysiloxane group is a hydrophobic functional group, the compounding stability and the compatibility with organic oils having a high content of alkyl groups are further improved. $R^2$ may be all the monovalent long chain hydrocarbon group or all the chain organopolysiloxane group, or may be a functional group of both of these groups. In the sugar derivative-modified silicone, it is particularly preferable that part or all of $R^2$ is a monovalent long chain hydrocarbon group, and by having such a monovalent long chain hydrocarbon group in a molecule, the sugar derivative-modified silicone exhibits superior compatibility not only with silicone oil, but with non silicone oil with a high alkyl group content as well. For example, it is possible to obtain an emulsion and a dispersion with superior stability over time and thermal stability, which are made of non silicone oil.

Substituted or unsubstituted, straight or branched monovalent hydrocarbon groups that are represented by $R^2$ of general formula (1), that are bonded to silicon atoms, and that have from 9 to 60 carbons, may be the same or different. Furthermore, the structure thereof is selected from among straight chain, branched, and partially branched. In the present invention, an unsubstituted straight chain monovalent hydrocarbon group is particularly preferably used. An unsubstituted monovalent hydrocarbon group can be, for example, an alkyl group, aryl group, or aralkyl group having from 9 to 60 carbons, preferably from 9 to 30 carbons, and more preferably from 10 to 25 carbons. Meanwhile, examples of the substituted monovalent hydrocarbon group include perfluoroalkyl groups, aminoalkyl groups, amide alkyl groups, and ester groups having from 9 to 30 carbons, preferably from 9 to 30 carbons, and more preferably from 10 to 24 carbons. Additionally, the carbon atoms of the monovalent hydrocarbon groups may be partially substituted with alkoxy groups, and examples of said alkoxy groups include methoxy groups, ethoxy groups, and propoxy groups. This type of monovalent hydrocarbon group is particularly preferably an alkyl group having from 9 to 30 carbons, and an example thereof is a group represented by the general formula —$(CH_2)_{v'}$—$CH_3$ (v' is a number in a range of 8 to 29). Particularly, an alkyl group having from 10 to 24 carbons is preferable.

The chain organosiloxane group in general formula (2-1) or (2-2) has a straight chain polysiloxane chain structure, unlike a silylalkyl group, which has a siloxane dendron structure. In general formula (2-1) or (2-2), each $R^{11}$ is independently a substituted or unsubstituted monovalent hydrocarbon group having from 1 to 30 carbons, a hydroxyl group, or a hydrogen atom. The substituted or unsubstituted monovalent hydrocarbon group having from 1 to 30 carbons is preferably an alkyl group having from 1 to 30 carbons, an aryl group having from 6 to 30 carbons, an aralkyl group having from 6 to 30 carbons, or a cycloalkyl group having from 6 to 30 carbons, and is exemplified by a methyl group, ethyl group, propyl group, butyl group, pentyl group, hexyl group, heptyl group, octyl group, decyl group, or other alkyl group; a cyclopentyl group, cyclohexyl group, or other cycloalkyl group; or a phenyl group, tolyl group, or other aryl group. The hydrogen atoms bonded to the carbon atoms of these groups may be substituted at least partially by fluorine or a similar halogen atom, or an organic group including an epoxy group, acyl group, carboxyl group, amino group, methacryl group, mercapto group, or the like. A methyl group, a phenyl group, or a hydroxyl group is particularly preferable as $R^{11}$. A configuration in which a part of $R^{11}$ is a methyl group and another part of $R^{11}$ is a long chain alkyl group having from 8 to 30 carbons is also preferable.

In general formula (2-1) or (2-2), t is a number in a range of 2 to 10; r is a number in a range of 1 to 500; and r preferably is a number in a range of 2 to 500. Such a straight chain organosiloxane group is hydrophobic. From the perspective of compatibility with various oil agents, r preferably is a number in a range of 1 to 100, and particularly preferably is a number in a range of 2 to 30.

A silylalkyl group having a siloxane dendron structure shown by general formula (3) is a functional group that includes a structure wherein a carbosiloxane unit spreads in a dendrimer shape and that exhibits high water repellence. The silylalkyl group is well-balanced when combined with hydrophilic groups, and when an external use preparation or cosmetic composition that incorporates the sugar derivative-modified silicone is used, the silylalkyl group inhibits an unpleasant sticky feeling, and provides a refreshingly natural feeling to the touch. Additionally, the silylalkyl group having a siloxane dendron structure is chemically stable, and for this reason, the silylalkyl group is a functional group providing advantageous properties such as usability in combination with a wide range of components.

Examples of the substituted or unsubstituted, straight or branched monovalent hydrocarbon group having from 1 to 30 carbons (the $R^3$ in general formula (3)) include alkyl groups such as a methyl group, ethyl group, propyl group, butyl group, pentyl group, hexyl group, heptyl group, octyl group, and the like; cycloalkyl groups such as a cyclopentyl group, cyclohexyl group, and the like; alkenyl groups such as a vinyl group, allyl group, butenyl group, and the like; aryl groups such as a phenyl group, tolyl group, and the like; aralkyl groups such as a benzyl group; and groups wherein the hydrogen atoms bonded to the carbon atoms of these groups are substituted at least partially by fluorine or a similar halogen atom, or an organic group including an epoxy group, a glycidyl group, an acyl group, a carboxyl group, an amino group, a (meth)acryl group, a mercapto group, or the like (provided that the total number of carbons is from 1 to 30).

Among the phenyl group or the alkyl group having from 1 to 6 carbons represented by $R^4$ in general formula (3), examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups.

In general formula (3), when i=k, $R^4$ is preferably a methyl group or a phenyl group. In particular, $R^4$ is preferably a methyl group when i=k.

From an industrial standpoint, the number of generations k is preferably an integer of 1 to 3, and more preferably is 1 or 2. In each of the number of generations, the group represented by $L^1$ is represented as follows. In the formulae, $R^3$, $R^4$, and Z are the same groups as described above.

When the number of generations is k=1, $L^1$ is represented by the following general formula (3-1).

[Chemical Formula 11]

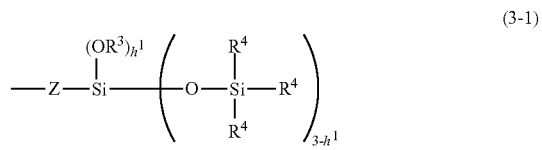

(3-1)

When the number of generations is k=2, $L^1$ is represented by the following general formula (3-2).

[Chemical Formula 12]

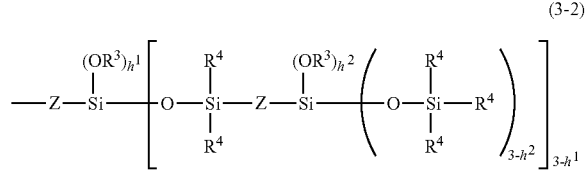

(3-2)

When the number of generations is k=3, $L^1$ is represented by the following general formula (3-3).

[Chemical Formula 13]

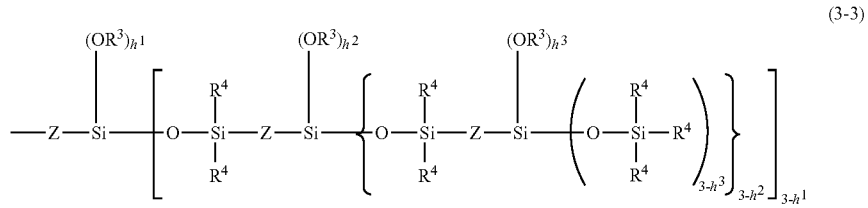

(3-3)

In the structures represented by the general formulae (3-1) to (3-3) when the number of generations is from 1 to 3, each of $h^1$, $h^2$ and $h^3$ is independently a number in a range of 0 to 3. These $h^1$ are preferably a number in a range of 0 to 1, and $h^i$ is particularly preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not limited to the functional groups described above. Preferably, each Z is independently a group selected from divalent organic groups represented by the following formula:

[Chemical Formula 14]

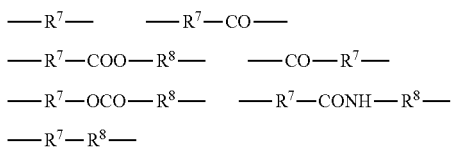

Of these, Z in $L^1$ is preferably a divalent organic group represented by general formula —$R^7$— that is introduced by a reaction between a silicon-bonded hydrogen atom and an alkenyl group. Likewise, Z is preferably a divalent organic group represented by general formula —$R^7$—COO—$R^8$— that is introduced by a reaction between a silicon-bonded hydrogen atom and an unsaturated carboxylic ester group.

Meanwhile, in the silylalkyl group represented by $L^i$, in which the number of generations k is 2 or greater, and Li is $L^2$ to $L^k$, Z is preferably an alkylene group having from 2 to 10 carbons or a divalent organic group represented by —$R^7$—COO—$R^8$—, and is particularly preferably a group selected from an ethylene group, a propylene group, a methylethylene group, a hexylene group, and —$CH_2C(CH_3)$COO—$C_3H_6$—.

In the general formula described above, each $R^7$ is independently a substituted or unsubstituted straight or branched chain alkylene group or alkenylene group having from 2 to 22 carbons or an arylene group having from 6 to 22 carbons. More specifically, examples of $R^7$ include straight alkylene groups such as an ethylene group, a propylene group, and a butylene group, a hexylene group; and branched alkylene groups such as a methylmethylene group, a methylethylene group, a 1-methylpentylene group, and a 1,4-dimethylbutylene group. $R^8$ is preferably a group selected from an ethylene group, a propylene group, a methylethylene group, and a hexylene group.

In the general formula described above, $R^8$ is preferably a group selected from divalent organic groups expressed by the following formula.

[Chemical Formula 15]

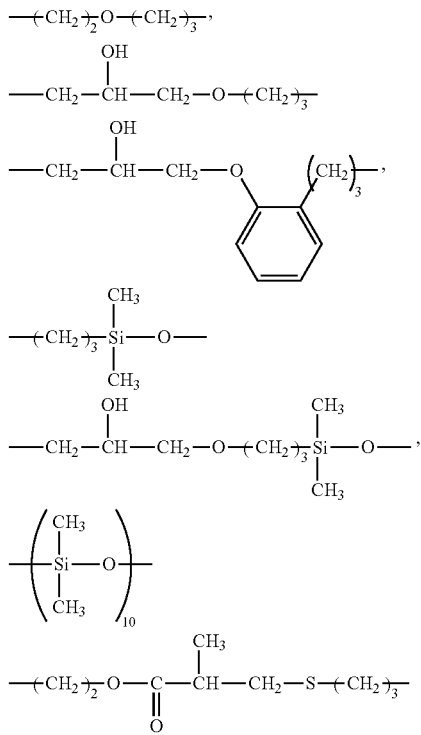

In general formula (1), Q is a sugar derivative group, and forms the hydrophilic site of the sugar derivative-modified silicone. The structure of Q is not limited provided that the structure has a sugar derivative site, but the sugar derivative residue is preferably bonded to the silicon atom via a divalent organic group.

In general formula (1), it is possible for Q to be a group derived from monosaccharides, disaccharides, or oligosaccharides. In this case, the sugar derivative-modified silicone according to the present invention is modified using monosaccharides, disaccharides, or oligosaccharides.

In general formula (1), it is preferable for Q to be a group derived from sugar alcohols. Accordingly, Q is preferably a sugar alcohol group-containing organic group. In the sugar alcohol group-containing organic group, it is preferable that sugar alcohol residue is bonded to the silicon atom via the divalent organic group. In this case, the sugar derivative-modified silicone in the present invention is modified using sugar alcohols.

Q is particularly preferable as in general formula (4-1) below:

[Chemical Formula 16]

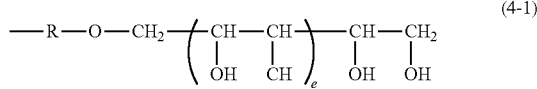

(wherein, R represents a divalent organic group, and e is 1 or 2) or can be represented by the following general formula (4-2):

[Chemical Formula 17]

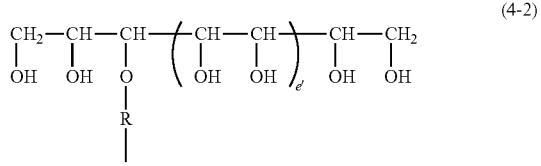

(wherein, R is as described above, and e' is 0 or 1).

In the sugar derivative-modified silicone according to the present invention, preferably at least one type of the sugar alcohol-containing organic group that is represented by general formulas (4-1) or (4-2) above is bonded to the silicon atom. Further, the organopolysiloxane may have two or more types of sugar alcohol-containing organic groups selected from these sugar alcohol-containing organic groups in the same molecule. In the same manner, the mixture of the organopolysiloxanes having different sugar alcohol-containing organic groups may be used.

The divalent organic group represented by R in general formula (4-1) or (4-2) is not particularly limited, and examples of the divalent organic group include substituted or unsubstituted, and linear or branched divalent hydrocarbon groups having 1 to 30 carbons. A substituted or unsubstituted straight or branched divalent hydrocarbon group having from 3 to 5 carbons is preferable. Examples of the substituted or unsubstituted, straight-chain or branched divalent hydrocarbon group having from 1 to 30 carbons include: straight-chain or branched alkylene groups having from 1 to 30 carbons such as the methylene group, dimethylene group, trimethylene group, tetramethylene group, pentamethylene group, hexamethylene group, heptamethylene group, octamethylene group, or the like; alkenylene groups having from 2 to 30 carbons such as the vinylene group, allylene group, butenylene group, hexenylene group, octenylene group, or the like; arylene groups having from 6 to 30 carbons such as the phenylene group, diphenylene group, or the like; alkylenearylene groups having from 7 to 30 carbons such as the dimethylenephenylene group or the like; and substituted groups thereof in which hydrogen atoms bonded to carbons of the groups are at least partially substituted by a halogen atom such as a fluorine atom or the like, or an organic group including the carbinol group, epoxy group, glycidyl group, acyl group, carboxyl group, amino group, methacryl group, mercapto group, amide group, oxyalkylene group, or the like. The divalent hydrocarbon groups are preferably alkylene groups having from 1 to 30 carbons, preferably are alkylene groups having from 1 to 6 carbons, and even more preferably alkylene groups having from 3 to 5 carbons.

A sugar alcohol-containing organic group of general formula (4-1) wherein R is a propylene group and e=1 is particularly preferable. Similarly, a sugar alcohol-containing organic group of general formula (4-2) wherein R is a propylene group and e=0 is particularly preferable. Corresponding to general formula (4-1) or (4-2), the sugar alcohol-containing organic group in this case is xylitol residue represented by structural formula: —C$_3$H$_6$—OCH$_2$[CH(OH)]$_3$CH$_2$OH, or structural formula: —C$_3$H$_6$—OCH{CH(OH)CH$_2$OH}$_2$ (hereinafter, simply referred to as "xylitol residue" or "xylitol modified group").

The bond position of the sugar derivative and preferably the sugar alcohol-containing organic group may be either the terminal or side chain of polysiloxane, which is the main chain; and the structure may have two or more sugar derivative groups per molecule of sugar derivative-modified silicone. The two or more sugar derivative groups may be the same or different sugar derivative groups. The two or more sugar derivative groups may be structured such that bonding occurs only in a side chain of the polysiloxane that is the main chain, only at a terminal, or in the side chain and at the terminal.

It is possible to obtain the non-crosslinked sugar derivative-modified silicone by, for example, reacting (a) a sugar derivative having one reactive unsaturated group per molecule, (b) organopolysiloxane having silicon atom bonded hydrogen atoms, and (c) an organic compound having one reactive unsaturated group per molecule, and if necessary, (d) a siloxane dendron compound having one reactive unsaturated group per molecule, and/or (e) a long chain hydrocarbon compound or a chain organopolysiloxane compound having one reactive unsaturated group per molecule in the presence of a hydrosilylation reaction catalyst. The reactive unsaturated group described above preferably is an unsaturated functional group having a carbon-carbon double bond, and is exemplified by an alkenyl group or unsaturated fatty acid ester group. —R$^1$ is introduced by component (c), -L$^1$ is introduced by component (d), and —R$^2$ is introduced by component (e).

(a) the sugar derivative having one reactive unsaturated group per molecule is an organopolysiloxane modifier, and may become the hydrophilic impurities in the present invention.

More specifically, it is possible to obtain the sugar derivative-modified silicone as described below, for example.

It is possible to obtain the sugar derivative-modified silicone by addition reacting with organopolysiloxane having a silicon-hydrogen bond, an unsaturated organic compound having a carbon-carbon double bond at one terminal of the molecular chain, and an unsaturated ether compound of a sugar derivative having a carbon-carbon double bond in the molecule. Furthermore, a siloxane dendron compound having a carbon-carbon double bond at one terminal of the molecular chain, and/or an unsaturated long chain hydrocarbon compound having a carbon-carbon double bond at one terminal of the molecular chain, or a chain organopolysiloxane having a carbon-carbon double bond at one terminal of the molecular chain can be further addition reacted.

In the above case, it is possible to obtain the sugar derivative-modified silicone as the product of a hydrosilylation reaction between the unsaturated organic compound and the sugar derivative unsaturated ether compound, and optionally the siloxane dendron compound and/or an unsaturated long chain hydrocarbon compound, or a chain organopolysiloxane having a carbon-carbon double bond at one terminal of the molecular chain and a SiH group-containing organopolysiloxane. This enables the introduction of an organic group and a sugar derivative group, and optionally a silylalkyl group having a siloxane dendron structure and/or a long chain hydrocarbon group or a chain organopolysiloxane group into the polysiloxane chain. This reaction can be performed as a batch or can take the form of successive reactions. However, successive reactions are preferable from the perspectives of safety and quality control.

For example, it is possible to obtain the sugar derivative-modified silicone by reacting, in the presence of a hydrosilylation reaction catalyst, at least (b1) organohydrogenpolysiloxane represented by the following formula (1'):

[Chemical Formula 18]

(wherein, $R^1$, a, b, c, and d are as described above) and (a) a sugar derivative having one reactive unsaturated group per molecule. It is preferable to further react (d) a siloxane dendron compound having one reactive unsaturated group per molecule, and/or (e) a hydrocarbon compound having one reactive unsaturated group per molecule, or chain organopolysiloxane having one reactive unsaturated group per molecule.

It is possible to preferably produce the sugar derivative-modified silicone by reacting together component (a), component (d) and/or component (e), as well as (b1) the organohydrogenpolysiloxane, or by successively addition reacting the (b1) organohydrogenpolysiloxane and optionally the component (d), and/or the component (e), and further addition reacting the component (a), in the state where (a) a sugar derivative having one reactive unsaturated group per molecule, and optionally (d) a siloxane dendron compound having one reactive unsaturated group per molecule, and/or (e) a hydrocarbon compound having one reactive unsaturated group per molecule or a chain organopolysiloxane having one reactive unsaturated group per molecule coexist.

(b) organopolysiloxane having silicon atom-bonded hydrogen atoms used in the synthesis of the sugar derivative-modified silicone is preferably (b2) an organohydrogensiloxane represented by, for example, the following structural formula (1-1)':

[Chemical Formula 19]

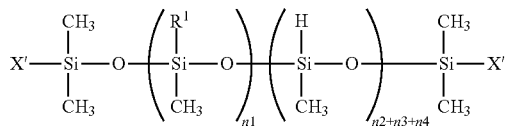

(wherein, each $R^1$ is independently as described above, X' is a group selected from $R^1$ or hydrogen atoms, and n1, n2, n3, and n4 are each independently a number in a range of 0 to 2,000, and n1+n2+n3+n4 is a number in a range of 0 to 2,000, however, when n2+n3+n4=0, at least one X' is a hydrogen atom).

The sugar derivative-modified silicone is preferably synthesized by subjecting to a hydrosilylation reaction (a1) a sugar derivative having a carbon-carbon double bond at a terminal of the molecular chain, and (b2) an organohydrogenpolysiloxane; and the organohydrogenpolysiloxane (component (b2)) is preferably the organohydrogenpolysiloxane obtained by successively addition reacting the component (d) and/or the component (e). In this case, the organohydrogenpolysiloxane immediately prior to reaction with component (a) (after successive reactions with other components) is preferably represented by the following structural formula (1-1A).

[Chemical Formula 20]

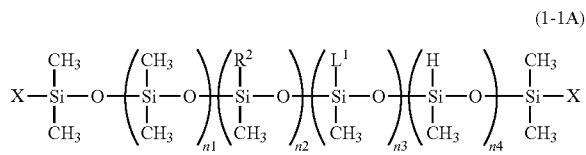

(Wherein, each of $R^2$ and $L^1$ is independently as described above, X is a group selected from a group formed of methyl, $R^2$ and $L^1$ and hydrogen atoms (H), and n1, n2, n3, and n4 are each independently a number in a range of 0 to 2,000, and n1+n2+n3+n4 is a number in a range of 0 to 2,000, however, when n4=0, at least one X is a hydrogen atom).

A sugar derivative having one reactive unsaturated group per molecule, which is used in the synthesis of the sugar derivative-modified silicone, is preferably (a1) a sugar derivative having a carbon-carbon double bond at the terminal of molecular chain. As the sugar derivative having one reactive unsaturated group per molecule, it is possible to use the same compound as (B) a sugar derivative group-containing organic compound that has the reactive unsaturated group described later with a condition of one reactive unsaturated group being present in each molecule.

(a) the sugar derivative having one reactive unsaturated group per molecule, for example, (a1) the sugar derivative having a carbon-carbon double bond at the terminal of molecular chain is an organopolysiloxane modifier, and may become the hydrophilic impurities in the present invention.

(d) The siloxane dendron compound having one reactive unsaturated group per molecule used in the synthesis of the sugar derivative-modified silicone is preferably a compound having a siloxane dendron structure with one carbon-carbon double bond at a molecular terminal, represented by the following general formula (3'):

[Chemical Formula 21]

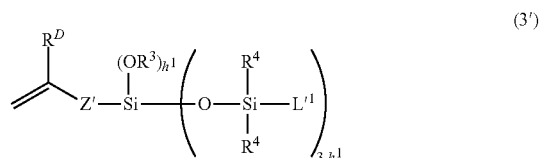

(Wherein, $R^3$ and $R^4$ are as described above, $R^D$ is hydrogen atoms or the methyl group, Z' represents a divalent organic group similar to Z, $h^1$ is a number in a range of 0 to 3, and $L'^1$ represents $R^4$ or a silylalkyl group represented in the following general formula (3") when j=1:

[Chemical Formula 22]

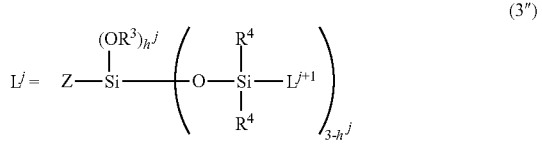

(3″)

(wherein, $R^3$ and $R^4$ are as described above, Z represents the divalent organic group, j represents the generation of the silylalkyl group that is represented by $L^3$, when the number of generations serving as a number of repetitions of the silylalkyl group is k', j is an integer of 1 to k', and the number of generations k' is an integer of 1 to 9; $L^{j+1}$ is the silylalkyl group when j is less than k' and is $R^4$ when j=k', and $h^3$ is a number in a range of 0 to 3)).

(e) The hydrocarbon compound having one reactive unsaturated group per molecule or chain organopolysiloxane having one reactive unsaturated group per molecule used in the synthesis of the sugar derivative-modified silicone of the present invention, is preferably a mono unsaturated organic compound represented by the following general formula (2'):

[Chemical Formula 23]

R'—R²'  (2')

(Wherein, R' represents the unsaturated organic group, $R^2$ represents a substituted or unsubstituted, straight or branched monovalent hydrocarbon group having from 7 to 58 carbons) or the following general formula (2'-1):

[Chemical Formula 24]

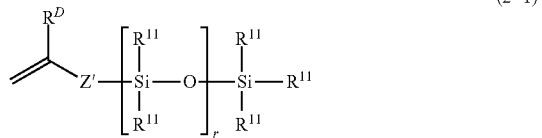

(2'-1)

(wherein, $R^D$, Z', $R^{11}$, and r are as described above).

The hydrocarbon compound having one reactive unsaturated group per molecule (e) is preferably a monounsaturated hydrocarbons having from 9 to 30 carbons and is more preferably a 1-alkene. Examples of the 1-alkene include 1-nonene, 1-decene, 1-undecene, 1-dodecene, 1-tridecene, 1-tetradecene, 1-hexadecene, 1-octadecene and the like. Examples of the organopolysiloxane having one reactive unsaturated group per molecule include a dimethylpolysiloxane capped at one molecular terminal with a vinyl group, a methylphenylpolysiloxane capped at one molecular terminal with a vinyl group, and the like.

The hydrosilylation reaction used to synthesize the sugar derivative-modified silicone or a composition including the same can be carried out in accordance with a publicly known method in the presence or absence of a solvent. Here, examples of the reaction solvent include alcohol-based solvents such as ethanol and isopropyl alcohol; aromatic hydrocarbon-based solvents such as toluene and xylene; ether-based solvents such as dioxane and THF; aliphatic hydrocarbon-based solvents such as n-hexane, cyclohexane, n-heptane, cycloheptane, and methylcyclohexane; chlorinated hydrocarbon-based organic solvents such as carbon tetrachloride; and various oil agents (silicone oil, hydrocarbon oil, ester oil, and the like) that can also be used as the oil agents described later.

The hydrosilylation reaction may be performed in the absence of a catalyst, but preferably is performed in the presence of a catalyst because the reaction can be carried out at a low temperature and in a shorter period of time. Examples of the catalyst include platinum, ruthenium, rhodium, palladium, osmium, iridium compounds, and the like, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. If a platinum catalyst is used, the usage quantity of the catalyst, as platinum metal, is approximately 0.0001 to 0.1 mass %, and preferably 0.0005 to 0.05 mass %, but is not particularly limited thereto.

A reaction temperature of the hydrosilylation reaction is typically from 30 to 120° C., and a reaction time is typically from 10 minutes to 24 hours and preferably from 1 to 10 hours.

The sugar derivative-modified silicone to which the present invention can be applied may be a liquid sugar derivative-modified crosslinked silicone. Preferably, the liquid sugar derivative-modified crosslinked silicone is obtained by reacting (A) organohydrogenpolysiloxane, (B) the sugar derivative group-containing organic compound that has one or more reactive unsaturated group per molecule, and (C) one or more types of organic compounds selected from a group consisting of (C1) an organic compound having a number of reactive unsaturated groups greater than one on average per molecule and (C2) an organic compound having one or more reactive unsaturated groups and one or more epoxy groups per molecule (however, the use of the component (B) is optional when the component (C) contains the sugar derivative group-containing organic group); and has a silicon-bonded sugar derivative group-containing organic group and a crosslinked structure containing a Si—C bond in a crosslinking part.

The (A) organohydrogenpolysiloxane is not particularly limited as long as it has silicon atom-bonded hydrogen atoms, but an organohydrogenpolysiloxane having more than one—preferably from 1.01 to 100, more preferably from 1.1 to 50, even more preferably from 1.2 to 25, and particularly preferably from 1.3 to 10—silicon-bonded hydrogen atoms in one molecule on average is preferable, and a straight-chain, branched, or reticulated organopolysiloxane may be used. The positions of the silicon-bonded hydrogen atoms in the organohydrogenpolysiloxane is not limited, and can be on the main chain or at the terminals. However, from the perspective of reducing crosslinking, it is preferable to position in the terminal. One type or two or more types of organohydrogenpolysiloxanes may be used as the component (A).

Examples of the component (A) include 1,1,3,3-tetramethyldisiloxane, 1,3,5,7-tetramethylcyclotetrasiloxane, methylhydrogenpolysiloxane capped at both molecular terminals with trimethylsiloxy groups, dimethylsiloxane-methylhydrogensiloxane copolymers capped at both molecular terminals with trimethylsiloxy groups, dimethylsiloxane capped at both molecular terminals with dimethylhydrogensiloxy groups, dimethylpolysiloxane capped at both molecular terminals with dimethylhydrogensiloxy groups, dimethylsiloxane-methylhydrogensiloxane copolymers capped at both molecular terminals with dimethylhydrogensiloxy groups, methylhydrogensiloxane-diphenylsiloxane copolymers capped at both molecular terminals with trimethylsiloxy groups, methylhydrogensiloxane-diphenylsiloxane-dimethylsiloxane copolymers capped at both molecular terminals with trimethylsiloxy groups, copolymers comprising $(CH_3)_2HSiO_{1/2}$ units and $SiO_{4/2}$ units, and copolymers comprising $(CH_3)_2HSiO_{1/2}$ units, $SiO_{4/2}$ units, and $(C_6H_5)SiO_{3/2}$ units.

Component (A) is preferably represented by average composition formula (11):

$$R^1_a H_b SiO_{(4-a-b)/2} \tag{11}$$

(in average composition formula (11), each $R^1$ is independently represented by monovalent organic groups, and $1.0 \leq a \leq 3.0$, and $0.001 \leq b \leq 1.5$).

Although the molecular structure of the (A) organohydrogenpolysiloxane is not limited, examples include straight-chain, partially branching straight-chain, branched-chain, cyclic, and dendric structures, and straight-chain is preferable. The molecular weight is not particularly limited, and products having a low molecular weight to products having a high molecular weight can be used. Specifically, the number-average molecular weight is preferably in a range of 100 to 1,000,000 and more preferably in a range of 300 to 500,000.

Examples of the organohydrogenpolysiloxane include organohydrogenpolysiloxane represented by the following structural formulae $$R^1_3SiO(R^1_2SiO)_v(R^1SiHO)_wSiR^1_3 \tag{i}$$

$$HR^1_2SiO(R^1_2SiO)_v(R^1SiHO)_zSiR^1_3 \tag{ii}$$

$$HR^1_2SiO(R^1_2SiO)_v(R^1SiHO)_zSiR^1_2H \tag{iii}$$

(in structural formulae (i) to (iii), $R^1$ is as described above, v is 0 or a positive integer, w is a positive integer, and z is 0 or a positive integer). These organohydrogenpolysiloxanes are straight-chain organohydrogenpolysiloxanes having a silicon-bonded hydrogen atom on (i) only the side chain, (ii) the side chain or one molecular terminal, or (iii) the side chain or both molecular terminals.

The monovalent organic group is not particularly limited but is preferably selected from the following (D1) to (D10):

(D1) a substituted or unsubstituted, straight-chain or branched monovalent hydrocarbon group having from 1 to 60 carbons;

(D2) a polyoxyalkylene group represented by $-R^{28}O(AO)_{z1}R^{29}$ (wherein, AO is an oxyalkylene group having from 2 to 4 carbons; $R^{28}$ is a substituted or unsubstituted, straight-chain or branched divalent hydrocarbon group having from 3 to 5 carbons; $R^{29}$ is a hydrogen atom, a substituted or unsubstituted, straight-chain or branched monovalent hydrocarbon group having from 1 to 24 carbons, or a substituted or unsubstituted, straight-chain or branched acyl group having from 2 to 24 carbons; and $z1=1$ to 100);

(D3) a substituted or unsubstituted, straight-chain or branched alkoxy group having from 1 to 30 carbons;

(D4) a hydroxyl group;

(D5) an ester group represented by $-R^{30}-COOR^{31}$ (wherein, $R^{30}$ is a substituted or unsubstituted, straight-chain or branched divalent hydrocarbon group having from 2 to 20 carbons, and $R^{31}$ is a substituted or unsubstituted, straight-chain or branched monovalent hydrocarbon group having from 1 to 30 carbons);

(D6) an ester group represented by $-R^{17}-OCOR^{18}$ (wherein, $R^{17}$ is a substituted or unsubstituted, straight-chain or branched divalent hydrocarbon group having from 2 to 20 carbons, and $R^{18}$ is a substituted or unsubstituted, straight-chain or branched monovalent hydrocarbon group having from 1 to 30 carbons); (D7) $L^1$ here, $L^1$ is a silylalkyl group having a siloxane dendron structure and represented by the following general formula (33) when $i=1$:

[Chemical Formula 25]

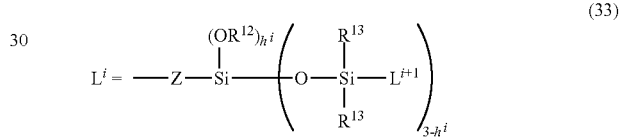

(In general formula (33), $R^{12}$ represents a substituted or unsubstituted, straight or branched monovalent hydrocarbon group having from 1 to 30 carbons; each $R^{13}$ independently represents an alkyl group or phenyl group having from 1 to 6 carbons, Z represents a divalent organic group, i represents a generation of the silylalkyl group represented by $L^i$ and is an integer of 1 to k when k is a number of generations that is a number of repetitions of the silylalkyl group, the number of generations k is an integer from 1 to 10; $L^{i+1}$ is the silylalkyl group when i is less than k, and $R^{13}$ when $i=k$; and $h^i$ is a number in a range of 0 to 3);

(D8) an alkyl group substituted by a chain polysiloxane structure and represented by the following general formula (44):

[Chemical Formula 26]

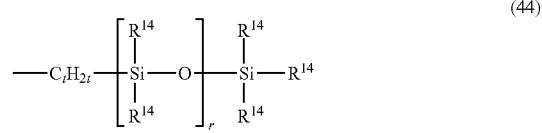

(In general formula (44), each $R^{14}$ is independently substituted or unsubstituted, straight-chain or branched monovalent hydrocarbon groups having from 1 to 30 carbons, hydroxyl groups, or hydrogen atoms, and at least one of the $R^{14}$ is the monovalent hydrocarbon group; t is a number in a range of 2 to 10; and r is a number in a range of 1 to 500);

(D9) an epoxy group represented by the following general formula (55):

[Chemical Formula 27]

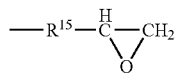
(55)

(In general formula (55), $R^{15}$ is a substituted or unsubstituted, straight-chain or branched divalent hydrocarbon group having from 2 to 20 carbons); and (D10) a cycloaliphatic epoxy group represented by the following general formula (66):

[Chemical Formula 28]

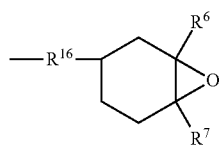
(66)

(In general formula (66), $R^{16}$ is a substituted or unsubstituted, straight-chain or branched divalent hydrocarbon group having from 2 to 20 carbons, and $R^6$ and $R^7$ are hydrogen atoms or the methyl group).

Examples of the substituted or unsubstituted, straight-chain or branched monovalent hydrocarbon group in (D1), (D2), and (D5) to (D8), include alkyl groups such as a methyl group, ethyl group, propyl group, butyl group, pentyl group, hexyl group, heptyl group, octyl group, and the like; cycloalkyl groups such as a cyclopentyl group, cyclohexyl group, and the like; alkenyl groups such as a vinyl group, allyl group, butenyl group, and the like; aryl groups such as a phenyl group, tolyl group, and the like; aralkyl groups such as a benzyl group; and groups wherein the hydrogen atoms bonded to the carbon atoms of these groups are substituted at least partially by fluorine or a similar halogen atom, or an organic group including an epoxy group, a glycidyl group, an acyl group, a carboxyl group, an amino group, a (meth) acryl group, a mercapto group, or the like. The monovalent hydrocarbon group is preferably a group other than an alkenyl group, and is particularly preferably a methyl group, an ethyl group, or a phenyl group.

The substituted or unsubstituted, straight-chain or branched divalent hydrocarbon groups in (D2), (D5), (D6), (D9), and (D10) are as described above.

Examples of the substituted or unsubstituted, straight-chain or branched alkoxy group in (D3) include lower alkoxy groups such as methoxy groups, ethoxy groups, isopropoxy groups, and butoxy groups and higher alkoxy groups such as lauryl alkoxy groups, myristyl alkoxy groups, palmityl alkoxy groups, oleyl alkoxy groups, stearyl alkoxy groups, and behenyl alkoxy groups.

Among the phenyl group or the alkyl group having from 1 to 6 carbons of (D7), examples of the alkyl group having from 1 to 6 carbons include straight, branched, or cyclic alkyl groups such as methyl, ethyl, n-propyl, i-propyl, n-butyl, i-butyl, s-butyl, pentyl, neopentyl, cyclopentyl, and hexyl groups.

In general formula (33), when i=k, $R^{13}$ is preferably a methyl group or a phenyl group. In particular, $R^{13}$ is preferably a methyl group when i=k.

From an industrial standpoint, the number of generations k is preferably an integer of 1 to 3, and more preferably is 1 or 2. In each of the number of generations, the group represented by $L^1$ is represented as follows. In the formulae, $R^{12}$, $R^{13}$, and Z are the same groups as described above.

When the number of generations is k=1, $L^1$ is represented by the following general formula (33-1).

[Chemical Formula 29]

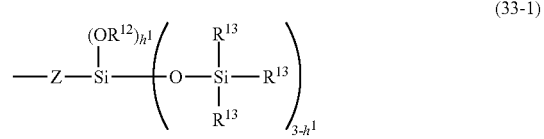
(33-1)

When the number of generations is k=2, $L^1$ is represented by the following general formula (33-2).

[Chemical Formula 30]

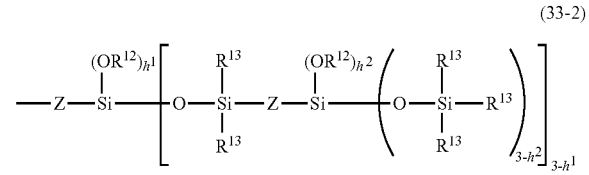
(33-2)

When the number of generations is k=3, $L^1$ is represented by the following general formula (33-3).

[Chemical Formula 31]

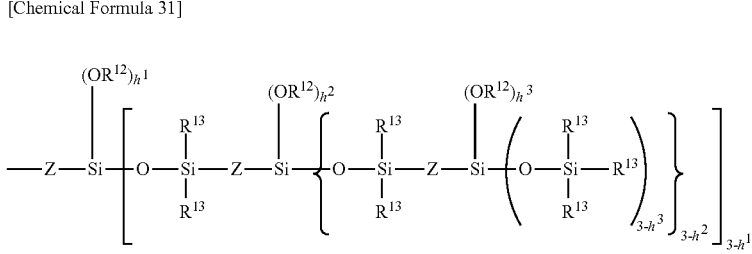
(33-3)

In the structures represented by the general formulae (33-1) to (33-3) when the number of generations is from 1 to 3, each of $h^1$, $h^2$ and $h^3$ is independently a number in a range of 0 to 3. These $h^i$ are preferably a number in a range of 0 to 1, and $h^i$ is, in particular, preferably 0.

In general formulae (33) and (33-1) to (33-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not limited to the functional groups described above. Preferably, each Z is independently a group selected from divalent organic groups represented by the following formula:

[Chemical Formula 32]

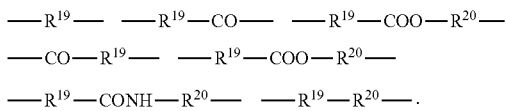

Of these, Z in $L^1$ is preferably a divalent organic group represented by general formula —$R^{19}$— that is introduced by a reaction between a silicon-bonded hydrogen atom and an alkenyl group. Likewise, Z is preferably a divalent organic group represented by general formula —$R^{19}$—COO—$R^{20}$— that is introduced by a reaction between a silicon-bonded hydrogen atom and an unsaturated carboxylic ester group. Meanwhile, in the silylalkyl group represented by $L^i$, in which the number of generations k is not less than 2, and $L^i$ is $L^2$ to $L^k$, Z is preferably an alkylene group having from 2 to 10 carbons is particularly preferably a group selected from an ethylene group, a propylene group, a methylethylene group, and a hexylene group, and most preferably is an ethylene group.

In the general formula described above, each $R^{19}$ is independently a substituted or unsubstituted straight or branched chain alkylene group or alkenylene group having from 2 to 22 carbons or an arylene group having from 6 to 22 carbons. More specifically, examples of $R^{19}$ include straight alkylene groups such as an ethylene group, a propylene group, a butylene group, and a hexylene group; and branched alkylene groups such as a methylmethylene group, a methylethylene group, a 1-methylpentylene group, and a 1,4-dimethylbutylene group. $R^{20}$ is preferably a group selected from an ethylene group, a propylene group, a methylethylene group, and a hexylene group.

In the general formula described above, $R^{20}$ is preferably a group selected from divalent organic groups expressed by the following formula.

[Chemical Formula 33]

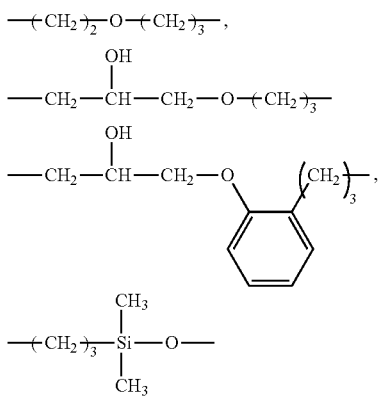

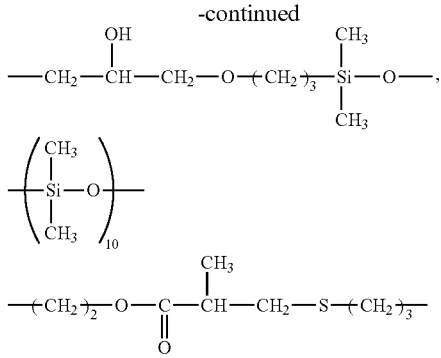

(B) the sugar derivative group-containing organic compound having the reactive unsaturated group is not particularly limited as long as there is at least one per molecule of the reactive unsaturated group and the sugar derivative group, the sugar derivative group may be derived from monosaccharides, disaccharides, or oligosaccharides, or may be derived from sugar alcohol groups, but is preferably a sugar alcohol monounsaturated ether compound represented by the following general formula (4'-1):

[Chemical Formula 34]

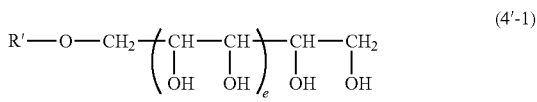

(4'-1)

(wherein, R' represents an unsaturated organic group, and e is 1 or 2, and preferably 1) or is preferably a sugar alcohol monounsaturated ether compound represented by the following general formula (4'-2):

[Chemical Formula 35]

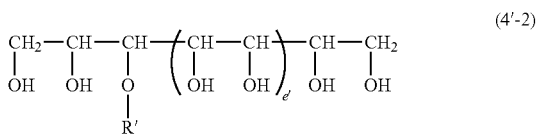

(4'-2)

(wherein, R' represents the unsaturated organic group, and e' is 0 or 1, and preferably 0).

The unsaturated organic group is not particularly limited as long as the unsaturated organic group has an unsaturated group, but is preferably a substituted or unsubstituted, straight or branched unsaturated hydrocarbon group having from 3 to 5 carbons. Examples of the unsaturated hydrocarbon group having from 3 to 5 carbons include alkenyl groups such as allyl groups, methallyl groups, and butenyl groups. An allyl group is preferable.

As the sugar alcohol monounsaturated ether compound, sugar alcohol monoallyl ethers are preferable, and more preferably xylitol monoallyl ether represented by structural formula: $CH_2=CH-CH_2-OCH_2[CH(OH)]_3CH_2OH$, or structural formula: $CH_2=CH-CH_2-OCH\{CH(OH)CH_2OH\}_2$ (hereinafter, referred to as "xylitol monoallyl ether"). The xylitol monoallyl ether can be synthesized using a publicly known method, and is also commercially available.

The xylitol monoallyl ether can be used without limitation in only one compound or a mixture of the compounds represented by structural formula: $CH_2=CH-CH_2-OCH_2[CH(OH)]_3CH_2OH$, or structural formula: $CH_2=CH-CH_2-OCH\{CH(OH)CH_2OH\}_2$. In particular, it is preferable that any of the xylitol monoallyl ethers represented by structural formula: $CH_2=CH-CH_2-OCH_2[CH(OH)]_3CH_2OH$, or structural formula: $CH_2=CH-CH_2-OCH\{CH(OH)CH_2OH\}_2$ are purified and used as a starting material, or xylitol monoallyl ether containing the xylitol monoallyl ethers represented by the structural formula: $CH_2=CH-CH_2-OCH_2[CH(OH)]_3CH_2OH$, and structural formula: $CH_2=CH-CH_2-OCH[CH(OH)CH_2OH]_2$ wherein the substance ratio between these xylitol monoallyl ethers is in a range of 5:5 to 10:0, is used as the starting material. In the latter case, xylitol monoallyl ethers with the substance ratio between a range of 8:2 to 10:0 is more preferable. In the case of 10:0, the starting material is a purified product comprising only xylitol monoallyl ether substantially represented by structural formula: $CH_2=CH-CH_2-OCH_2[CH(OH)]_3CH_2OH$.

(B) the sugar derivative group-containing organic compound having the reactive unsaturated group may become the hydrophilic impurities in the present invention.

There are no particular limitations regarding the structure of (C1) the organic compound having an average number of unsaturated bonds per molecule that is greater than 1 serving as the component (C) as long as the compound has more than 1—preferably from 1.01 to 10, more preferably from 1.2 to 8, even more preferably from 1.5 to 6, and particularly preferably from 2.0 to 4.5 unsaturated bonds and preferably carbon-carbon double bonds on average per molecule, and straight-chain, branched, or reticulated organic compounds may be used. An organopolysiloxane or an unsaturated aliphatic hydrocarbon is preferable as an organic compound. There are also no limitations regarding the position of the unsaturated bond on the organic compound and preferably the organopolysiloxane or the unsaturated aliphatic hydrocarbon, and the component may be positioned on the main chain or on a terminal. However, from the perspective of the ease of controlling the crosslinking density, it is preferable to use a compound of high purity having two unsaturated groups in the molecule, each of which is positioned at either terminal, for example.

An unsaturated bond is preferably present in an unsaturated aliphatic hydrocarbon group. The unsaturated aliphatic hydrocarbon group preferably has from 2 to 30 carbons and more preferably has from 2 to 20 carbons. Examples of the monovalent unsaturated aliphatic hydrocarbon group having from 2 to 30 carbons include straight-chain or branched alkenyl groups such as vinyl groups, 1-propenyl groups, allyl groups, isopropenyl groups, 1-butenyl groups, 2-butenyl groups, pentenyl groups, and hexenyl groups; cycloalkenyl groups such as cyclopentenyl groups and cyclohexenyl groups; cycloalkenylalkyl groups such as cyclopentenylethyl groups, cyclohexenylethyl groups, and cyclohexenylpropyl groups; and alkynyl groups such as ethynyl groups and propargyl groups. Alkenyl groups are preferred, and the vinyl group and hexenyl group are particularly preferred.

When the component (C1) is an organopolysiloxane, the unsaturated aliphatic hydrocarbon group containing an unsaturated bond is preferably bonded to a silicon atom. In addition, when the component (C1) is an organopolysiloxane, the group bonding to silicon atoms other than the unsaturated aliphatic hydrocarbon may be a substituted or unsubstituted monovalent hydrocarbon group or a monovalent organic group having a reactive functional group.

Substituted or unsubstituted monovalent hydrocarbon groups are typically substituted or unsubstituted, straight or branched monovalent saturated hydrocarbon groups having from 1 to 30 carbons, preferably from 1 to 10 carbons, and more preferably from 1 to 4 carbons, and substituted or unsubstituted monovalent aromatic hydrocarbon groups having from 6 to 30 carbons, and more preferably from 6 to 12 carbons. Moreover, component (C1) may contain, as a monovalent organic group, a hydroxyl group or an alkoxy group having from 1 to 12 carbons, such as a methoxy group, an ethoxy group, a propoxy group or a butoxy group.

Examples of the monovalent saturated hydrocarbon group having from 1 to 30 carbons include straight chain or branched chain alkyl groups such as methyl, ethyl, n-propyl, isopropyl, n-butyl, isobutyl, sec-butyl, tert-butyl, pentyl, hexyl, heptyl, octyl, nonyl, decyl, and the like; and cycloalkyl groups such as cyclopentyl, cyclohexyl, cycloheptyl, cyclooctyl, and the like.

Examples of the monovalent aromatic hydrocarbon group having from 6 to 30 carbons include aryl groups such as phenyl groups, tolyl groups, xylyl groups, mesityl groups, and the like. Of these, a phenyl group is preferable. Note that, in the present specification, "aromatic hydrocarbon group" also includes groups in which an aromatic hydrocarbon and a saturated aliphatic hydrocarbon are conjugated in addition to groups formed only from an aromatic hydrocarbon. Examples of groups in which an aromatic hydrocarbon and a saturated hydrocarbon are conjugated include aralkyl groups such as benzyl groups, phenethyl groups, and the like.

Hydrogen atoms in the above-mentioned monovalent hydrocarbon groups may be substituted by one or more substituted groups, and the substituted groups may be selected from the group consisting of, for example, a halogen atom (a fluorine atom, a chlorine atom, a bromine atom, or an iodine atom), a hydroxyl group, an amide group, an ester group, a carboxyl group and an isocyanate group. A monovalent saturated or aromatic hydrocarbon group having at least one of the above-mentioned substituted groups is preferred. Specifically, it is possible to use a 3,3,3-trifluoropropyl group, a 3-chloropropyl group, a 3-hydroxypropyl group, a 3-(2-hydroxyethoxy)propyl group, a 3-carboxypropyl group, a 10-carboxydecyl group, a 3-isocyanatopropyl group and the like.

Examples of monovalent organic groups having reactive functional groups include monovalent saturated or aromatic hydrocarbon groups having reactive functional groups selected from the group consisting of, for example, hydroxyl groups, mercapto groups, epoxy groups, amino groups, amide groups, ester groups, carboxyl groups and isocyanate groups. One or a plurality of reactive functional groups may exist in the monovalent organic group. $R^1$ is preferably a monosaturated or aromatic hydrocarbon group having at least one of the reactive functional groups described above. Specific examples of the reactive functional group include 3-hydroxypropyl groups, 3-(2-hydroxyethoxy)propyl groups, 3-mercaptopropyl groups, 2,3-epoxypropyl groups, 3,4-epoxybutyl groups, 4,5-epoxypentyl groups, 2-glycidoxyethyl groups, 3-glycidoxypropyl groups, 4-glycidoxybutyl groups, 2-(3,4-epoxycyclohexyl) ethyl groups, 3-(3,4-epoxycyclohexyl)propyl groups, aminopropyl groups, N-methylaminopropyl groups, N-butylaminopropyl groups, N,N-dibutylaminopropyl groups, 3-(2-aminoethoxy)propyl groups, 3-(2-aminoethylamino)propyl groups, 3-carboxypropyl groups, 10-carboxydecyl groups, 3-isocyanate propyl groups, and the like.

A straight-chain, cyclic, or branched polysiloxane is preferable as the component (C1). A straight-chain component (C1) is preferably a polymer having a diorganosiloxane unit and a triorganosiloxy unit, examples of which include dimethylpolysiloxanes capped at both molecular terminals with dimethylvinylsiloxy groups, copolymers of dimethylsiloxane and methylphenylsiloxane capped at both molecular terminals with dimethylvinylsiloxy groups, copolymers of dimethylsiloxane and methylvinylsiloxane capped at both molecular terminals with dimethylvinylsiloxy groups, copolymers of dimethylsiloxane and methylvinylsiloxane capped at both molecular terminals with trimethylsiloxy groups, copolymers of dimethylsiloxane, methylvinylsiloxane and methylphenylsiloxane capped at both molecular terminals with trimethylsiloxy groups, copolymers of dimethylsiloxane and methylvinylsiloxane capped at both molecular terminals with silanol groups, polymers in which some of the methyl groups in these polymers are substituted by alkyl groups other than methyl groups, such as ethyl groups or propyl groups, or halogenated alkyl groups such as 3,3,3-trifluoropropyl groups, and mixtures of two or more of these polymers, with straight-chain diorganopolysiloxanes having unsaturated aliphatic hydrocarbon groups, and especially alkenyl groups, at both molecular terminals only being particularly preferred.

It is particularly preferable for a branched chain polysiloxane of component (C1) to be a polymer that contains a diorganosiloxane unit, an organosilsesquioxane unit and a triorganosiloxy unit. Silicon-bonded organic groups in these units are preferably monovalent hydrocarbon groups including alkyl groups such as methyl groups, ethyl groups and propyl groups; alkenyl groups such as vinyl groups, allyl groups, butenyl groups and hexenyl groups; aryl groups such as phenyl groups and tolyl groups; and halogenated alkyl groups such as 3,3,3-trifluoropropyl groups, and the like, and may contain extremely small quantities of hydroxyl groups and alkoxy groups such as methoxy groups, but at least two silicon-bonded organic groups in this polymer must be unsaturated aliphatic hydrocarbon groups, and especially alkenyl groups. In addition, the proportions of these units are not limited, but in this polymer, it is preferable for diorganosiloxane units to be in an amount in the range of 80.00 to 99.65 mol % and organosilsesquioxane units to be in an amount in the range of 0.10 to 10.00 mol %, with the balance comprising triorganosiloxy units.

Examples of the component (C1) that is a cyclic polysiloxane include methylvinylcyclosiloxane, methylhexenylcyclosiloxane, and the like.

Examples of the component (C1) include (C1-5) unsaturated group-containing silicone compounds represented by the average composition formula (22):

(In formula (22), each $R^{32}$ may be independent, but represent a monovalent organic group different from $R^{33}$, each $R^{33}$ is independently monovalent unsaturated aliphatic hydrocarbon groups having from 2 to 30 carbon atoms, $1.0 \leq p \leq 2.5$, and $0.001 \leq q \leq 1.5$). The monovalent unsaturated aliphatic hydrocarbon group having from 2 to 30 carbons is as described above.

In the average composition formula (22), the monovalent organic group represented by $R^{32}$ is not particularly limited, but is preferably selected from the following (E1) to (E6):

(E1) a substituted or unsubstituted, straight-chain or branched monovalent hydrocarbon group having from 1 to 60 carbons (excluding monovalent hydrocarbon groups having from 2 to 20 carbons and an aliphatic unsaturated group);

(E2) a hydroxyl group; (E3) an ester group represented by $-R^{30}-COOR^{31}$ (wherein, $R^{30}$ and $R^{31}$ are as defined above);

(E4) an ester group represented by $-R^{17}-OCOR^{18}$ (wherein, $R^{17}$ and $R^{18}$ are as defined above);

(E5) an amide group represented by $-R^{21}-NR^{22}COR^{23}$ (wherein, $R^{21}$ is a substituted or unsubstituted, straight-chain or branched divalent hydrocarbon group having from 2 to 20 carbons, $R^{22}$ is a hydrogen atom, or a substituted or unsubstituted, straight-chain or branched monovalent hydrocarbon group having from 1 to 20 carbons, and $R^{23}$ is a substituted or unsubstituted, straight-chain or branched monovalent hydrocarbon group having from 1 to 30 carbons); and (E6) an amide group represented by $-R^{24}-CONR^{25}R^{26}$ (wherein, $R^{24}$ is a substituted or unsubstituted, straight-chain or branched divalent hydrocarbon group having from 2 to 20 carbons, and each of $R^{25}$ and $R^{26}$ is independently a hydrogen atom or a substituted or unsubstituted, straight-chain or branched monovalent hydrocarbon group having from 1 to 20 carbons). The definitions, types, and the like of the substituted or unsubstituted, straight-chain or branched monovalent hydrocarbon groups or divalent hydrocarbon groups are as described above.

On the other hand, the component (C1) may be an unsaturated aliphatic hydrocarbon. Examples of unsaturated aliphatic hydrocarbons include various dienes, diynes, enynes, and similar products having two or more unsaturated bonds. In view of crosslinking, dienes, diynes, and enynes are preferable. Dienes, diynes, and enynes are compounds having a structure in which at least two unsaturated bonds are separated by one or more, and preferably two or more single bonds in a molecule. The unsaturated aliphatic hydrocarbon group may be present at the terminal of the molecular chain, or as a pendant group in the molecular chain.

Examples of unsaturated aliphatic hydrocarbons serving as the component (C1) include α,ω-unsaturated alkenes and alkynes having from 2 to 30 carbons. Examples of the component (C1) include (C1-1) an α,ω-diene represented by general formula (22-1):

(in general formula (22-1), $1 \leq x \leq 20$), (C1-2) an α,ω-diyne represented by general formula (22-2):

(in general formula (22-2), $1 \leq x \leq 20$), (C1-3) an α,ω-eneyne represented by general formula (22-3):

(in general formula (22-3), $1 \leq x \leq 20$), (C1-4) a bis-alkenyl polyether compound represented by general formula (22-4):

(in general formula (22-4), $2 \leq m \leq 20$, $2 \leq n \leq 4$, y is the total value of the repeating number of an oxyethylene unit, an oxypropylene unit, and an oxybutylene unit, and $1 \leq y \leq 180$).

Specific examples of unsaturated aliphatic hydrocarbons serving as the component (C1) include 1,4-pentadiene, 1,5-hexadiene, 1,6-heptadiene, 1,7-octadiene, 1,8-nonadiene, 1,9-decadiene, 1,11-dodecadiene, 1,13-tetradecadiene, 1,19-eicosadiene, 1,3-butadiene, 1,5-hexadiyne, and 1-hexene-5-yne.

The component (C1) may be a single component, but may also be a mixture of two or more components having different structures. That is, the component (C1) may be a mixture of one or more types of organopolysiloxanes and one or more types of unsaturated aliphatic hydrocarbons. Therefore, "having a number of unsaturated bonds greater than 1 on average" means having more than one unsaturated bond per molecule on average when two or more types of organopolysiloxanes and/or unsaturated aliphatic hydrocarbons are used.

The (C2) organic compound having at least one unsaturated bond and at least one epoxy group in the molecule serving as the component (C) is not structurally limited as long as the compound has a total of two or more—preferably from 2 to 10, more preferably from 2 to 7, even more preferably from 2 to 5, and particularly preferably from 2 to 4—unsaturated bonds and epoxy groups in the molecule, and straight-chain, branched, or reticulated organic compounds can be used. An organopolysiloxane or an unsaturated aliphatic hydrocarbon is preferable as an organic compound. There are also no limitations regarding the position of the unsaturated bond on the organic compound, preferably the organopolysiloxane or the unsaturated aliphatic hydrocarbon, and the component may be positioned on the main chain or on a terminal. However, from the perspective of the ease of controlling the crosslinking density, it is preferable to use a compound of high purity in which the total of unsaturated groups and epoxy groups in the molecule is two.

An unsaturated bond is preferably present in an unsaturated aliphatic hydrocarbon group. Examples of unsaturated aliphatic hydrocarbon groups may be as described above.

When the component (C2) is an organopolysiloxane, the unsaturated aliphatic hydrocarbon group containing an unsaturated bond and/or the epoxy group is preferably bonded to a silicon atom. In addition, when the component (C2) is an organopolysiloxane, the group bonding to silicon atoms other than the unsaturated aliphatic hydrocarbon or the epoxy group may be a substituted or unsubstituted monovalent hydrocarbon group or a monovalent organic group having a reactive functional group as described above.

The component (C2) is preferably an epoxy group-containing unsaturated aliphatic hydrocarbon having at least one epoxy group. Examples of the unsaturated aliphatic hydrocarbon include compounds having the unsaturated aliphatic hydrocarbon groups described above. A compound having a monovalent unsaturated aliphatic hydrocarbon group is preferable.

Examples of the component (C2) include (C2-1) an unsaturated epoxy compound represented by the general formula (22-6):

[Chemical Formula 36]

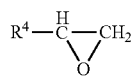

(22-6)

(in general formula (22-6), $R^4$ has one unsaturated bond and is a substituted or unsubstituted, straight-chain or branched monovalent hydrocarbon group having from 2 to 20 carbons), (C2-2) an unsaturated group-containing alicyclic epoxy compound represented by the general formula (22-7):

[Chemical Formula 37]

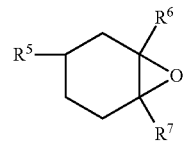

(22-7)

(in general formula (22-7), $R^5$ has one unsaturated bond and is a substituted or unsubstituted, straight-chain or branched monovalent hydrocarbon group having from 2 to 20 carbons, $R^6$ represents hydrogen atoms or the methyl group, and $R^7$ represents hydrogen atoms or the methyl group). The definitions, types, and the like of the unsaturated bonds in the general formulae above and the substituted or unsubstituted, straight-chain or branched monovalent hydrocarbon groups are as described above.

Specific epoxy group-containing unsaturated aliphatic hydrocarbons serving as the component (C2) include an allylglycidylether, methallylglycidylether, 1-methyl-4-isopropenylcyclohexene oxide, 1,4-dimethylcyclohexene oxide, 4-vinylcyclohexene oxide, vinylnorbornene monooxide, dicyclopentadiene monooxide, butadiene monooxide, 1,2-epoxy-5-hexene, 1,2-epoxy-9-decene, and 2,6-dimethyl-2,3-epoxy-7-octene. Among these, 4-vinyl cyclohexane oxide is preferable. Examples of the unsaturated aliphatic hydrocarbons having a cyclic structure include dicyclopentadiene, divinylbenzene, cyclohexadiene, cyclooctadiene, cyclopentadiene, and the like.

The component (C2) may be a single component, but may also be a mixture of two or more components having different structures.

The reaction for producing the sugar derivative-modified crosslinked silicone described above can be performed in accordance with a publicly known method in the presence or absence of a reaction solvent. The reaction between the unsaturated group and the Si—H group is a hydrosilylation reaction. In addition, when crosslinking is performed using an epoxide of (C2) the organic compound having one or more reactive unsaturated groups and one or more epoxy groups in the molecule, bonding caused by the reaction of the unsaturated group and the Si—H group and ether bond generation caused by the self-ring-opening polymerization of the epoxy groups (cationic polymerization reaction that occurs in the presence of a Si—H group and a platinum catalyst) both occur, resulting in crosslinking. In order to accelerate this reaction, irradiation using high energy beams such as ultraviolet light can be applied, or a common cation polymerization catalyst can be further added.

The reaction solvent is not particularly limited as long as the solvent is non-reactive, and examples thereof include alcohol-based solvents such as ethanol and isopropyl alcohol; aromatic hydrocarbon-based solvents such as toluene and xylene; ether-based solvents such as dioxane and THF; aliphatic hydrocarbon-based solvents such as n-hexane, cyclohexane, n-heptane, cycloheptane, and methylcyclohexane; and chlorinated hydrocarbon-based organic solvents such as carbon tetrachloride. An oil agent described below may also be used as a reaction solvent. When an oil agent is used as a reaction solvent, it is possible to directly obtain a composition consisting of an oil agent and a liquid sugar derivative-modified silicone having a silicon-bonded sugar derivative group-containing organic group and having a crosslinked structure containing a carbon-silicon bond in a crosslinking part after the crosslinking reaction.

It is possible to perform the hydrosilylation reaction as described above.

The component (A) is crosslinked by the component (C) as a result of the hydrosilylation reaction or the cationic polymerization reaction of the epoxy groups, and the polysiloxane chains derived from the component (A) are linked by the crosslinking portion having a carbon-silicon bond derived from the component (C). Component (A) is provided with the sugar derivative group-containing organic group derived from component (B). By doing this, it is possible to obtain the sugar derivative-modified crosslinked silicone having the crosslinked structure.

The sugar derivative-modified crosslinked silicone having the crosslinked structure has essentially a linked structure formed by the crosslinking part containing the carbon-silicon bond derived from component (C), but may also have a portion crosslinked by the Si—O—C bond. This is because when the structure has a condensation-reactable functional group such as a silanol group or an alkoxy group in the components (A) to (C), links can not only be formed between polysiloxane chains but can also be formed intermittently as a result of a partial reaction between the hydroxyl groups in the sugar derivative group derived from the component (B) and the Si—H groups of (A) when the crosslinking conditions are severe.

In the production of the sugar derivative-modified crosslinked silicone having the crosslinked structure, the component (C) may be further reacted with the component (A) after a reaction between the component (A) and the component (B), or the component (B) may be further reacted with the component (A) after a reaction between the component (A) and the component (C).

When the component (C) is further reacted with the component (A) after the reaction between the component (A) and the component (B), the average value of the number of silicon-bonded hydrogen atoms per molecule of the component (A) reacting with the reactive unsaturated groups of the component (C) is preferably at least 1.0. That is, the number of silicon-bonded hydrogen atoms per molecule of the component (A) which constitute the crosslinking portion and react with the reactive unsaturated groups in the component (C) is, on average, at least 1.0, preferably within a range of 0.2 to 1.5, and particularly preferably within a range of 0.6 to 1.3.

In the production of the sugar derivative-modified crosslinked silicone having the crosslinked structure, in addition to component (A), component (B), and component (C), (Q) an organic compound (however, excluding component (C2)) having one reactive unsaturated group per molecule may be further caused to react. One type of component (Q) may be used, or two or more types of components (Q) may be used. It is possible to sequentially implement the reaction preferably in the presence of a hydrosilylation reaction catalyst. The definition, type, and the like of the reactive unsaturated group in component (Q) is as described above.

For example, when component (C) is further caused to react with component (A) after the reaction of component (A) and component (B), component (Q) may be caused to react with component (A) prior to the reaction between component (A) and component (B), component (Q) may be caused to react with component (A) after the reaction between component (A) and component (B), or component (Q) may be further caused to react with component (A) after the reaction of the component (C).

For example, when component (B) is further caused to react with component (A) after the reaction of component (A) and component (C), component (Q) may be caused to react with component (A) prior to the reaction between component (A) and component (C), component (Q) may be caused to react with component (A) after the reaction between component (A) and component (C), or component (Q) may be further caused to react with component (A) after the reaction of the component (B).

Examples of component (Q) include (Q1) a siloxane dendron compound having one reactive unsaturated group per molecule, (Q2) a hydrocarbon compound having one reactive unsaturated group per molecule or chain organopolysiloxane having one reactive unsaturated group per molecule, and the like.

The compound in general formula (3') described above is preferable as (Q1) the siloxane dendron compound having one reactive unsaturated group per molecule.

The compound in general formula (2') described above or in general formula (2'-1) described above is preferable as (Q2) the hydrocarbon compound having one reactive unsaturated group per molecule or chain organopolysiloxane having one reactive unsaturated group per molecule.

Examples of (Q2) the hydrocarbon compound having one reactive unsaturated group per molecule include a compound similar to (e) the hydrocarbon compound having one reactive unsaturated group per molecule.

A water addition step with the object of desired transparency and the like may be included in production of the transparent or translucent liquid sugar derivative-modified silicone or a composition thereof according to the present invention. However, it is desirable to not add water during production from the perspective of obtaining a high purity product.

Liquid Oil Solution Addition Step

The production method of the liquid high purity sugar derivative-modified silicone of the present invention or the composition thereof may further include, before and/or after and/or simultaneously with the purification-increasing treatment step, a liquid oil solution addition step of adding a liquid oil solution to the liquid sugar derivative-modified silicone or composition thereof. Here, "liquid" has the same meaning as previously described.

The liquid oil solution preferably has affinity with the liquid sugar derivative-modified silicone. The liquid oil agent is preferably one or more oil agents selected from silicone oils, non-polar organic compounds, and low-polarity to high-polarity organic compounds that are liquid at 5 to 100° C., and the non-polar organic compounds and low-polarity to high-polarity organic compounds are preferably hydrocarbon oils, fatty acid ester oils, and liquid fatty acid triglycerides. These are components that are particularly widely used as base materials for cosmetic compositions, but it is possible to additionally use one or more types of compound selected from among publicly known vegetable oils and fats, animal oils and fats, higher alcohols, fatty acid triglycerides, artificial sebum and fluorine-based oils as well as these oil agents. The sugar derivative-modified silicone or a composition including the same exhibit excellent compatibility and dispersibility with respect to the non-silicone oil agents when the sugar derivative-modified silicone has a long chain alkyl group. Therefore, hydrocarbon oil, fatty acid ester oil, and the like can be stably blended into a cosmetic composition, and the moisture retaining property of the non-silicone oil agents can be utilized. Therefore, a composition including the above sugar derivative-modified silicone modified by a sugar derivative can improve the blending stability of these non-silicone-based oil agents in cosmetic compositions.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (e.g. a hydrocarbon oil, a fatty acid ester oil, or the like), the cosmetic composition comprising a non silicone-based oil agent along with a silicone oil is advantageous in that a smoother, more luxurious tactile sensation is imparted.

The oil agents are the same as those disclosed by the present applicant in paragraphs [0141] to [0150] and the like of Patent Document 28 (Japanese Unexamined Patent Application Publication No. 2012-246446A).

The added amount of liquid oil solution in the liquid oil solution addition step is not particularly limited but may be from 5 to 1000 parts by mass, preferably from 10 to 500 parts by weight, and even more preferably from 50 to 200 parts by weight per 100 parts by mass of the liquid sugar derivative-modified silicone or composition thereof.

In the liquid oil solution addition step, the liquid sugar derivative-modified silicone or composition thereof and the liquid oil solution are preferably mixed to homogenize. Mixing to homogenize is preferably performed using mechanical power. For example, mixing can be performed with a paddle mixer, a propeller mixer, or in a reaction vessel or a container equipped with mixing blades, and an emulsifier, a kneader, or the like may also be used as necessary. Furthermore, mixing to homogenize does not necessarily have to be performed at room temperature, and the temperature may be increased or decreased in accordance with the composition, fluidity, and the like. It is normally preferable to perform mixing to homogenize around a range of 0 to 70° C.

Unlike conventional polyether-modified silicone and the like, the sugar derivative-modified silicone or a composition thereof according to the present invention is stable, inherently having little tendency to degrade due to oxidation by oxygen in the air. Therefore, there is no need for the operation of increasing oxidative stability by blending antioxidants such as phenols, hydroquinones, benzoquinones, aromatic amines, or vitamins in order to prevent oxidative degradation. However, stability improves further when such antioxidants, for example, BHT (2,6-di-t-butyl-p-cresol), vitamin E, and the like are added. In this case, the added amount of the antioxidant that is used is in a range (by weight (mass)) from 10 to 1,000 ppm, and preferably from 50 to 500 ppm, of the sugar derivative-modified silicone.

The visible light transmittance of the liquid high purity sugar derivative-modified silicone composition after the liquid oil solution addition step is preferably not less than 50%, more preferably not less than 70%, and even more preferably not less than 80%. Light of wavelength from 360 to 830 nm is preferred as the visible light, and light of wavelength from 400 to 760 nm is more preferred. For example, light of wavelength 750 nm may be used. An optical path length of 1 to 30 mm is preferred for transmittance measurement, and an optical path length of 5 to 20 mm is more preferred. For example, the transmittance measurement may be performed with an optical path length of 10 mm. Particularly when measured with an optical path length of 10 mm using light of wavelength 750 nm, light transmittance is not less than 50%, more preferably not less than 70%, and even more preferably not less than 80%.

The content of sugar derivative-modified silicone in the liquid high purity sugar derivative-modified silicone composition after the liquid oil solution addition step is not particularly limited, but is preferably from 10 to 99 wt. %, more preferably from 25 to 90 wt. %, and even more preferably from 50 to 80 wt. %, based on the total weight of the composition.

Acidizing and Odor Reduction of Sugar Derivative-Modified Silicone or Composition Thereof In the production method of the sugar derivative-modified silicone of the present invention or the composition thereof, the mixture, or the sugar derivative-modified silicone or the composition thereof (hereinafter, simply referred to as "the sugar derivative-modified silicone or the composition thereof") are preferably treated using an acidic substance, and odor-causing substances and a low boiling point component generated by the acidic substance treatment are removed by heating and/or depressurization. In this case, it is possible to obtain a higher quality sugar derivative-modified silicone or a composition thereof. It is possible to implement the treatment in the presence of a non-polar solvent and/or a polar solvent and/or water, but the acidic substance is preferably used by dissolving or dispersing in the polar solvent such as water, and it is more preferable to provide the treatment in a form including an acidic aqueous solution. As above, carrying out the acidizing step prior to the purification-increasing treatment of the present invention is preferable in order to achieve a further superior purification increase. Comprehensively considering rationality, cost, and obtained effects of the production process, it is best to follow the steps in order of "synthesis of a sugar derivative-modified silicone"->"acidizing and odor reduction"->"purification-increasing treatment". However, it is possible to skip the acidizing step when there is a low need for acidizing such as when the synthesis step is other than the hydrosilylation reaction. The "liquid oil solution addition step" described above may be implemented at a timing prior to or after the three basic steps.

Any material can be selected as the acidic substance contained in the acidic aqueous solution, but it is optimal to use one or more types of acidic inorganic salts which are solids at 25° C., are water-soluble, and have an aqueous solution pH of 4 or less at 25° C. when 50 g is dissolved in 1 L of ion exchanged water.

Treatment using the acidic aqueous solution can be most preferably implemented when the liquid sugar derivative-modified silicone is synthesized by a hydrosilylation reaction, and can be preferably implemented with the liquid sugar derivative-modified silicone being the liquid sugar derivative-modified crosslinked silicone. Here, for simplicity, the case of a liquid sugar derivative-modified silicone which does not includes the crosslinked structure and is synthesized by a hydrosilylation reaction will be described as an example of acidizing and an odor reducing method for a sugar derivative-modified silicone or a mixture containing the same.

Acidizing preferably includes the steps of:

[V] synthesizing a sugar derivative-modified silicone or a reaction mixture containing the same as a main component by subjecting (ax) a sugar derivative having a carbon-carbon double bond at the terminal of molecular chain and (bx) organohydrogenpolysiloxane to the hydrosilylation reaction; and

[W] treating the sugar derivative-modified silicone or the reaction mixture including the same as the main component, in the presence of (cx) one or more acidic inorganic salt that is solid at 25° C., is water-soluble, and has a pH of 4 or less at 25° C. in an aqueous solution when 50 g is dissolved in 1 L of ion exchanged water, simultaneously with the synthesis step [V] or after the synthesis step [V]. In addition, because a treatment step that uses the acidic inorganic salt involves the generation of odor-causing substances it is more preferable to include a step of removing odor-causing substances by heating or depressurizing after step [W], from the perspective of odor reduction effectiveness.

For example, in step (V), when the above-described hydrosilylation reaction is performed using (ax) a sugar derivative such as (poly)sugar monoallyl ether and (bx) a straight-chain organohydrogenpolysiloxane represented by structural formula (1-1A) in amounts so that there is an excessive amount of the substance of component (ax) with respect to the silicon-bonded hydrogen atoms in component (bx), the sugar derivative-modified silicone represented by structural formula (1-1) is synthesized, and a crude product of a reaction mixture containing the sugar derivative-modified silicone and unreacted component (ax) and containing the sugar derivative-modified silicone as a main component is obtained.

Step (W) is a step for reducing the odors of the sugar derivative-modified silicone or the composition thereof highly effectively and effectively suppressing the generation of odors over time by hydrolyzing the crude product using specific acidic inorganic salts, with practically no breakage of the silicon-oxygen bonds forming the main chain of polysiloxane or the carbon-oxygen bonds of side chain portions.

Process (W) specifically removes odor-causing substances from the crude product of the reaction mixture containing the sugar derivative-modified silicone as a main component by using hydrolysis, and it is characterized by performing treatment in the presence of (cx) one or more acidic inorganic salt that is solid at 25° C., is water-soluble, and has a pH of 4 or less at 25° C. in an aqueous solution when 50 g is dissolved in 1 L of ion exchanged water. The pH value of the sample aqueous solution can be measured using a pH meter that uses a glass electrode at room temperature (25° C.), and in detail, it is possible to use "HM-10P" manufactured by Toa Denpa Kogyo Co., Ltd.

The acidic inorganic salt serving as a component (cx) needs to be a solid at 25° C., needs to be water-soluble, and the aqueous solution needs to have a pH of 4 or less when 50 g of the acidic inorganic salt is dissolved in 1 L of ion exchanged water. The pH is preferably 3.5 or less and particularly preferably 2.0 or less. By using such a water-soluble acidic inorganic salt for hydrolysis treatment of the sugar derivative-modified silicone or the composition thereof, it is possible to reduce odors of the sugar derivative-modified silicone or the composition thereof highly effectively and effectively suppress odorization over time with almost no breakage of C—O bonds or Si—O bonds.

Examples that can be used as the acidic inorganic salt include acidic inorganic salts in which at least a monovalent hydrogen atom of the inorganic acid that is at least divalent is neutralized by a base. Examples of the inorganic acid that is at least divalent include sulfuric acid, sulfurous acid, and the like. Examples of the base include an alkali metal, ammonia, and the like.

More specifically, the component (cx) is preferably at least one type of acidic inorganic salt comprising a hydrogensulfate ion ($HSO_4-$) or a hydrogensulfite ion ($HSO_3-$) and a monovalent cation ($M^+$). Examples of the monovalent cation ($M^+$) include alkali metal ions or an ammonium ion. Particularly, the monovalent cation is preferably at least one type selected from the group consisting of a sodium ion, a potassium ion, and an ammonium ion. Additionally, one type of the acidic inorganic salt may be used alone or two or more types of acidic inorganic salt may be used. Furthermore, the acidic inorganic salt can be easily removed via filtration because the acidic inorganic salt is solid at room temperature (25° C.). Additionally, because it is water soluble, the acidic inorganic salt can be easily rinsed off using water, even in the cleaning step after production.

Meanwhile, in hydrolysis treatment based on an acetic acid salt, phosphoric acid salt, and the like that does not satisfy the conditions of the component (cx), it is not possible to sufficiently reduce the odor of the sugar derivative-modified silicone and the composition thereof after hydrolysis. Meanwhile, in hydrolysis treatment based on a strong acid such as hydrochloric acid and the like, and in hydrolysis treatment based on a publicly known solid acid of zirconium sulfate and the like, the odor can be reduced by a certain amount, but C—O bonds and Si—O bonds of the sugar derivative-modified silicone tend to break at the time of hydrolysis.

Specific examples of the acidic inorganic salt serving as the component (cx) are lithium hydrogensulfate, sodium hydrogensulfate, potassium hydrogensulfate, rubidium hydrogensulfate, cesium hydrogensulfate, ammonium hydrogensulfate, sodium hydrogensulfite, or hydrates thereof. The pH of aqueous solutions in which 50 g of the acidic inorganic salt is dissolved in 1 L of ion exchanged water is as shown in table below. From the perspective of the technical benefit of reducing odor, at least one type of acidic inorganic salt selected from the group consisting of sodium hydrogensulfate, potassium hydrogensulfate, and ammonium hydrogensulfate is most preferably used as the water soluble acidic inorganic salt having a pH of 2.0 or less.

TABLE 1

| Acidic inorganic salt | pH (50 g/L) |
| --- | --- |
| Sodium hydrogensulfate | 1.5 or less |
| Potassium hydrogensulfate | 2.0 or less |
| Ammonium hydrogensulfate | 1.5 or less |
| Sodium hydrogensulfite | 3.5 |

For example, treatment in the presence of an acidic inorganic salt refers to (1) decomposition treatment involving adding and stirring the above-described acidic inorganic salt into the reaction system (for example, a reaction vessel such as a flask) of the reaction mixture containing the sugar derivative-modified silicone synthesized by a hydrosilylation reaction as a main component, and (2) hydrolysis treatment or the like involving adding and stirring an acidic inorganic salt and water or an acidic inorganic salt, water, and a hydrophilic solvent. The treatment step that uses the acidic inorganic salt is preferably carried out in the presence of at least one of water and a hydrophilic solvent.

A particularly preferable hydrolysis treatment is a hydrolysis treatment whereby, after the step [V], at least an acidic inorganic salt and water are added to a reaction system containing a crude product of the reaction mixture containing the sugar derivative-modified silicone as a main component, and depending on the case, another hydrophilic solvent is further added with the objective of increasing the treatment efficiency by improving compatibility, and the solution is further stirred using a mechanical force. The hydrolysis treatment can be carried out at any temperature and treatment time, and the hydrolysis treatment is preferably carried out at a temperature from 0 to 200° C. and more preferably from 50 to 100° C. for a reaction time of from 0.1 to 24 hours and more preferably from approximately 0.5 to 10 hours. The amount of the acidic inorganic salt that is used can be selected appropriately in accordance with the treatment apparatus and the treatment time. However, the amount is preferably within a range of from 50 to 10,000 ppm and more preferably within a range of from 100 to 5,000 ppm with respect to the reaction mixture containing the sugar derivative-modified silicone as a main component.

After the acidizing described above, it is preferable to include a stripping step in which low-boiling-point components (propionaldehyde and the like), which are odor-causing substances, are removed. In addition, after stripping, it is possible to hydrolyze more of the propenyl ether group-containing sugar derivative or the like by treating again in the presence of an acidic inorganic salt, and propionaldehyde and the like, which are odor-causing substances, can be removed. At this time, there is an advantage that, because acidic inorganic salt remains, an acidic inorganic salt need not be newly added. Therefore, it is only necessary to add a hydrophilic solvent, typified by water. That is, the aforementioned step [W] and the stripping step can be repeated two times or more, to increase the degree of odor reduction, or the like.

Furthermore, the "materials with a low boiling point" which are distilled off by the stripping step, include not only propionaldehyde which is an odor-causing substance, but also the reaction solvents used in the hydrosilylation reaction (step [V]), the water used in the odor reduction treatment step, hydrophilic solvents, and the like.

The stripping step (removal of low-boiling-point substances) may be performed on the crude product of the reaction mixture containing the sugar derivative-modified silicone as a main component as the step prior to step [W], or may be performed on the reaction mixture containing the sugar derivative-modified silicone as a main component as the step following step [W]. In addition, the stripping step may be performed as the step prior to and the step after step [W]. The stripping step is preferably performed after the above-described step [W], to remove propionaldehyde, which is an odor-causing substance generated by the hydrolysis reaction.

As the removal method, stripping under normal pressure or under reduced pressure is preferable, and stripping at a temperature of 120° C. or lower is preferable. In order to effectively perform the stripping, the stripping is preferably performed under reduced pressure or, for example, performed under a nitrogen gas or similar inert gas stream. A specific example of the operation for removing low-boiling-point matter is one in which a crude product of the reaction mixture containing the sugar derivative-modified silicone containing the low-boiling-point matter as a main component is placed in a flask having a refluxing cooler, a nitrogen injection port, or the like; and, while supplying nitrogen gas, the internal pressure is reduced, and the internal temperature is increased and the pressure and temperature are maintained so as to be constant. Thus, the light matter is removed. Here, typically, a pressure reduction parameter is from 0.1 to 10.0 KPa, a heating temperature is from 40 to 120° C., and a treatment time is from 10 minutes to 24 hours.

Furthermore, after the acidizing step, a basic substance may be used to neutralize the reaction mixture containing the sugar derivative-modified silicone as a main component. Examples of the basic substance include inorganic bases such as sodium hydroxide, potassium hydroxide, calcium hydroxide, barium hydroxide, ammonia water, and sodium hydrogen carbonate; organic bases such as various amines, and basic amino acids; and the like. The amount of the basic substance is preferably an amount needed to neutralize a reaction system comprising the reaction mixture containing the sugar derivative-modified silicone as a main component but, as necessary, the added amount may be adjusted to an amount by which weak acidity or weak alkalinity is obtained.

In addition, an alkaline buffer may be further added in an amount corresponding to 100 ppm to 50,000 ppm of the reaction mixture containing the sugar derivative-modified silicone obtained after the acidizing step as a main component. A minute amount of acid may be locally dissolved in the reaction mixture containing the sugar derivative-modified silicone as a main component even after a neutralization or filtration step. By adding an alkaline buffer, the liquidity of the cosmetic composition or the like into which the sugar derivative-modified silicone is blended is maintained on the alkali side, which makes it possible to reduce the risk of odorization caused by the impurities of the sugar derivative-modified silicone. A useful alkaline buffer is not particularly limited as long as the alkaline buffer comprises a combination of a strong base and a weak acid. Examples of the alkaline buffer include trisodium phosphate, tripotassium phosphate, trisodium citrate, sodium acetate, and other alkaline buffers. Furthermore, the alkaline buffers may be added to a cosmetic composition starting material or the like comprising a sugar derivative-modified silicone or a composition thereof, or a mixture containing the same as a main component, or may be added to a composition at the preparation stage or after the blending of a sugar derivative-modified silicone or cosmetic composition that contains other cosmetic composition starting material or water. By so doing, odorization during formulation or over time can be more effectively suppressed.

The sugar derivative-modified silicone or the mixture containing the same as a main component can also be subjected to hydrogenation treatment as a step before or after treatment in the presence of an acidic inorganic salt in step [W]. A deodorizing treatment using a hydrogenation reaction may be performed after treatment in the presence of the acidic inorganic salt of the step [W]. On the other hand, the treatment in the presence of the acidic inorganic salt of the step [W] may be performed after deodorizing treatment using a hydrogenation reaction. However, hydrogenation treatment may generally lead to an increase in the cost of the product.

A second aspect of the present invention is an external use preparation, a cosmetic composition, or an industrial material including the liquid high purity sugar derivative-modified silicone or the composition thereof obtained by the production method of the present invention.

External Use Preparation and Cosmetic Composition

Since the high purity derivative-modified silicone or the composition thereof obtained by the production method of the present invention is a transparent or translucent liquid, it is possible to suitably blend the high purity sugar derivative-modified silicone or the composition thereof into an external use preparation or a cosmetic composition and can form the external use preparation or cosmetic composition of the present invention. It is also possible to produce a starting material for external use preparations and cosmetic compositions containing the sugar derivative-modified silicone or the composition thereof obtained by the production method of the present invention and to blend the starting material into an external use preparation or a cosmetic composition.

In particular, the liquid high purity sugar derivative-modified silicone composition obtained by the production method of the present invention has high transparency and the transparency is stable with respect to the temperature history or after long term storage. Therefore the composition can be advantageously blended in external use preparations or cosmetic compositions that require a transparent or translucent appearance. The sugar derivative-modified silicone or the composition thereof obtained by the production method of the present invention has a low degree of odor and produces practically no odor during formulation or over time. Moreover, there is the advantage of breaking almost no silicon-oxygen bonds which may form the main chain of the sugar derivative-modified silicone and the carbon-oxygen bonds which may form the side chains. Therefore, the sugar derivative-modified silicone or the composition thereof obtained by the production method of the present invention can be suitably used as a starting material for external use preparations and cosmetic compositions used on the human body.

The proportion of the sugar derivative-modified silicone or the composition thereof in the starting material for an external use preparation or a cosmetic composition is preferably from 10 to 100 wt. % (mass %), more preferably from 20 to 100 wt. % (mass %), and even more preferably from 30 to 100 wt. % (mass %) relative to the total weight (mass %) of the starting material. The proportion of the starting material compounded blended in the external use preparation or the cosmetic composition is not particularly limited but, for example, can be from 0.1 to 40 wt. % (mass %), and is preferably from 1 to 30 wt. % (mass %), more preferably from 2 to 20 wt. % (mass %), and even more preferably from 3 to 10 wt. % (mass %) relative to the total weight (mass) of the external use preparation or the cosmetic composition.

The liquid high purity sugar derivative-modified silicone or the composition thereof obtained by the production method of the present invention can be applied to applications common to novel organopolysiloxane described in Patent Document 25 (Japanese Unexamined Patent Application Publication No. 2011-246705A), and Patent Document 26 (Japanese Unexamined Patent Application Publication No. 2011-246706A), low odor sugar alcohol-modified silicone described in Patent Document 27 (Japanese Unexamined Patent Application Publication No. 2012-246445A), novel liquid organopolysiloxane described in Patent Document 28 (Japanese Unexamined Patent Application Publication No. 2012-246446A), or the sugar alcohol-modified silicone described in Patent Document 31 (Japanese Unexamined Patent Application Publication No. 2012-046508A) according to the structure and the type of functional group. The liquid high purity sugar derivative-modified silicone or the composition thereof obtained by the production method of the present invention can be used in the same manner as the novel organopolysiloxane described in Patent Documents 25 and 26, the low odor sugar alcohol-modified silicone described in Patent Document 27, the novel organopolysiloxane described in Patent Document 28, and the sugar alcohol-modified silicone described in Patent Document 31 with regard to combinations with any cosmetic composition starting material components, external use preparations, and, in particular, formulations, types, and formulation examples of cosmetic compositions, and can be blended into various cosmetic compositions or the like.

The external use preparation composition according to the present invention is not particularly limited, provided that the composition is applied to the human body as a cosmetic composition or a medicament. Specific examples of cosmetic composition products of the present invention include skin use cosmetic composition products such as skin cleansing agent products, skin care products, makeup products, anti-perspirant products, and ultraviolet light blocking products; hair use cosmetic composition products such as hair use cleansing agent products, hair dressing products, hair use coloration products, hair growth products, hair rinsing products, hair conditioning products, and hair treatment products; and bath use cosmetic composition products. Examples of the medicament of the present invention include hair regrowth agents, hair growth promoters, analgesics, germicides, anti-inflammatory agents, refreshing agents, and skin anti-aging agents, but are not limited thereto.

The skin use cosmetic products can be used on any site of the entire body including the scalp, face (including lips, eyebrows, and cheeks), fingers, and fingernails. Specific examples thereof include skin cleansing agent products such as cleansing gels, cleansing creams, cleansing foams, cleansing milk, cleansing lotion, face washing creams, eye makeup removers, face washing foams, liquid soaps (body soaps), hand soaps, gel-like soaps, solid soaps, facial rinse, body rinse, shaving creams, nail polish removers, and acne treatment cosmetic compositions; skin care products such as skin creams, scalp treatments, skin milks, milk lotions, emulsions, skin lotions, moisturizer, beauty lotion, facial packs, body powders, essences, shaving lotions, and massage lotions; makeup products such as foundations, liquid foundations, oil-based foundations, makeup bases, blooms, face powders, concealer, blemish balm (BB) cream, color control (CC) cream, lipstick, lip creams, cheek coloring, lip glosses, eye shadow, eye liners, eye creams, eyebrow pencils, eyelash cosmetic composition products, eyebrow pencils, eyebrow brushes, mascaras, blushers, cheek cosmetic compositions (cheek colors, cheek rouges), manicures, pedicures, nail colors, nail lacquers, enamel removers, and nail polishes; anti-perspirants such as deodorants; and ultraviolet light blocking products such as sunscreen agents, and tanning use medicaments (sun tanning agent.

Examples of the scalp use cosmetic products include hair use cleansing agents such as shampoos, and rinse-in shampoos; hair dressing products such as hair oils, hair waxes, hair use curl holding agents, setting agents, hair creams, hairsprays, and hair liquids; hair use coloration products such as hair coloring substances, hair color sprays, hair color rinses, and hair color sticks; hair growing products such as hair tonics, hair treatment essences, and hair packs; and hair rinse or hair conditioning products such as oil rinses, cream rinses, treatment rinses, hair conditioners, and hair treatments. Examples of bath use cosmetic products include bath oils, bath salts, and bath foams.

The external use preparation composition and in particular, the form of the cosmetic compositions according to the present invention is not particularly limited, and these can be preferably used in the form of a liquid (water-in-oil type), O/W (oil-in-water type) emulsion, W/O cream-like, O/W cream-like, a solid (stick shape and the like), a polyol type emulsion in oil, an oil type emulsion in polyol, a multilayer emulsion type such as W/O/W or O/W/O, a two layer separation type (shake mixing type before use), paste-like, gel-like, powder-like, multi-layer, mousse-like, mist-like, granule, flake, crushed stone, and the like. Particularly preferable forms are W/O milk, W/O creams, solids, pastes, gels, and powders.

The vessel of the external use preparation composition and in particular, the cosmetic compositions according to the present invention is not particularly limited, and it is possible to fill the composition in any vessel such as a jar, a pump, a tube, a bottle, a pressurized can discharge vessel, a pressure resistant aerosol vessel, a light shielding vessel, a compact vessel, a metal dish, a stick vessel, a delivery vessel, a spray vessel, and a vessel with a partition with a mixed liquid discharge port. The tube tends to be separated in a normal silicone formulation, but the external use preparation composition according to the present invention and in particular, the cosmetic composition is stably excellent. Therefore there is an advantage in that it is possible to fill the composition in the tube vessel and stably store.

The following other components generally used in external use preparations or cosmetic compositions may be added to the external use preparation or the cosmetic composition of the present invention, provided that such components do not inhibit the effectiveness of the present invention: water, powders or coloring agents, hydroxy acid, wax, fiber, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and perfumes. However, the additives are not particularly limited to thereto.

The water that can be used in the cosmetic composition or external use preparation of the present invention needs to be clean and free of components that are harmful to the human body, and examples thereof include tap water, purified water, mineral water, and deep sea water.

Oil Agent

The oil agent that can be used in the cosmetic composition or external use preparation according to the present invention is preferably one or more oil agents selected from silicone oils, non-polar organic compounds, and low-polarity to high-polarity organic compounds that are liquid at 5 to 100° C., and the non-polar organic compounds and low-polarity to high-polarity organic compounds are preferably hydrocarbon oils, fatty acid ester oils, and liquid fatty acid triglycerides. These are components that are particularly widely used as base materials for cosmetic compositions, but it is possible to additionally use one or more types of compound selected from among publicly known vegetable oils and fats, animal oils and fats, higher alcohols, fatty acid triglycerides, artificial sebum and fluorine-based oils as well as these oil agents.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (e.g. a hydrocarbon oil, a fatty acid ester oil, or the like), the cosmetic composition comprising a non silicone-based oil agent along with a silicone oil is advantageous in that a smoother, more luxurious tactile sensation is imparted.

The oil agents are the same as those disclosed by the present applicant in paragraphs [0141] to [0150] and the like of Patent Document 28 (Japanese Unexamined Patent Application Publication No. 2012-246446A).

Powder or Coloring Agent

A powder or coloring agent which can be used in the cosmetic composition or external use preparation according to the present invention is one that is commonly used as a component of a cosmetic composition, and includes white or colored pigments and extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular limitation. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range of 1 nm to 100 µm. Particularly, when compounding the powder or coloring agent as a pigment, preferably one or two or more selected from an inorganic pigment powder, an organic pigment powder, and a resin powder having an average particle size in a range of 1 nm to 20 µm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated, for example.

Specific examples include the same powders or coloring agents disclosed in paragraphs [0219] to [0226] or the like of Patent Document 28.

Of the powders exemplified, description of a silicone elastomer powder will be given. The silicone elastomer powder is a crosslinked product of a straight-chain diorganopolysiloxane formed principally from diorganosiloxy units (D units), and can be preferably obtained by crosslinking an organohydrogenpolysiloxane having a silicon-bonded hydrogen atom on the side chain or the molecular terminal and a diorganopolysiloxane having an unsaturated hydrocarbon group such as an alkenyl group or the like on the side chain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. When surface treatment is performed on the sugar derivative-modified silicone or the composition thereof obtained by the production method of the present invention, uniform treatment can be performed with good treatment efficiency, and thus it is possible to provide a unique effect or feel corresponding to the type of the sugar derivative-modified silicone without diminishing the suede-like feel of the silicone elastomer powder. Furthermore, when the sugar derivative-modified silicone or the composition thereof is blended into a cosmetic composition together with a silicone elastomer powder, the dispersion stability of the powder in the overall cosmetic composition is improved, and it is possible to obtain a cosmetic composition that is stable over time.

The silicone elastomer powder can be in various forms such as spherical, flat, amorphous, or the like. The silicone elastomer powder may also be in the form of an oil dispersion. A silicone elastomer powder having particulate form, in which the primary particle size when observed using an electron microscope and/or the average primary particle size measured by laser analysis or scattering, are in a range of 0.1 to 50 μm, and the primary particles having spherical forms can be preferably compounded in the cosmetic composition of the present invention. The silicone elastomer that constitutes the silicone elastomer powder is preferably one having a hardness, as measured using a type A durometer in the "Rubber, Vulcanized or Thermoplastic-Determination of Hardness" specified in JIS K 6253, of 80 or lower, and more preferably 65 or lower.

Of these silicone elastomer powders, specific examples of silicone elastomer spherical powders, in particular, are the same as those disclosed in paragraph [0223] of Patent Document 28 and may be silicone elastomer powders that have been subjected to various surface treatments such as water-repellent treatment, as disclosed in paragraphs [0224] to [0225] of Patent Document 28.

It is possible to further blend another surfactant in the cosmetic composition or external use preparation of the present invention. These other surfactants are components that function as cleansing components of the skin or the hair or, alternatively, as the oil agent or an emulsifier, and can be selected as desired depending on the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those disclosed in paragraphs [0237] to [0242] and the like of Patent Document 28. The sugar derivative-modified silicone according to the present invention functions as a dispersant because it has polar groups and non-polar groups in the molecule. Therefore, when used in combination with a nonionic surfactant, it functions as an aid to enhance the stability of the nonionic surfactant, and may improve the overall stability of the formulation. In particular, the liquid high purity sugar derivative-modified silicone or the composition thereof obtained by the production method of the present invention can be used in combination with a polyoxyalkylene-modified silicone (polyether-modified silicone), a (poly)glycerin derivative-modified silicone, and the like due to having enhanced compatibility and affinity with various modified silicones. Moreover, nonionic surfactants of these silicones in which an alkyl branch, a straight chain silicone branch, a siloxane dendrimer branch, or the like is provided as necessary along with the hydrophilic group can also be advantageously used.

Depending on the intended use thereof, the cosmetic composition or external use preparation of the present invention can contain one or two or more polyhydric alcohols and/or lower monohydric alcohols. These alcohols are the same as those disclosed in paragraph [0227] and the like of Patent Document 28.

Depending on the purpose thereof, the cosmetic composition or the external use preparation of the present invention can contain one or two or more inorganic salts and/or organic salts. These salts are the same as those disclosed in paragraph [0248] and the like of Patent Document 28.

Depending on the purpose thereof, the cosmetic composition or the external use preparation of the present invention can contain at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax. These silicone-based components are the same as those disclosed in paragraphs [0262] to [0287] and the like of Patent Document 28.

Depending on the intended use thereof, the cosmetic composition or external use preparation of the present invention can contain one or two or more water-soluble polymers. These water-soluble polymers are the same as those disclosed in paragraphs [0228] to [0232] and the like of Patent Document 28.

Depending on the intended use thereof, the cosmetic composition or external use preparation of the present invention can contain one or two or more ultraviolet light blocking components. These ultraviolet light blocking components are the same as the organic and inorganic ultraviolet light blocking agents disclosed in paragraphs [0243] to [0247] and the like of Patent Document 28, but specifically, an ultraviolet light blocking component that can be suitably used is at least one selected from the group consisting of microparticulate titanium oxide, microparticulate zinc oxide, 2-ethylhexyl p-methoxycinnamate, 4-tert-butyl-4'-methoxydibenzoylmethane, diethylamino hydroxybenzoyl hexyl benzoate, benzotriazole-based UV absorbers, and triazine-based UV absorbers such as 2,4,6-tris[4-(2-ethylhexyloxycarbonyl)anilino]1,3,5-triazine (INCI: octyl triazone) and 2,4-bis([4-(2-ethyl-hexyloxy)-2-hydroxy]phenyl)-6-(4-methoxyphenyl)-1,3,5-triazine (INCI: bis-ethylhexyloxyphenol methoxyphenyl triazine, product name: Tinosorb®S). These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

By using an ultraviolet light blocking component in combination with the sugar derivative-modified silicone or the composition thereof in the cosmetic composition or the external use preparation of the present invention, it is possible to stably disperse the ultraviolet light blocking component in the cosmetic composition while improving the feeling to touch and storage stability of the overall cosmetic composition, and it is therefore possible to impart excellent ultraviolet light blocking properties to the cosmetic composition.

Various components other than the components described above can be used in the cosmetic composition or external use preparation of the present invention, provided that such use does not impair the effects of the present invention. Examples thereof include hydroxy acid, wax, fiber, oil-soluble gelling agents, organo-modified clay minerals, water-swellable clay minerals, preservatives, bioactive components, skin beautifying components, pH adjusting agents, antioxidants, solvents, chelating agents, moisturizing components, and perfumes. These optional components for a cosmetic product are the same as those disclosed in paragraphs [0235], [0233], [0249] to [0260], and the like of Patent Document 28.

Additionally, in cases where the cosmetic composition or the external use preparation of the present invention is an antiperspirant, or depending on the purpose thereof, the cosmetic composition or the external use preparation can contain an anti-perspiration active component and/or a deodorant agent. These antiperspiration components and deodorant components are the same as those disclosed in paragraphs [0254] to [0263] and the like of Patent Document 27. Similarly, in cases in which the cosmetic composition or external use preparation according to the present invention is an antiperspirant composition, the preparation, method of use, and the like of the various antiperspirant compositions are the same as those disclosed in paragraphs [0264] to [0315] and the like of Patent Document 27.

INDUSTRIAL APPLICABILITY

The production method for a liquid high purity sugar derivative-modified silicone or the composition thereof of the present invention is inexpensive and simple, produces little waste, has excellent yield or productivity, and can reasonably accommodate production on a commercial scale. The sugar derivative-modified silicone or the composition thereof obtained by the production method of the present invention has an extremely small risk of phase separation, sedimentation of unreacted starting material, or the like occurring after production. In particular, the liquid sugar derivative-modified silicone or the composition thereof obtained by the production method of the present invention is stable with respect to temperature history, and maintains the stability and highly transparent appearance after long term storage. Therefore there is no problem derived from an opaque appearance, and moreover, since dilution is possible by the liquid oil solution while maintaining transparency, handleability is excellent. Therefore, the present invention solves the essential problems of using conventional sugar-modified silicone.

Accordingly, the liquid high purity sugar derivative-modified silicone or the composition thereof of the present invention not only can be used in cosmetic compositions or external use preparations such as medicaments, but can also be widely used in general industrial applications, and can provide the above various applications with the surface activity, emulsification/dispersion effect, surface treatment effect, adsorption effect, coating effect, moisture retention/water retention effect, emollient effect, abrasion reduction effect, lubrication effect, penetrating capability, solubilizing/compatibilizing capability, protection effect, adhesion effect, viscosity-increasing or viscosity-adjusting effect, or maintenance of these effects, and the like that are intrinsic to sugar derivative-modified silicone.

Specifically, the liquid high purity sugar derivative-modified silicone or the composition thereof obtained by the present invention can be suitably used not only as a starting material for external use preparations, medicaments, or cosmetic compositions, but also, for example, as a fiber treating agent, a varnish or paint additive with excellent heat resistance, weather resistance, and electrical characteristics, a coating agent, a primer, a tackifier, a polyol main agent, a foam stabilizer, or a modifier for various urethanes or foaming materials, a mold-releasing agent or peeling agent, an antifoam agent, greases or oil compounds, oils for insulation, burnishing, water repellency, heating/cooling mediums, lubrication, or the like, a modifier, additive, or surface treating agent for a rubber or resin, a compounding agent, modifier, or precursor for a silane coupling agent, a coating material or sealing material for a building/lining, a protecting agent or lubricant or buffering agent for optical fibers/electrical lines, and starting materials for general industrial materials such as electronic/electrical parts.

EXAMPLES

The present invention will be described in detail hereinafter using Examples and Comparative Examples, but the present invention is not limited to the Examples described below.

Note that in the Production Examples and Comparative Examples below, the language "production of sugar derivative-modified silicone No. X" is used for the sake of convenience, but the obtained products are in the form of mixtures containing a small amount of unreacted starting material and the like in addition to the main components.

In the following compositional formulae, "Me" represents a methyl ($-CH_3$) group, "M" represents a $Me_3SiO$ group (or an $Me_3Si$ group), "D" represents an $Me_2SiO$ group, "$D^H$" represents an MeHSiO group, and "$M^R$" and "$D^R$" respectively represent units in which a methyl group in "M" or "D" is modified by any substituent. Additionally, in the production examples, "IPA" represents isopropyl alcohol.

Xylitol monoallyl ether and xylitol residue described below are starting materials and functional groups indicated in the present specification. In greater detail, the xylitol monoallyl ether is the starting material that contains the xylitol monoallyl ether at an approximate ratio of the amount of substance of 9:1 represented by structural formula: $CH_2=CH-CH_2-OCH_2[CH(OH)]_3CH_2OH$ and structural formula: $CH_2=CH-CH_2-OCH\{CH(OH)CH_2OH\}_2$, and the xylitol residue of $-C_3H_6-OCH_2[CH(OH)]_3CH_2OH$, or $-C_3H_6-OCH\{CH(OH)CH_2OH\}_2$ corresponding to the respective structural formulae is introduced at the same ratio of the amount of substance in the sugar derivative-modified silicone according to the present invention.

The xylitol monoallyl ether starting material used below has purity of approximately 80 to 90%, but most of the remaining component (impurities) other than the main component is xylitol that is not allyl etherified.

Production Example 1

Synthesis of Sugar Derivative-modified Silicone No. 1

460.4 g of a methylhydrogenpolysiloxane represented by average composition formula $MD_{475}D^H{}_{10.5}M$ and 35.9 g of a vinyl tris(trimethylsiloxy)silane represented by average composition formula $CH_2=CH-Si(OSi(CH_3)_3)_3$ were prepared in a reaction vessel, and 0.85 g of an IPA solution of a platinum-1,3-divinyl-1,1,3,3-tetramethyldisiloxane complex (Pt concentration: 0.45 wt. %) was added while stirring under a nitrogen stream. After a reaction for 3.5 hours at 60 to 70° C., 2 g of the reaction liquid was sampled, and it was confirmed with an alkali decomposition gas generation method (the remaining Si—H groups are decomposed using a KOH ethanol/aqueous solution, and the reaction rate is calculated from the volume of the generated hydrogen gas) that the target reaction had been achieved. The next day, when 99.9 g of hexadecene (α olefin purity 91.7%) was added to a room temperature reaction mixture by stirring, heat was generated due to the reaction and the temperature is raised to 54° C. The reaction continued without change for two hours, then the reaction rate was confirmed to reach a target by the same method. Next, 54.1 g of xylitol monoallyl ether (purity of 84.3%), 525 g of IPA, and 0.075 g of natural vitamin E were prepared in the reaction mixture, and 0.83 g of the platinum catalyst solution was added at 45 to 50° C., and the reaction was performed for two hours at 60 to 65° C., then it was confirmed that the reaction rate reaches the target by the same method. Finally, 99.9 g of hexadecene (α olefin purity of 91.7%) was added, a reaction was performed for 2.5 hours at 50 to 65° C., it was confirmed with the same method that the reaction was complete, and a sugar derivative-modified silicone represented by the average composition formula: $MD_{47.5}D^{R*11}{}_{7.5}D^{R*21}{}_{2}D^{R*32}{}_{1}M$ was found to be generated.

In this formula, $R^{*11}$, $R^{*21}$, and $R^{*32}$ are as follows.

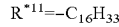

$R^{*11}$=—$C_{16}H_{33}$

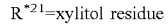

$R^{*21}$=xylitol residue

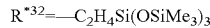

$R^{*32}$=—$C_2H_4Si(OSiMe_3)_3$

Next, after the low-boiling components were removed under reduced pressure at 70 to 100° C., treatment was performed for 1.5 hours at 65° C. by adding an aqueous solution comprising 0.135 g of sodium bisulfate hydrate/11.3 g of ion exchanged water, and furthermore, an odor component generated and water were removed by depressurizing to 10 Torr or less. After this, 11.3 g of ion exchanged water was added again, in the same manner, an operation in which the odor component and water were removed by depressurizing treatment was repeated two times (the last depressurization operation was maintained at −55 to 65° C. for two hours at 10 Torr or less), and an opaque viscous liquid of a dark ivory color was obtained. By performing filtration at $N_2$ pressure by a pressure filter using ADVANTEC No. 424 filter paper (diameter 110 mm, Toyo Roshi Sha, Ltd.), 696 g of the composition including sugar derivative-modified silicone No. 1 represented by average composition formula: $MD_{47.5}D^{R*11}{}_{7.5}D^{R*21}{}_{2}D^{R*32}{}_{1}M$ was obtained as the dark ivory color opaque viscous liquid. Here, $R^{*11}$, $R^{*21}$, and $R^{*32}$ are as described above.

Production Example 2

Synthesis of Sugar Derivative-modified Silicone No. 2

92.78 g of dimethyl/methyl (aminopropyl) polysiloxane represented by average composition formula: $MD_{73}D^{R*2}{}_{2}M$, 7.22 g of glucono-δ-lactone, and IPA 50 g were prepared in a reaction vessel, and heated to 80° C. while stirring under a nitrogen stream. The reaction liquid appearance was a cloudy opaque liquid, but when the reaction was performed for 3.5 hours at 80° C., the appearance was substantially a transparent uniform liquid. Next, when a small amount of the reaction liquid was sampled and confirmed by neutralizing titration, the reaction was completed without detecting the amino group. The product was heated at 80 to 90° C. under reduced pressure and 94 g of the composition including the sugar derivative-modified silicone No. 2 represented by average composition formula $MD_{74}D^{R*22}{}_{2}M$ was obtained by distilling out IPA. The product was a dark yellow to orange brown opaque rubber-like soft solid at room temperature, but it was possible to confirm the soft solid is a liquid since it is a syrup-like extremely viscous fluid at 90° C. Here, in the formula, $R^{*2}$ and $R^{*22}$ are as follows.

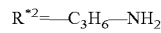

$R^{*2}$=—$C_3H_6$—$NH_2$

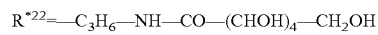

$R^{*22}$=—$C_3H_6$—NH—CO—$(CHOH)_4$—$CH_2OH$

Production Example 3

Synthesis of Sugar Derivative-modified Silicone No. 3

491.7 g of a methylhydrogenpolysiloxane represented by average composition formula $MD_{45}D^{H}{}_{13}M$, and 38.2 g of a vinyl tris(trimethylsiloxy)silane represented by average composition formula $CH_2$=CH—$Si(OSi(CH_3)_3)_3$ were prepared in a reaction vessel, and, 0.88 g of an IPA solution of a platinum-1,3-divinyl-1,1,3,3-tetramethyldisiloxane complex (Pt concentration: 0.45 wt. %) was added while stirring under a nitrogen stream. After the reaction was performed for 2 hours at 60 to 70° C., 2 g of the reaction liquid was sampled and it was confirmed that the reaction reached the target using an alkali decomposition gas generation method. After the reaction mixture was cooled to room temperature, when 106.3 g of dodecene (α olefin purity of 95.3%) was added, heat was generated by the reaction and the temperature was raised to 69° C. The reaction continued without change for 3.5 hours, then the reaction rate was confirmed to reach a target by the same method. Next, 57.5 g of xylitol monoallyl ether (purity of 85.2%), 560 g of IPA, and 0.080 g of natural vitamin E were prepared in the reaction mixture, and 0.88 g of the platinum catalyst solution was added at 45 to 50° C., and the reaction was performed for 2.5 hours at 55 to 65° C., then it was confirmed that the reaction rate reaches the target by the same method. Finally, 106.3 g of dodecene (α olefin purity of 95.3%) was added and the reaction was performed for 3 hours at 50 to 65° C., and when confirmed by the same method, the reaction was complete, and it was found that the sugar derivative-modified silicone was generated represented by average composition formula: $MD_{45}D^{R*12}{}_{10}D^{R*21}{}_{2}D^{R*32}{}_{1}M$. In the formula, $R^{*12}$, $R^{*21}$, and $R^{*32}$ are as follows.

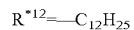

$R^{*12}$=—$C_{12}H_{25}$

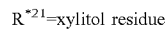

$R^{*21}$=xylitol residue

$R^{*32}$=—$C_2H_4Si(OSiMe_3)_3$

Next, after the low-boiling components were removed under reduced pressure at 60 to 100° C., treatment was performed for 3.3 hours at 65 to 70° C. by adding an aqueous solution comprising 0.127 g of sodium bisulfate hydrate/12 g of ion exchanged water, and furthermore, an odor component generated and water were removed by depressurizing to 10 Torr or less. After this, 12 g of ion exchanged water was added again, in the same manner, an operation in which the odor component and water were removed by depressurizing treatment was repeated two times (the last depressurization operation was maintained at −60 to 65° C. for two hours at 10 Torr or less), and an opaque viscous liquid of a dark ivory color was obtained. By performing filtration at $N_2$ pressure by a pressure filter using ADVANTEC No. 424 filter paper (diameter 110 mm, Toyo Roshi Kaisha, Ltd.), 734 g of the composition including sugar derivative-modified silicone No. 3 represented by average composition formula: $MD_{45}D^{R*12}{}_{10}D^{R*21}{}_{2}D^{R*32}{}_{1}M$ was obtained as the dark ivory color opaque viscous liquid.

Here, $R^{*12}$, $R^{*21}$, and $R^{*32}$ are as described above.

Production Example 4

Synthesis of Sugar Derivative-modified Silicone No. 4

462.8 g of a methylhydrogenpolysiloxane represented by average composition formula $MD_{37}D^{H}{}_{13}M$ and 44.0 g of a vinyl tris(trimethylsiloxy)silane represented by average composition formula $CH_2$=$CH$—$Si(OSi(CH_3)_3)_3$ were prepared in a reaction vessel, and 1.27 g of an IPA solution of a platinum-1,3-divinyl-1,1,3,3-tetramethyldisiloxane complex (Pt concentration: 0.45 wt. %) was added while stirring under a nitrogen stream. The reaction was performed for 8.5 hours at 70 to 75° C., then 2 g of the reaction liquid was sampled and it was confirmed that the reaction reached the target using an alkali decomposition gas generation method. The next day, when 116.6 g of dodecene (α olefin purity 95.3%) was added while heating the reaction mixture by stirring, heat was generated by the reaction and the temperature is raised from 36° C. to 88° C. When confirming after being held for 3 hours at 70 to 75° C., the target reaction rate had been achieved. Next, 62.5 g of xylitol monoallyl ether (purity of 85.2%), 560 g of IPA, and 0.080 g of natural vitamin E were prepared in the reaction mixture, and 0.88 g of the platinum catalyst solution was added at 45 to 50° C., and the reaction was performed for two hours at 45 to 65° C., then it was confirmed that the reaction rate reaches the target by the same method. Finally, 116.5 g of dodecene (α olefin purity of 95.3%) was added and the reaction was performed for two hours at 45 to 70° C., and when confirmed by the same method, the reaction was complete, and it was understood that the sugar derivative-modified silicone was generated represented by the average composition formula: $MD_{37}D^{R*12}{}_{10}D^{R*21}{}_{2}D^{R*32}{}_{1}M$. In the formula, $R^{*12}$, $R^{*21}$, and $R^{*32}$ are as follows.

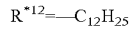

$R^{*12}$=—$C_{12}H_{25}$

$R^{*21}$=xylitol residue

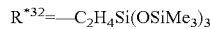

$R^{*32}$=—$C_2H_4Si(OSiMe_3)_3$

Next, after the low-boiling components were removed under reduced pressure at 65 to 105° C., treatment was performed for 1.5 hours at 60 to 70° C. by adding an aqueous solution comprising 0.120 g of sodium bisulfate hydrate/12 g of ion exchanged water, and furthermore, an odor component generated and water were removed by depressurizing to 15 Torr or less. After this, 12 g of ion exchanged water was added again, in the same manner, an operation in which the odor component and water were removed by depressurizing treatment was repeated two times (the last depressurization operation was maintained at −55 to 70° C. for two hours at 10 Torr or less), and an opaque viscous liquid of a dark ivory to grey-brown color was obtained. By performing filtration at $N_2$ pressure by a pressure filter using ADVANTEC No. 424 filter paper (diameter 110 mm, Toyo Roshi Kaisha, Ltd.), 750 g of the composition including sugar derivative-modified silicone No. 4 represented by average composition formula: $MD_{37}D^{R*12}{}_{10}D^{R*21}{}_{2}D^{R*32}{}_{1}M$ was obtained as the dark ivory color to skin color opaque viscous liquid. Here, $R^{*12}$, $R^{*21}$, and $R^{*32}$ are as described above.

Further, a mass ratio of the main component within the obtained composition (sugar derivative-modified silicone No. 4) and the impure xylitol derivative causing turbidity was estimated. In Production Example 4, a mol number of a C=C group of allyl xylitol was formulated to be 1.10 times the mol number of a $D^H$ group that is to react therewith. Accordingly, a material consumed by hydrosilylation out of 62.5 g used is 0.852×62.5 g/1.10=48.4 g, and surplus was calculated as 14.1 g. Meanwhile, two types of hydrophobic modifiers (vinyl tris(trimethylsiloxy)silane and dodecene) were charged in slight excess to the $D^H$ group, but since volatility was high, it was assumed that the hydrophobic modifiers were removed by heat depressurization treatment. By doing this, the mass of the modified silicone that is the main component was calculated as 764.4 g according to the mol number of the starting material methylhydrogenpolysiloxane and the molecular weight of each modifier and the added mol number. From the above, an abundance ratio of the main component and the turbid component was 764.4 g: 14.1 g=98.2:1.8 (at least 1.8% of the turbid component exist with respect to the main component). In this case, it is understood that the hydrophilic impurities less than 2% resulted in intense turbidity in the sugar derivative-modified silicone composition.

Production Example 5

Synthesis of Sugar Derivative-modified Silicone No. 5

197.2 g of a methylhydrogenpolysiloxane represented by average composition formula $M^HD_{400}M^H$, 2.8 g of xylitol monoallyl ether (purity of 91.2%), and 200 g of IPA were added to a reaction vessel, and heated to 70° C. while agitating under a nitrogen stream. Next, 0.060 g of an IPA solution of a platinum-1,3-divinyl-1,1,3,3-tetramethyldisiloxane complex (Pt concentration: 4.5 wt. %) was added, and the reaction was performed for 5 hours at 80° C. Then, 2 g of the reaction liquid was sampled, and it was confirmed with an alkali decomposition gas generation method that the reaction was complete. 200.0 g of dimethylpolysiloxane (2 cst, 25° C.) was added and mixed in the reaction liquid and dilution was performed. The sugar derivative-modified silicone No. 5 (composition comprising a composition including sugar derivative-modified silicone No. 5 as the main component and dimethylpolysiloxane (2 cst, 25° C.; diluent)) represented by average composition formula $M^{R*21}D_{400}M^{R*21}$ was obtained as a uniform viscous liquid that is somewhat brown-tinted in an ash-white color by distilling out the low-boiling component other than the diluent by heating the product under reduced pressure. The wt. (mass) ratio of the above-described silicone composition to the diluent was 1:1. In the formula, $R^{*21}$ is as follows.

$R^{*21}$=xylitol residue

Production Example 6

Synthesis of Sugar Derivative-modified Silicone No. 6

191.8 g of a methylhydrogenpolysiloxane represented by average composition formula $MD_{74}D^{H}{}_{1}M$, 9.0 g of xylitol monoallyl ether (purity of 91.2%), and 100 g of IPA were placed in a reaction vessel, and heated to 60° C. while agitating under a nitrogen stream. Next, 0.75 g of an IPA solution of a platinum-1,3-divinyl-1,1,3,3-tetramethyldisiloxane complex (Pt concentration: 0.45 wt. %) was added, and the reaction was performed for 6 hours at 60 to 75° C. Then the reaction was complete when confirmed by the alkali decomposition gas generation method for 2 g of the reaction liquid sampled. Next, 181 g of a composition comprising sugar derivative-modified silicone No. 6 represented by average composition formula: $MD_{74}D^{R^{*21}}{}_{1}M$ was obtained as a dark brown to grayish brown opaque liquid by removing the low-boiling components under reduced pressure at 70 to 110° C.

In the formula, $R^{*21}$ is as follows.

$R^{*21}$=xylitol residue

Production Example 7

Synthesis of Sugar Derivative-modified Silicone No. 7

First, 137.7 g of a methylhydrogenpolysiloxane represented by the average composition formula $MD_{42.9}D^{H}{}_{6.7}M$ and 14.9 g of a 3-methacryloxy propyl(tris(trimethylsiloxy) silylethyl dimethylsiloxy)silane represented by the following average composition formula:

[Chemical Formula 38]

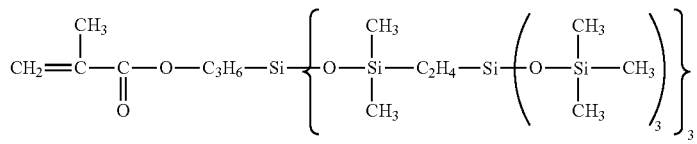

were placed to the reaction vessel and heated to 80° C. while stirring under a nitrogen stream. Next, 0.12 ml of an IPA solution of a platinum-1,3-divinyl-1,1,3,3-tetramethyl-disiloxane complex (Pt concentration: 0.45 wt. %) was added, and the reaction was performed for 2 hours at 80 to 90° C. A small amount of the reaction liquid was sampled, and it was confirmed with an alkali decomposition gas generation method that the target reaction rate had been achieved. Next, 36.0 g of hexadecene (α-olefin purity: 91.7%) was added to the reaction mixture, and after a reaction was performed for 1 hour at 85 to 100° C., it was confirmed with the same method that the target reaction rate had been achieved. Next, 10.1 g of a xylitol monoallyl ether (purity of 91.2%) and 120 g of IPA were added to the reaction mixture, and 0.20 mL of the platinum catalyst described above was introduced. After a reaction was performed for 4 hours at 65 to 80° C., sampling was performed. As a result of calculating the reaction rate, it was found that a modified silicone intermediate represented by the average composition formula: $MD_{42.9}D^{R^{*31}}{}_{0.3}D^{R^{*21}}{}_{1.1}D^{R^{*11}}{}_{4.0}D^{H}{}_{1.3}M$ had been produced. In the formula, $R^{*11}$, $R^{*21}$ and $R^{*31}$ are as follows.

$R^{*11}$=—$C_{16}H_{33}$ $R^{*21}$=xylitol residue

[Chemical Formula 39]

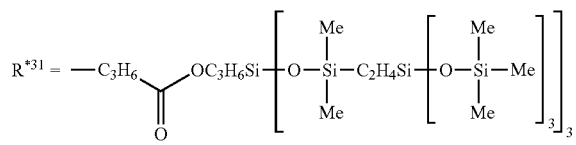

The reaction liquid was cooled to 50° C., and 2.1 g of 1,5-hexadiene and 0.025 g of natural vitamin E were added thereto and reaction was performed for 4 hours at 50 to 80° C. In this case, the Vi/H molar ratio upon crosslinking was 1.0. The mixture was sampled, and when the reaction rate was calculated, the reaction substantially has been completed. Next, 189 g of light yellow to gray white viscous liquid was obtained by distilling out the low-boiling components at 70 to 85° C. under reduced pressure.

69.0 g out of the obtained light yellow to gray white viscous liquid was placed in another reaction vessel, treatment was performed for 30 minutes at 60 to 70° C. by adding an aqueous solution comprising 69.0 g of caprylyl methicone (FZ-3196 manufactured by Dow Corning Toray Co., Ltd.: average composition formula $MD^{R^{*13}}{}_{1}M$, 2.9 cst (25° C.)) and 0.010 g of sodium bisulfate hydrate/1.0 g of ion exchanged water, and furthermore, an odor component generated and water were removed by depressurizing to 10 Torr or less. After that, 137 g of sugar derivative-modified silicone No. 7 (composition including sugar derivative-modified silicone No. 7 as the main component and composition comprising caprylyl methicone (diluent)) was obtained as an ivory color opaque liquid by repeating an operation two times of removing the odor component and water by adding 1.0 g of ion exchanged water and depressurizing in the same manner (the last depressurization operation was maintained at −60 to 70° C. for 80 minutes at 10 Torr or less). Here, the wt. (mass) ratio of the above-described silicone composition to the diluent was 1:1.

The sugar derivative-modified silicone (liquid sugar derivative-modified crosslinked silicone) No. 7 obtained by Production Example 7 is indicated in the following average structural formula (schematic diagram).

[Chemical Formula 40]

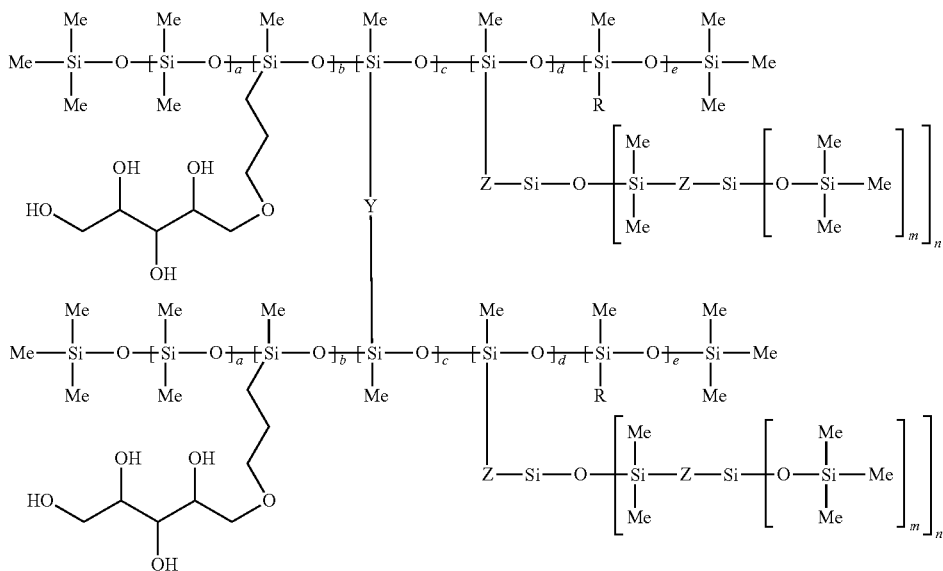

(In the formula, Me=methyl group, within [ ]n, Z=—$CH_2CH_2$—, outside of " " n, Z=—$C_3H_6$—COO—$C_3H_6$—, R=—$C_{16}H_{33}$, Y=—$(CH_2)_6$—, a=42.9, b=1.1, c=1.3, d=0.3, e=4.0, m=3, and n=3.)

Production Example 8

Synthesis of Sugar Derivative-modified Silicone No. 8

875.0 g of a methylhydrogenpolysiloxane represented by the average composition formula $MD_{44.7}D^H{}_2M$, 125.2 g of xylitol monoallyl ether (purity of 89.6%), 0.11 g of natural vitamin E, and 700 g of IPA were placed in a reaction vessel, and heated. According to a conventional method, the IPA solution of a platinum-1,3-divinyl-1,1,3,3-tetramethyldisiloxane complex (Pt concentration: 4.5%) was added, and the reaction was performed at 55 to 80° C. When the reaction liquid was sampled and the reaction rate was confirmed by the alkali decomposition gas generation method, the modified silicone intermediate was found to be generated represented by average composition formula: $MD_{44.7}D^{R*21}{}_1D^H{}_1M$. In the formula, $R^{*21}$=xylitol residue.

Next, 85 g of 1-octene (α olefin purity 97%) and the catalyst solution were added to the reaction vessel, and the reaction was completed in the same manner. As a result, the sugar derivative-modified silicone was found to be generated represented by average composition formula: $MD_{44.7}D^{R*21}{}_1D^{R*13}{}_1M$. In this formula, $R^{*13}$ and $R^{*21}$ are as follows.

$R^{*13}$=—$C_8H_{17}$ $R^{*21}$=xylitol residue

Next, after the low-boiling components were removed under reduced pressure at 65 to 105° C., treatment was performed for 20 minutes at 65 to 85° C. by adding an aqueous solution comprising 0.16 g of sodium bisulfate hydrate/15 g of ion exchanged water, and furthermore, an odor component generated and water were removed by depressurizing to 10 Torr or less. After that, an operation of removing the odor component and water by adding 15 g of ion exchanged water again, treatment under generally the same conditions, and depressurizing was repeated two times (the last depressurization operation was maintained for 1 hour), and 996 g of the composition including the sugar derivative-modified silicone No. 8 represented by average composition formula: $MD_{44.7}D^{R*21}{}_1D^{R*13}{}_1M$ was obtained as a gray black opaque viscous liquid. Here, $R^{*13}$ and $R^{*21}$ are as described above.

Further, a mass ratio of the main component within the obtained composition (sugar derivative-modified silicone No. 8) and the impure xylitol derivative causing turbidity was estimated. In Production Example 8, a mol number of a C=C group of allyl xylitol was formulated to be 2.40 times of the mol number of a $D^H$ group that is to react therewith. Accordingly, a material consumed by hydrosilylation out of 125.2 g used is 0.896×125.2 g/2.40=54.1 g, and surplus was calculated as 71.1 g. Meanwhile, 1-octene was also charged in excess to the $D^H$ group, but since volatility was high, the 1-octene was removed by heat depressurization treatment. By doing this, the mass of the modified silicone that is the main component was calculated as 948.9 g according to the mol number of the starting material methylhydrogenpolysiloxane and the molecular weight of modifier and the added mol number. From the above, the abundance ratio of the main component and the turbid component is 948.9 g:71.1 g=93.0:7.0 (the impurities were equivalent to 7.5% of the main component), and in this case, it was found that hydrophilic impurities of 7%, which is a large amount, remained in the sugar derivative-modified silicone composition, and there was intense turbidity.

Comparative Example 1

Comparative Composition RE-1 Containing Sugar Derivative-modified Silicone No. 1

The dark ivory color opaque viscous liquid obtained in Production Example 1 (composition including sugar derivative-modified silicone No. 1 as the main component) was used as a sample without further changes.

Comparative Example 1-2

Comparative Composition RE-1(-2) Containing Sugar Derivative-modified Silicone No. 1

210 g of the dark ivory color opaque viscous liquid obtained in Production Example 1 (composition including sugar derivative-modified silicone No. 1 as the main component) was prepared in the reaction vessel, thereto was added 18.9 g of aqueous solution prepared by dissolving 6.3 g of trehalose dihydrate (crystalline powder, white) into 12.6 g of purified water, and the mixture was stirred for 1.5 hours at 90° C. Next, when dewatering was carried out for 40 minutes by depressurizing the system to 10 Torr or less, water droplets disappeared from the system. Pressure was recovered after cooling to 40° C. while stirring. The contents of the reaction vessel was an opaque viscous liquid having strong turbidity.

An edge of ADVANTEC No. 424 filter paper (retained particle diameter 4 μm) with diameter of 110 mm (slightly larger than the inner diameter of the pressure filter) was folded evenly on a plate of the pressure filter, and was tightly spread, then the filter was set at a base. At this time, the filter stands vertically, a receiver was installed below a filtrate outlet having a narrow diameter below the position of the plate.

100 g of the white turbid dispersion was collected in a cup, thereto was added 10 g of diatomaceous earth powder with a median particle size of 30.6 μm, and was stirred well and mixed with a spatula to form a slurry. The slurry was poured onto the filter paper set in the pressure filter, then nitrogen pressure was applied from an upper portion after covering the filter with a lid. As a result, a filter layer composed mainly of diatomaceous earth powder with a median particle size of 30.6 μm was formed.

Next, when the remaining portion of the white turbid dispersion and filtrate collected during filter layer formation were poured onto the filter layer again, and nitrogen pressure was applied from the upper portion after covering the filter with a lid, 171 g of an opaque viscous liquid having strong white turbidness was obtained. The turbidity of the appearance was further increased in comparison to prior to treatment (that is, a sample of Comparative Example 1). The result was used as the sample of comparative composition RE-1(-2).

Comparative Example 2

Preparation of Comparative Composition RE-2 Containing Sugar Derivative-modified Silicone No. 2

The composition including sugar derivative-modified silicone No. 2 that is a syrup like extremely viscous liquid at 90° C. obtained in Production Example 2 as the main component was used as a sample without further changes.

Comparative Example 3

Preparation of Comparative Composition RE-3 Containing Sugar Derivative-modified Silicone No. 3

The dark ivory color opaque viscous liquid obtained in Production Example 3 (composition including sugar derivative-modified silicone No. 3 as the main component) was used as a sample without further changes.

Comparative Example 4

Preparation of Comparative Composition RE-4 Containing Sugar Derivative-modified Silicone No. 4

The dark ivory color opaque viscous liquid obtained in Production Example 4 (composition including sugar derivative-modified silicone No. 4 as the main component) was used as a sample without further changes.

Comparative Example 5

Preparation of Comparative Composition RE-5 Containing Sugar Derivative-modified Silicone No. 5

The uniform viscous liquid that is somewhat brown-tinted in an ash-white color obtained in Production Example 5 (composition including sugar derivative-modified silicone No. 5 as the main component and composition comprising dimethylpolysiloxane (2 cst, 25° C.; diluent)) was used as a sample without further changes.

Comparative Example 6

Preparation of Comparative Composition RE-6 Containing Sugar Derivative-modified Silicone No. 6

The dark brown to grayish brown opaque liquid obtained in Production Example 6 (composition including sugar derivative-modified silicone No. 6 as the main component) was used as a sample without further changes.

Comparative Example 7

Preparation of Comparative Composition RE-7 Containing Sugar Derivative-modified Silicone No. 7

The ivory color opaque liquid obtained in Production Example 7 (composition including sugar derivative-modified silicone No. 7 as the main component, and composition comprising caprylyl methicone (diluent)) was used as a sample without further changes.

Comparative Example 8

Preparation of Comparative Composition RE-8 Containing Sugar Derivative-modified Silicone No. 8

The gray black opaque viscous liquid obtained in Production Example 8 (composition including sugar derivative-modified silicone No. 8 as the main component) was used as a sample without further changes.

Comparative Example 8-2

Preparation of Comparative Composition RE-8(-2) Containing Sugar Derivative-modified Silicone No. 8

Glass fiber filter paper GC-90 (retained particle diameter 0.5 μm) with diameter of 90 mm was set in stainless steel holder with tank ADVANTEC KST-90, and a tank unit and a base plate (O-ring, filter paper, part placing a support screen) were fastened by a dedicated bolt, washer, and nut and fixed such that there was no leakage. Thereby, there was a structure in which the entire edge of the filter paper was fastened vertically and leakage was prevented.

150 g of the gray black opaque viscous liquid obtained in Production Example 8 (composition including sugar derivative-modified silicone No. 8 as the main component) was introduced from an opening at an upper part of the tank, the opening was closed by a tank cap, and filtration was performed by applying nitrogen pressure of 0.4 MPa. As a result, 147 g of an ash-brown opaque viscous liquid was obtained, but turbidity of the appearance was not reduced at all in comparison to prior to filtration. The result was used as the sample of comparative composition RE-8(-2).

When the stainless steel holder with tank was disassembled after filtration ends and the presence or absence of leakage from the base plate was confirmed, it was found that there was no leakage and the whole amount of the filtrate passed through only the filter paper center portion.

Example 1

Preparation of Liquid High Purity Sugar Derivative-modified Silicone No. 1

150 g of the dark ivory color opaque viscous liquid obtained in Production Example 1 (composition including sugar derivative-modified silicone No. 1 as the main component) and 149 g of n-heptane were prepared in the reaction vessel, and the white turbid dispersion was obtained by stirring the mixture for 55 minutes at 75 to 95° C. The mixture was cooled to room temperature while stirring.

An edge of ADVANTEC No. 424 filter paper (retained particle diameter 4 μm) with diameter of 110 mm (slightly larger than the inner diameter of the pressure filter) was folded evenly on a plate of the pressure filter, and was tightly spread, then the filter was set at a base. At this time, the filter stands vertically, a receiver was installed below a filtrate outlet having a narrow diameter below the position of the plate.

100 g of the white turbid dispersion was collected in a cup, thereto was added 5.5 g of diatomaceous earth fine powder with a median particle size of 10.9 μm, and was stirred well and mixed with a spatula to form a slurry. The slurry was poured onto the filter paper set in the pressure filter, then nitrogen pressure was applied from an upper portion after covering the filter with a lid. As a result, a filter layer composed mainly of diatomaceous earth fine powder with a median particle size of 10.9 μm was formed.

Next, when the remaining portion of the white turbid dispersion and filtrate collected during filter layer formation were poured onto the filter layer again, and nitrogen pressure was applied from the upper portion after covering the filter with a lid, surprisingly, the whole amount of the filtrate was uniform liquid with pale yellow substantially transparent to translucent, and the weight was 268 g.

The filtrate was placed in a clean flask and toluene was removed in nitrogen gas stream under reduced pressure at 60 to 100° C., thereby liquid high purity sugar derivative-modified silicone No. 1 was obtained as a light yellow color semi-transparent uniform viscous liquid. The liquid high purity sugar derivative-modified silicone No. 1 is represented by the average composition formula: $MD_{47.5}D^{R*11}{}_{7.5}D^{R*21}{}_{2}D^{R*32}{}_{1}M$. (collected amount of 136 g) In the formula, $R^{*11}$, $R^{*21}$, and $R^{*32}$ are as follows.

$R^{*11}$=—$C_{16}H_{33}$ $R^{*21}$=xylitol residue $R^{*32}$=—$C_2H_4Si(OSiMe_3)_3$ Example 1-2

Preparation of Liquid High Purity Sugar Derivative-modified Silicone No. 1

When 150 g of the dark ivory color opaque viscous liquid obtained in Production Example 1 (composition including sugar derivative-modified silicone No. 1 as the main component), 156 g of toluene, and 4.5 g of trehalose dihydrate (crystalline powder, white) were prepared in the reaction vessel and the mixture was stirred, the mixture was a gray tan turbid liquid. When the mixture was stirred for 70 minutes by heating to 65 to 80° C., surprisingly, it was noticed that white crystals grown with a large granular form in the cloudy liquid danced as if the crystals were scum. Stirring was stopped and the mixture was cooled to room temperature.

In the same manner as the case of Example 1, the pressure filter, plate, filter paper, and receiver were set.

100 g of the turbid liquid obtained by the treatment described above was collected in a cup, thereto was added 5 g of diatomaceous earth fine powder with a median particle size of 10.9 μm, and the mixture was stirred well and mixed with a spatula to form a slurry. The slurry was poured onto the filter paper set in the pressure filter, then nitrogen pressure of 0.1 to 0.2 MPa was applied from an upper portion after covering the filter with a lid. As a result, a filter layer composed mainly of diatomaceous earth fine powder with a median particle size of 10.9 μm was formed.

Next, when the remaining portion of the turbid liquid (containing scum-like white crystals) and filtrate collected during filter layer formation were poured onto the filter layer again, and nitrogen pressure of 0.2 MPa was applied from the upper portion after covering the filter with a lid, surprisingly, the whole amount of the filtrate was a light yellowish-brown transparent uniform liquid, and the weight was 271 g.

The filtrate was placed in a clean flask and toluene was removed in nitrogen gas stream under reduced pressure at 60 to 100° C., thereby liquid high purity sugar derivative-modified silicone No. 1 was obtained as a light yellowish-brown fairly-transparent to semi-transparent uniform viscous liquid. The liquid high purity sugar derivative-modified silicone No. 1 is represented by the average composition formula: $MD_{47.5}D^{R*11}{}_{7.5}D^{R*21}{}_{2}D^{R*32}{}_{1}M$. (collected amount of 137 g) In the formula, $R^{*11}$, $R^{*21}$, and $R^{*32}$ are as described above.

Example 2

Preparation of Liquid High Purity Sugar Derivative-modified Silicone No. 2

When 60.2 g of the dark yellow to orange tan opaque rubber-like soft solid at room temperature obtained in Production Example 2 (composition including sugar derivative-modified silicone No. 2 as the main component), 101 g of n-heptane, and 1.8 g of trehalose dihydrate (crystalline powder, white) were prepared in the reaction vessel, and the mixture was heated to 65 to 85° C. and stirred for 100 minutes, the white powder was in a state of being dispersed in a high viscosity orange turbid liquid. (Almost no change was observed in the powder size.) When 108 g of toluene was mixed and diluted, and allowed to cool to room temperature, the mixture was an orange yellow turbid liquid.

In the same manner as the case of Example 1, the pressure filter, plate, filter paper, and receiver were set.

100 g of the turbid liquid obtained by the treatment described above was collected in a cup, thereto was added 5.3 g of diatomaceous earth fine powder with a median particle size of 10.9 μm, and the mixture was stirred well and mixed with a spatula to form a slurry. The slurry was poured onto the filter paper set in the pressure filter, then nitrogen pressure of 0.28 MPa was applied from an upper portion after covering the filter with a lid. As a result, a filter layer composed mainly of diatomaceous earth fine powder with a median particle size of 10.9 μm was formed.

Next, when the remaining portion of the turbid liquid (containing white powder) and filtrate collected during filter layer formation were poured onto the filter layer again, and nitrogen pressure of 0.28 MPa was applied from the upper portion after covering the filter with a lid, surprisingly, the whole amount of the filtrate was a yellow orange transparent uniform liquid, and the weight was 242 g.

The filtrate was placed in a clean flask and the diluent was removed in nitrogen gas stream under reduced pressure at 80 to 105° C., thereby high purity sugar derivative-modified silicone No. 2 was obtained as a dark orange red transparent uniform viscous liquid. The high purity sugar derivative-modified silicone No. 2 was liquid at 100° C. and represented by average composition formula $MD_{74}D^{R*22}{}_2M$. (collected amount of 55 g) This substance was a soft solid at room temperature, but surprisingly, the appearance of the dark orange red transparent uniform did not change. In the formula, $R^{*22}$ is as follows.

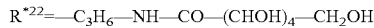

$R^{*22}$=—$C_3H_6$—NH—CO—(CHOH)$_4$—$CH_2OH$

Example 3

Preparation of Liquid High Purity Sugar Derivative-modified Silicone No. 3

When 150 g of the dark ivory color opaque viscous liquid obtained in Production Example 3 (composition including sugar derivative-modified silicone No. 3 as the main component), 151 g of toluene, and 4.5 g of polyvinyl alcohol (PVA: degree of polymerization of 1500, white particles) were prepared in the reaction vessel, and the mixture was heated to 50 to 60° C. and stirred for 55 minutes, the mixture was a dark turbid liquid. When stirring was stopped and the mixture was cooled to room temperature, a white precipitate was observed at the bottom of the white turbid liquid.

In the same manner as the case of Example 1, the pressure filter, plate, filter paper, and receiver were set.

100 g of the turbid liquid obtained by the treatment described above was collected in a cup, thereto was added 5 g of diatomaceous earth fine powder with a median particle size of 10.9 μm, and the mixture was stirred well and mixed with a spatula to form a slurry. The slurry was poured onto the filter paper set in the pressure filter, then nitrogen pressure of 0.28 MPa was applied from an upper portion after covering the filter with a lid. As a result, a filter layer composed mainly of diatomaceous earth fine powder with a median particle size of 10.9 μm was formed.

Next, when the remaining portion of the turbid liquid (containing white precipitate) and filtrate collected during filter layer formation were poured onto the filter layer again, and nitrogen pressure of 0.28 MPa was applied from the upper portion after covering the filter with a lid, surprisingly, the whole amount of the obtained filtrate was a light yellow transparent uniform liquid.

The filtrate was placed in a clean flask and toluene was removed in nitrogen gas stream under reduced pressure at 60 to 105° C., thereby liquid high purity sugar derivative-modified silicone No. 3 was obtained as a light yellow color substantially transparent uniform viscous liquid. The liquid high purity sugar derivative-modified silicone No. 3 is represented by average composition formula: $MD_{45}D^{R*12}{}_{10}D^{R*21}{}_2D^{R*32}{}_1M$. (collected amount of 132 g) In the formula, $R^{*12}$, $R^{*21}$, and $R^{*32}$ are as follows.

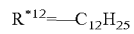

$R^{*12}$=—$C_{12}H_{25}$

$R^{*21}$=xylitol residue

$R^{*32}$=—$C_2H_4Si(OSiMe_3)_3$

Example 3-2

Preparation of Liquid High Purity Sugar Derivative-modified Silicone No. 3

When 150 g of the dark ivory color opaque viscous liquid obtained in Production Example 3 (composition including sugar derivative-modified silicone No. 3 as the main component), 150 g of toluene, and 4.5 g of malonic acid (white particles) were prepared in the reaction vessel, and the mixture was heated to 45 to 60° C. and stirred for 90 minutes, the mixture was a dark turbid uniform liquid. The size of dispersed white crystals was observed to be slightly larger than initially. Stirring was stopped and the mixture was cooled to room temperature.

In the same manner as the case of Example 1, the pressure filter, plate, filter paper, and receiver were set.

100 g of the turbid liquid obtained by the treatment described above was collected in a cup, thereto was added 5 g of diatomaceous earth fine powder with a median particle size of 10.9 μm, and the mixture was stirred well and mixed with a spatula to form a slurry. The slurry was poured onto the filter paper set in the pressure filter, then nitrogen pressure of 0.28 MPa was applied from an upper portion after covering the filter with a lid. As a result, a filter layer composed mainly of diatomaceous earth fine powder with an average diameter of 4 μm was formed.

Next, when the remaining portion of the turbid liquid (containing white crystals) and filtrate collected during filter layer formation were poured onto the filter layer again, and nitrogen pressure of 0.28 to 0.5 MPa was applied from the upper portion after covering the filter with a lid, surprisingly, the whole amount of the obtained filtrate was a light yellow transparent uniform liquid, and the weight was 268 g.

The filtrate was placed in a clean flask and toluene was removed in nitrogen gas stream under reduced pressure at 80 to 100° C., thereby liquid high purity sugar derivative-modified silicone No. 3 was obtained as a light yellow translucent uniform extremely viscous liquid. The liquid high purity sugar derivative-modified silicone No. 3 is represented by the average composition formula: $MD_{45}D^{R*12}{}_{10}D^{R*21}{}_2D^{R*32}{}_1M$. (collected amount of 134 g) In the formula, $R^{*12}$, $R^{*21}$, and $R^{*32}$ are as described above.

Example 3-3

Preparation of Liquid High Purity Sugar Derivative-modified Silicone No. 3

130 g of the dark ivory color opaque viscous liquid obtained in Production Example 3 (composition including sugar derivative-modified silicone No. 3 as the main component), 132 g of isododecane, and 3.9 g of carboxyvinyl polymer (also known as: carbomer, white fine powder) were prepared in the reaction vessel, and the mixture was heated to 60 to 80° C. and stirred and mixed for 50 minutes. When stirring was stopped and the mixture was cooled to room temperature, emulsion viscous liquid and white precipitate were generated.

An edge of ADVANTEC No. 424 filter paper (retained particle diameter 4 μm) with diameter of 95 mm (slightly larger than the inner diameter of the pressure filter) was folded evenly on a plate of the small pressure filter, and was tightly spread, then the filter was set at a base. At this time, the filter stands vertically, a receiver was installed below a filtrate outlet having a narrow diameter below the position of the plate.

3 g of diatomaceous earth fine powder with a median particle size of 10.9 μm was added to emulsion obtained by the treatment described above, and was stirred well and mixed with a spatula to form a slurry. The slurry was poured onto the filter paper set in the pressure filter, then nitrogen pressure of 0.6 MPa was applied from an upper portion after covering the filter with a lid. As a result, a filter layer composed mainly of diatomaceous earth fine powder with a median particle size of 10.9 μm was formed.

Next, when the remaining portion of the emulsion (containing white precipitate) and filtrate collected during filter layer formation were poured onto the filter layer again, and nitrogen pressure of 0.6 MPa was applied from the upper portion after covering the filter with a lid, surprisingly, the whole amount of the obtained filtrate was a pale yellow substantially transparent uniform liquid, and the weight was 232 g. Accordingly, it was considered that there was a Composition Comprising the Liquid High purity sugar derivative-modified silicone No. 3 represented by average composition formula: $MD_{45}D^{R*12}{}_{10}D^{R*21}{}_{2}D^{R*32}{}_{1}M$ and isododecane (diluent). Here, the wt. (mass) ratio of the above-described silicone No. 3 to the diluent was 1:1. In the formula, $R^{*12}$, $R^{*21}$, and $R^{*32}$ are as described above.

Example 4

Preparation of Liquid High Purity Sugar Derivative-modified Silicone No. 4

When 150 g of the dark ivory color to skin color opaque viscous liquid obtained in Production Example 4 (composition including sugar derivative-modified silicone No. 4 as the main component), 152 g of toluene, and 4.5 g of citric acid 3 Na (colorless particles) were prepared in the reaction vessel, and the mixture was heated to 45 to 60° C. and stirred for 40 minutes, the mixture was a gray tan turbid liquid. Stirring was stopped and the mixture was cooled to room temperature.

In the same manner as the case of Example 1, the pressure filter, plate, filter paper, and receiver were set.

100 g of the turbid liquid obtained by the treatment described above was collected in a cup, thereto was added 5 g of diatomaceous earth fine powder with a median particle size of 10.9 μm, and the mixture was stirred well and mixed with a spatula to form a slurry. The slurry was poured onto the filter paper set in the pressure filter, then nitrogen pressure of 0.28 MPa was applied from an upper portion after covering the filter with a lid. As a result, a filter layer composed mainly of diatomaceous earth fine powder with a median particle size of 10.9 μm was formed.

Next, when the remaining portion of the turbid liquid (containing granular crystals) and filtrate collected during filter layer formation were poured onto the filter layer again, and nitrogen pressure of 0.28 MPa was applied from the upper portion after covering the filter with a lid, surprisingly, the whole amount of the obtained filtrate was a light yellowish-brown transparent uniform liquid.

The filtrate was placed in a clean flask and toluene was removed in nitrogen gas stream under reduced pressure at 75 to 100° C., thereby liquid high purity sugar derivative-modified silicone No. 4 was obtained as a tan substantially transparent uniform viscous liquid. The liquid high purity sugar derivative-modified silicone No. 4 is represented by the average composition formula: $MD_{37}D^{R*12}{}_{10}D^{R*21}{}_{2}D^{R*32}{}_{1}M$. (collected amount of 134 g) In the formula, $R^{*12}$, $R^{*21}$, and $R^{*32}$ are as follows.

$$R^{*12}=-C_{12}H_{25}$$

$$R^{*21}=\text{xylitol residue}$$

$$R^{*32}=-C_2H_4Si(OSiMe_3)_3$$

Example 4-2

Preparation of Liquid High Purity Sugar Derivative-modified Silicone No. 4

When 150 g of the dark ivory color to skin color opaque viscous liquid obtained in Production Example 4 (composition including sugar derivative-modified silicone No. 4 as the main component), 156 g of toluene, and 4.5 g of glycine (white powdered crystal) were prepared in the reaction vessel, and the mixture was heated to 45 to 60° C. and stirred for 55 minutes, the mixture was a gray tan turbid liquid. Stirring was stopped and the mixture was cooled to room temperature.

In the same manner as the case of Example 1, the pressure filter, plate, filter paper, and receiver were set.

100 g of the turbid liquid obtained by the treatment described above was collected in a cup, thereto was added 5 g of diatomaceous earth fine powder with a median particle size of 10.9 μm, and the mixture was stirred well and mixed with a spatula to form a slurry. The slurry was poured onto the filter paper set in the pressure filter, then nitrogen pressure of 0.28 MPa was applied from an upper portion after covering the filter with a lid. As a result, a filter layer composed mainly of diatomaceous earth fine powder with a median particle size of 10.9 μm was formed.

Next, when the remaining portion of the turbid liquid (containing white powder) and filtrate collected during filter layer formation were poured onto the filter layer again, and nitrogen pressure of 0.28 MPa was applied from the upper portion after covering the filter with a lid, surprisingly, the whole amount of the obtained filtrate was a light yellow transparent uniform liquid.

The filtrate was placed in a clean flask and toluene was removed in nitrogen gas stream under reduced pressure at 80 to 100° C., thereby liquid high purity sugar derivative-modified silicone No. 4 was obtained as a light yellowish-brown fairly transparent uniform viscous liquid. The liquid high purity sugar derivative-modified silicone No. 4 is represented by the average composition formula: $MD_{37}D^{R*12}{}_{10}D^{R*21}{}_{2}D^{R*32}{}_{1}M$. (collected amount of 135 g) In the formula, $R*12$, $R*21$, and $R^{*32}$ are as described above.

Example 4-3

Preparation of Liquid High Purity Sugar Derivative-modified Silicone No. 4

When 120 g of the dark ivory color to skin color opaque viscous liquid obtained in Production Example 4 (composition including sugar derivative-modified silicone No. 4 as the main component), 120 g of toluene, and 3.6 g of anhydrous sodium sulfate (white powdered crystal) were prepared in the reaction vessel, and the mixture was heated to 55 to 70° C. and stirred and mixed for 50 minutes, the mixture was a gray tan turbid liquid. Stirring was stopped and the mixture was cooled to room temperature.

In the same manner as the case of Example 1, the pressure filter, plate, filter paper, and receiver were set.

100 g of the turbid liquid obtained by the treatment described above was collected in a cup, thereto was added 5.3 g of diatomaceous earth powder with a median particle size of 30.6 μm, and the mixture was stirred well and mixed with a spatula to form a slurry. The slurry was poured onto the filter paper set in the pressure filter, then nitrogen pressure of 0.06 MPa was applied from an upper portion after covering the filter with a lid. As a result, a filter layer composed mainly of diatomaceous earth powder with a median particle size of 30.6 μm was formed.

Next, when the remaining portion of the turbid liquid (containing white powder) and filtrate collected during filter layer formation were poured onto the filter layer again, and nitrogen pressure of 0.06 MPa was applied from the upper portion after covering the filter with a lid, surprisingly, the whole amount of the obtained filtrate was a light yellowish-brown translucent uniform liquid.

The filtrate was placed in a clean flask and toluene was removed in nitrogen gas stream under reduced pressure at 80 to 100° C., thereby 108 g of the translucent uniform viscous liquid was obtained. That is, transparency of the opaque composition containing sugar derivative-modified silicone No. 4 as the main component was clearly improved by a method of passing through the filtration layer comprising diatomaceous earth powder with median particle size of 30.6 μm, but it was found that haze is still great in comparison to the resultant obtained in Example 4 and Example 4-2.

3 g of diatomaceous earth fine powder with a median particle size of 10.9 μm was added to the translucent viscous liquid obtained above, and was stirred well and mixed with a spatula to form a slurry. The slurry was poured onto the filter paper set in another clean pressure filter, then nitrogen pressure of 0.7 MPa was applied from an upper portion after covering the filter with a lid and allowed to stand in a constant temperature bath of 50° C. As a result, a filter layer composed mainly of diatomaceous earth fine powder with a median particle size of 10.9 μm was formed. Next, the filtrate collected during filter layer formation were poured onto the filter layer again, and nitrogen pressure of 0.7 MPa was applied from the upper portion after covering the filter with a lid, and allowed to stand in a constant temperature bath of 60° C., thereby liquid high purity sugar derivative-modified silicone No. 4 was obtained as a tan substantially transparent uniform viscous liquid. The liquid high purity sugar derivative-modified silicone No. 4 is represented by average composition formula: $MD_{37}D^{R*12}{}_{10}D^{R*21}{}_{2}D^{R*32}{}_{1}M$. (collected amount of 83 g) In the formula, $R^{*12}$, $R^{*21}$, and $R^{*32}$ are as described above.

Example 5

Preparation of Composition Including Liquid High Purity Sugar Derivative-modified Silicone No. 5

When 100 g of the uniform viscous liquid that is somewhat brown-tinted in an ash-white color obtained in Production Example 5 (composition including sugar derivative-modified silicone No. 5 as the main component and composition comprising dimethylpolysiloxane (2 cst, 25° C.; diluent)), 101 g of n-heptane, and 3 g of guanine (pale yellow white powder) were prepared in the reaction vessel, and the mixture was heated to 45 to 60° C. and stirred and mixed for 50 minutes, the mixture was a turbid liquid. Stirring was stopped and the mixture was cooled to room temperature.

In the same manner as the case of Example 1, the pressure filter, plate, filter paper, and receiver were set.

100 g of the turbid liquid obtained by the treatment described above was collected in a cup, thereto was added 5 g of diatomaceous earth fine powder with a median particle size of 10.9 μm, and the mixture was stirred well and mixed with a spatula to form a slurry. The slurry was poured onto the filter paper set in the pressure filter, then nitrogen pressure of 0.28 MPa was applied from an upper portion after covering the filter with a lid. As a result, a filter layer composed mainly of diatomaceous earth fine powder with a median particle size of 10.9 μm was formed.

Next, when the remaining portion of the turbid liquid (containing pale yellow white powder) and filtrate collected during filter layer formation were poured onto the filter layer again, and nitrogen pressure of 0.28 to 0.7 MPa was applied from the upper portion after covering the filter with a lid, surprisingly, the whole amount of the obtained filtrate was a light yellow substantially transparent uniform liquid.

The filtrate was placed in a clean flask and toluene was removed in nitrogen gas stream under reduced pressure at 75 to 105° C., thereby a composition comprising liquid high purity sugar derivative-modified silicone No. 5 and dimethylpolysiloxane (2 cst, 25° C.; diluent) was obtained as a light yellow substantially transparent uniform viscous liquid. The liquid high purity sugar derivative-modified silicone No. 5 is represented by average composition formula $M^{R*21}D_{400}M^{R*21}$. (collected amount of 85 g) Here, the wt. (mass) ratio of modified silicone No. 5 to the diluent was 1:1, and in the formula, $R^{*21}$ was as follows.

$R^{*21}$=xylitol residue

Example 6

Preparation of Composition Including Liquid High Purity Sugar Derivative-modified Silicone No. 6

When 100 g of the dark brown to gray-brown opaque viscous liquid obtained in Production Example 6 (composition including sugar derivative-modified silicone No. 6 as the main component), 101 g of n-heptane, and 3 g of gallic acid (pale yellow white powder to needle crystal) were prepared in the reaction vessel, and the mixture was heated to 45 to 60° C. and stirred and mixed for 55 minutes, the mixture was a ash-white tan turbid liquid. Stirring was stopped and the mixture was cooled to room temperature.

In the same manner as the case of Example 1, the pressure filter, plate, filter paper, and receiver were set.

100 g of the turbid liquid obtained by the treatment described above was collected in a cup, thereto was added 3.2 g of diatomaceous earth fine powder with a median particle size of 10.9 μm, and the mixture was stirred well and mixed with a spatula to form a slurry. The slurry was poured onto the filter paper set in the pressure filter, then nitrogen pressure of 0.05 MPa was applied from an upper portion after covering the filter with a lid. As a result, a filter layer composed mainly of diatomaceous earth fine powder with a median particle size of 10.9 μm was formed.

Next, when the remaining portion of the turbid liquid (containing pale yellow white powder) and filtrate collected during filter layer formation were poured onto the filter layer again, and nitrogen pressure of 0.05 MPa was applied from the upper portion after covering the filter with a lid, surprisingly, the whole amount of the obtained filtrate was a light yellow substantially transparent uniform liquid. Accordingly, this composition was considered comprising liquid high purity sugar derivative-modified silicone No. 6 represented by average composition formula: $MD_{74}D^{R*21}{}_{1}M$ and n-heptane (diluent). The wt. (mass) ratio of the modified silicone No. 6 to the diluent was 1:1, and in the formula, $R^{*21}$ is as follows.

$R^{*21}$=xylitol residue

Example 7

Preparation of Composition Including Liquid High Purity Sugar Derivative-modified Silicone No. 7

120 g of the ivory color opaque liquid obtained in Production Example 7 (composition including sugar derivative-modified silicone No. 7 as the main component, and composition comprising caprylyl methicone (diluent)) and 1.8 g of aspartame (white fine powder) was placed in a 200 ml glass bottle, and the mixture was stirred well and mixed with a spatula to form a uniform turbid liquid. The mixture was allowed to stand in a thermostatic chamber at 50° C. overnight in the glass bottle with a lid, then was taken out and cooled to room temperature.

In the same manner as the case of Example 3-3, the pressure filter, plate, filter paper, and receiver were set.

3 g of diatomaceous earth fine powder with a median particle size of 10.9 μm was added to turbid liquid obtained by the treatment described above, and was stirred well and mixed with a spatula to form a slurry. The slurry was poured onto the filter paper set in the pressure filter, then nitrogen pressure of 0.3 MPa was applied from an upper portion after covering the filter with a lid. As a result, a filter layer composed of diatomaceous earth fine powder with a median particle size of 10.9 μm and aspartame was formed.

Next, when filtrate collected during filter layer formation were poured onto the filter layer again, and nitrogen pressure of 0.3 MPa was applied from the upper portion after covering the filter with a lid, surprisingly, the whole amount of the obtained filtrate was a pale yellow transparent uniform liquid, and the weight was 105 g. Accordingly, this composition was considered comprising liquid high purity sugar derivative-modified silicone No. 7 (diluent) represented below in the average structural formula (schematic diagram) and caprylyl methicone. Here, the wt. (mass) ratio of the above-described silicone No. 7 to the diluent was 1:1.

[Chemical Formula 41]

(In the formula, Me=methyl group, within [ ]n, Z=—CH$_2$CH$_2$—, outside of " " n, Z=—C$_3$H$_6$—COO—C$_3$H$_6$—, R=—C$_{16}$H$_{33}$, Y=—(CH$_2$)$_6$—, a=42.9, b=1.1, c=1.3, d=0.3, e=4.0, m=3, and n=3)

Example 8

Preparation of Liquid High Purity Sugar Derivative-modified Silicone No. 8

180 g of the gray black opaque viscous liquid obtained in Production Example 8 (composition including sugar derivative-modified silicone No. 8 as the main component), and 5.4 g of carboxyvinyl polymer (also known as: carbomer, white fine powder) were prepared in the reaction vessel, and the mixture was heated to 65 to 85° C. and stirred and mixed for 2 hours. After that, when the mixture was cooled while stirring and allowed to stand at room temperature, emulsion viscous liquid and white precipitate were generated.

Glass fiber filter paper GC-90 (retained particle diameter 0.5 μm) with diameter of 90 mm was set in stainless steel holder with tank ADVANTEC KST-90, and a tank unit and a base plate (O-ring, filter paper, part placing a support screen) were fastened by a dedicated bolt, washer, and nut and fixed such that there was no leakage. Thereby, there was a structure in which the entire edge of the filter paper was fastened vertically and leakage was prevented.

The turbid liquid (containing white precipitate) obtained by the treatment described above was introduced from an opening at an upper part of the tank, the opening was closed by a tank cap, and filtration was performed by applying nitrogen pressure of 0.4 MPa. A tan translucent filtrate that was different from the case of Comparative Example 8-2 was obtained, but when there was 5 g of filtrate, clogging occurred and dropping of the filtrate was stopped. This phenomenon was attributed to the fact that the hydrophilic impurities of a liquid that is a turbid component was solidified by solid particles (here, carbomer powder) capable of capturing the hydrophilic impurities according to the present invention and solidified. As a result, it was found that the mixture was densely accumulated on the filter and clogging occurred. The liquid of the separated main component had a translucent appearance with turbidity substantially reduced from the initial turbidity. Accordingly, it was considered that an operating principle of the present invention was proven. In contrast to this, in Comparative Example 8-2, filtration was carried out under the completely same conditions as Example 8 except that the treatment by solid particles capable of capturing hydrophilic impurities in the present invention was not performed, but the turbidity was not reduced at all prior to and after the filtration. This indicates that the turbid component passed through the filter pores (less than 0.5 μm) without causing clogging at all, and the turbid component within the composition was present as the liquid, or extremely fine particles (which may be solid or liquid) that cannot be removed by a common filter.

Example 8-2

Preparation of Liquid High Purity Sugar Derivative-modified Silicone No. 8

180 g of the gray black opaque viscous liquid obtained in Production Example 8 (composition including sugar derivative-modified silicone No. 8 as the main component), and 5.4 g of carboxyvinyl polymer (also known as: carbomer, white fine powder) were prepared in the reaction vessel, and the mixture was heated to 65 to 85° C. and stirred and mixed for 2 hours. After that, when the mixture was cooled while stirring and allowed to stand at room temperature, emulsion viscous liquid and white precipitate were generated.

In the same manner as the case of Example 8, glass fiber filter paper GC-90 (retained particle diameter 0.5 μm) with diameter of 90 mm was set in stainless steel holder with tank ADVANTEC KST-90, and a tank unit and a base plate (O-ring, filter paper, part placing a support screen) were fastened by a dedicated bolt, washer, and nut and fixed such that there was no leakage.

7 g of diatomaceous earth powder with a median particle size of 46.5 μm was added to the turbid liquid (containing white precipitate) obtained in the treatment with the object of suppressing clogging during filtration, and was stirred well and mixed with a spatula to form a slurry.

The slurry was introduced from an opening at an upper part of the tank, the opening was closed by a tank cap, and filtration was performed by applying nitrogen pressure of 0.4 MPa. As a result, 147 g of a dark brown translucent uniform viscous liquid was obtained.

The details of "sugar derivative-modified silicones No. 1 to 4 and No. 8" which are the liquid high purity sugar derivative-modified silicone according to the present invention, "composition including sugar derivative-modified silicones No. 3 and No. 5 to 7" which are compositions containing the liquid high purity sugar derivative-modified silicone according to the present invention, and "comparative compositions RE-1 to RE-8 containing sugar derivative-modified silicones No. 1 to 8" according to the Comparative Examples prepared by the methods described above are shown in the following Table 2 (2A and 2B).

TABLE 2A

| No. | Test example number Treatment agent | Appearance (transparency) | Dilute oil agent | Chemical structure of main component*[1] |
|---|---|---|---|---|
| 1 | Example 1 Diatomaceous earth | Translucent | None | MD$_{47.5}$D$^{R*11}_{7.5}$D$^{R*21}_{2}$D$^{R*32}_{1}$M |
|  | Example 1-2 Trehalose Diatomaceous earth | Fairly transparent to translucent |  |  |
| RE-1 | Comparative Example 1 | Opaque (Strong turbidity) | None |  |
|  | Comparative Example 1-2 Trehalose aqueous solution Diatomaceous earth | Opaque (Intense turbidity) |  |  |

TABLE 2A-continued

| No. | Test example number Treatment agent | Appearance (transparency) | Dilute oil agent | Chemical structure of main component*[1) |
|---|---|---|---|---|
| 2 | Example 2 Trehalose Diatomaceous earth | Transparent | None | $MD_{74}D^{R*22}{}_2M$ |
| RE-2 | Comparative Example 2 | Opaque (Strong turbidity) | None | |
| 3 | Example 3 PVA Diatomaceous earth | Substantially transparent | None | $MD_{45}D^{R*12}{}_{10}D^{R*21}{}_2D^{R*32}{}_1M$ |
| | Example 3-2 Malonic acid Diatomaceous earth | Translucent | | |
| | Example 3-3 Carbomer Diatomaceous earth | Substantially transparent | Isododecane | |
| RE-3 | Comparative Example 3 | Opaque (Strong turbidity) | None | |
| 4 | Example 4 Citric acid 3Na Diatomaceous earth | Substantially transparent | None | $MD_{37}D^{R*12}{}_{10}D^{R*21}{}_2D^{R*32}{}_1M$ |
| | Example 4-2 Glycine Diatomaceous earth | Fairly transparent | | |
| | Example 4-3 $Na_2SO_4$ Diatomaceous earth | Substantially transparent | | |
| RE-4 | Comparative Example 4 | Opaque (Strong turbidity) | None | |
| 5 | Example 5 Guanine Diatomaceous earth | Substantially transparent | 2 cs* | $M^{R*21}D_{400}M^{R*21}$ |
| RE-5 | Comparative Example 5 | Opaque (great turbidity) | 2 cs* | |

Note
*[1)The chemical structure of the sugar derivative-modified silicone serving as the main component is represented by the average composition formula.
*2 cs: Dimethylpolysiloxane (2 cst, 25° C.)

TABLE 2B

| No. | Test example number Treatment agent | Appearance (transparency) | Dilute oil agent | Chemical structure of main component*[1) |
|---|---|---|---|---|
| 6 | Example 6 Gallic acid Diatomaceous earth | Substantially transparent | n-heptane | $MD_{74}D^{R*21}{}_1M$ |
| RE-6 | Comparative Example 6 | Opaque (Strong turbidity) | n-heptane | |
| 7 | Example 7 Aspartame Diatomaceous earth | Transparent | FZ-3196* | $MD_{42.9}D^{R*31}{}_{0.3}D^{R*21}{}_{1.1}D^{R*11}{}_{4.0}D^H{}_{1.3}M$ is crosslinked with 1,5-hexadiene |
| RE-7 | Comparative Example 7 | Opaque (great turbidity) | FZ-3196* | |
| 8 | Example 8 Carbomer | Translucent | None | $MD_{44.7}D^{R*21}{}_1D^{R*13}{}_1M$ |
| | Example 8-2 Carbomer | Translucent | | |

TABLE 2B-continued

| No. | Test example number Treatment agent | Appearance (transparency) | Dilute oil agent | Chemical structure of main component*[1] |
|---|---|---|---|---|
| RE-8 | Comparative Example 8 | Opaque (Strong turbidity) | None | |
| | Comparative Example 8-2 | Opaque (Strong turbidity) | | |

Note
*[1] The chemical structure of the sugar derivative-modified silicone serving as the main component is represented by the average composition formula.
*FZ-3196: caprylyl methicone (manufactured by Dow Corning Toray Co., Ltd.)

In the tables, the structures and types of the functional groups are as follows. Siloxane Dendron Structure Group: $R^{*3}$

[Chemical Formula 42]

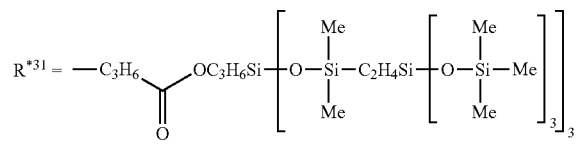

$R^{*32}=C_2H_4Si(OSiMe_3)_3$

Sugar Derivative Group: $R^{*2}$ $R^{*21}$=xylitol residue $R^{*22}=C_3H_6-NH-CO-(CHOH)_4-CH_2OH$ Other Organic Groups: $R^{*1}$ $R^{*11}=C_{16}H_{33}$ $R^{*12}=C_{12}H_{25}$ $R^{*13}=C_8H_{17}$ Light Transmittance Measurement Light transmittance T % (wavelength 750 nm, and cell thickness 10 mm) at 20 to 25° C. was measured concerning samples of Example 1, Example 1-2, Example 3, Example 3-3, Example 4, Example 5, Example 7, Example 8-2, and Comparative Example 1, Comparative Example 3, Comparative Example 4, Comparative Example 5, Comparative Example 7, and Comparative Example 8-2. The results are shown in Table 3.

TABLE 3

| Test example | Treatment agent | Appearance (color tone and transparency) | Light transmittance T % |
|---|---|---|---|
| Example 1 | Diatomaceous earth | Light yellow color translucent uniform | 70 |
| Example 1-2 | Trehalose Diatomaceous earth | Light yellowish-brown fairly transparent to translucent uniform | 81.3 |
| Comparative Example 1 | None (filtration by filter paper) | Dark ivory color opaque (strong turbidity) | 0.04 |
| Comparative Example 1-2 | Trehalose aqueous solution Diatomaceous earth | Opaque with strong white turbid | 0.01 |
| Example 3 | PVA Diatomaceous earth | Light yellow color substantially transparent uniform | 90 |
| Example 3-3 | Carbomer Diatomaceous earth | Pale yellow substantially transparent uniform | 96.1 |
| Comparative Example 3 | None (filtration by filter paper) | Dark ivory color opaque (strong turbidity) | 0.05 |
| Example 4 | Citric acid 3Na Diatomaceous earth | Tan substantially transparent uniform | 85.8 |
| Comparative Example 4 | None (filtration by filter paper) | Dark ivory color opaque (strong turbidity) | 0.05 |
| Example 5 | Guanine Diatomaceous earth | Pale yellow substantially transparent uniform | 87.8 |
| Comparative Example 5 | None | Somewhat brown-tinted ash-white colored opaque uniform | 0.3 |
| Example 7 | Aspartame Diatomaceous earth | Pale yellow transparent uniform | 99.5 |
| Comparative Example 7 | None | Ivory color opaque (great turbidity) | 0.3 |
| Example 8-2 | Carbomer | Dark brown translucent uniform | 6.3 |
| Comparative Example 8-2 | None (filtration by filter paper) | Ash-brown opaque (strong turbidity) | 0.01 |

As above, all the samples of the Comparative Examples were opaque, because a large amount of hydrophilic impurities not compatible with the sugar derivative-modified silicone that is the main component are contained, and the strong turbidity is caused by the hydrophilic impurities. On the other hand, it was found that transparency of the appearance and uniformity are greatly improved in all samples of the Examples in which the purification-increasing treatment of the present invention was performed. This fact indicates that a large part of hydrophilic impurities causing turbidity was effectively removed by the purification-increasing treatment of the present invention. In Example 8-2, a measurement value of light transmittance was a small value despite having translucency on the appearance. This is because the composition had strong coloring (Pt catalyst derived) before the purification-increasing treatment of the present invention was performed. In addition, the increase in purification according to the present invention was accomplished by treatment using solid particles, and it is extremely difficult to increase the purity by a technique of performing treatment in which solid particles are turned into solution even if the solution was removed thereafter.

GPC Composition Distribution Measurement

Concerning the samples of Example 4 and Comparative Example 4, and the samples of Example 8-2 and Comparative Example 8-2, a hydroxyl group was capped by trimethylsilylation (TMS) in pretreatment, then GPC measurement was performed using toluene as an eluent. Thereby, an area ratio of a peak derived from the main component sugar derivative-modified silicone and a peak derived from residual hydrophilic impurities was obtained.

Referencing position determination of the peak derived from the hydrophilic impurities, GPC measurement of the xylitol monoallyl ether that is the starting material was similarly performed by similarly capping the hydroxyl group. The conditions for pretreatment and GPC measurement are shown below. The results are shown in Table 4.

Pretreatment

Approximately 0.5 g of the sample (approximately 0.1 g of xylitol monoallyl ether) was precisely weighed in a test tube and diluted with 1 mL of reagent-grade toluene.

N,O-bis (trimethylsilyl) acetamide equivalent to three times the hydroxyl group mol number contained in the sample was added and mixed by gentle shaking. At this stage, the mixed liquid had white turbidity and was nonuniform.

A cooling pipe was attached to a test tube and treatment was performed for one hour under a toluene environment. When the appearance of the reaction liquid was confirmed, the reaction liquid was changed to a mostly transparent uniform liquid.

An appropriate volume of the reaction liquid in the test tube was precisely weighed in a vial bottle, and reagent-grade toluene was added and diluted. Thereby, a sample solution for GPC measurement with sample concentration of 1 wt. % (upon calculation) was obtained.

GPC Measurement Conditions

Eluent: toluene (reagent grade)
Measured temperature: 40° C.
Detector: refractometer (peak detection at the negative side)
Flow speed: 1.0 mL/min
Calibration: implemented with standard polystyrene
Injection amount of sample solution: 15 µL (sample concentration of 1 wt. %)

Peak Area Ratio of Main Component and Hydrophilic Impurities

Samples prior to and after the purification-increasing treatment according to the present invention (Untreated: Comparative Example 4; Comparative Example 8-2; Post-treatment: Example 4; Example 8-2) were subjected to GPC measurement as described above, and a ratio of the peak area derived from residual hydrophilic impurities with respect to the peak area derived from the sugar derivative-modified silicone serving as the main component was obtained by analysis of the obtained molecular weight distribution curvature, and the result thereof is summarized in Table 4 below.

TABLE 4

| Sample | Treatment agent | Main component peak number, form | Main component peak top molecular weight | Peak area ratio (%) of hydrophilic impurities with respect to the main component |
|---|---|---|---|---|
| Example 4 (Purification-increasing treatment) | Citric acid 3Na Diatomaceous earth | One mountain-shape peak | 12,400 | 0.25 |
| Comparative Example 4 (untreated) | None | One mountain-shape peak | 12,400 | 6.9 |
| Example 8-2 (Purification-increasing treatment) | Carbomer | One mountain-shape peak | 9,470 | 3.4 |
| Comparative Example 8-2 (untreated) | None | One mountain-shape peak | 9,450 | 11.2 |

As a result of the GPC analysis above, it was found that hydrophilic impurities were certainly contained in the sample of Comparative Example 4 (according to calculation from content ratio, the impurities were at least 1.8 mass % of the main component). In addition, it was found that hydrophilic impurities were hardly contained in the sample of Example 4 obtained by applying the purification-increasing treatment of the present invention to the sample of Comparative Example 4. That is, when estimated from the peak area ratio in Table 4, it was found that the hydrophilic impurities were reduced to "1/27" of prior to treatment (untreated product) by the purification-increasing treatment of the present invention.

The sample of Comparative Example 8-2 obtained by filtering the composition obtained in Production Example 8 simply using filter paper was certainly found to greatly contain hydrophilic impurities (according to calculation from content ratio, the impurities were equivalent to 7.5 mass % of the main component). Meanwhile, the sample of Example 8-2 obtained by applying the purification-increasing treatment of the present invention to the composition obtained by Production Example 8 was found to substantially reduce the content of the hydrophilic impurities. That is, when estimated from the peak area ratio in Table 4, it was found that the hydrophilic impurities were reduced to "1/3" or less of prior to treatment (untreated product) by the purification-increasing treatment of the present invention. In this case, a reduction rate of impurities was a small number value in comparison to the case of Working Example 4, but a point of being able to lower the impurities contained in an originally large quantity at once at 5 mass % or greater is useful from the perspective of application to mass production on an industrial scale.

As above, the purification-increasing treatment of the present invention was found to have an excellent effect in a wide range for removal or reduction of hydrophilic impurities derived from sugar derivatives that are hydrophilic modifiers of various sugar derivative-modified silicone, and be able to produce high purity sugar derivative-modified silicone in which the amount of impurities was cut by nearly 70% by treatment one time. Accordingly, if the purification-increasing treatment was repeated two times, it was considered that it was possible to obtain ultra-high purity sugar derivative-modified silicone not containing the impurities.

Stability Test 1

The samples of Example 1, Example 1-2, Example 2, Example 3, Example 3-2, Example 4, Example 4-2, Example 4-3, Example 5, and Comparative Examples 1 to 5 placed in a 200 mL glass bottle were left to stand for one year at room temperature (changes from around 30° C. in the summer to around 15° C. in the winter), then change of appearance of each sample was observed. The results are shown in Table 5.

TABLE 5

| No. | Test example | Initial appearance (transparency) | Room temperature, change of appearance after one year |
|---|---|---|---|
| 1 | Example 1 | Light yellow color translucent uniform | No change |
|  | Example 1-2 | Light yellowish-brown fairly transparent to translucent uniform |  |
| RE-1 | Comparative Example 1 | Dark ivory color opaque | Generation of shade and white precipitate |
| 2 | Example 2 | Dark orange red transparent uniform | No change |
| RE-2 | Comparative Example 2 | Dark yellow to orange tan opaque | No change |
| 3 | Example 3 | Light yellow color substantially transparent uniform | No change |
|  | Example 3-2 | light yellowish-brown translucent uniform |  |
| RE-3 | Comparative Example 3 | Dark ivory color opaque | Two layer separation (Transparent phase was separated on top) |
| 4 | Example 4 | Tan substantially transparent uniform | No change |
|  | Example 4-2 | Light yellowish-brown fairly transparent uniform |  |
|  | Example 4-3 | Yellowish-brown substantially transparent uniform |  |
| RE-4 | Comparative Example 4 | Dark ivory color opaque | Two layer separation (Transparent phase was separated on top) |
| 5 | Example 5 | Pale yellow substantially transparent uniform | No change |
| RE-5 | Comparative Example 5 | Somewhat brown-tinted and ash-white colored Opaque uniform | No change |

Stability test 2

Samples of Example 1-2, Example 7, and Example 4 were placed in a thermostatic chamber at 50° C. and allowed to stand overnight in order to evaluate appearance stability (influence on transparency) with respect to more extreme temperature change. Meanwhile, the samples of Example 4, Example 5, and Example 8-2 were placed in a refrigerator at 0° C. and allowed to stand overnight. The results are shown in Table 6.

TABLE 6

| Test example | Initial appearance | 50° C. | 0° C. |
|---|---|---|---|
| Example 1-2 | Light yellowish-brown fairly transparent to translucent uniform | Maintain transparency, uniformity | No data |
| Example 7 | Pale yellow transparent uniform | Maintain transparency, uniformity | No data |
| Example 4 | Tan substantially transparent uniform | Maintain transparency, uniformity | Maintain transparency, uniformity |
| Example 5 | Pale yellow substantially transparent uniform | No data | Maintain transparency, uniformity |
| Example 8-2 | Dark brown translucent | No data | Maintain transparency, uniformity |

From the above results, it was confirmed that when compared with the samples of Comparative Examples, the samples of Examples had far higher purity in a point of less content of hydrophilic impurities, and they also had far superior in a point of homogeneity and transparency of appearance, and this superiority was unchanged at high temperature, at low temperature, or under long term storage.

The purification-increasing treatment method of the present invention is easy, low energy consumption, and highly efficient, and solved, with a new viewpoint, the dilemma of the conventional method represented by an inefficient method such as a high temperature stripping method and an irrational process such as simply repeating filtration of the liquid impurities to remove them. Accordingly, contribution to economic and social development is extremely great.

Hereinafter, Formulation Examples of the cosmetic composition and the external use preparation according to the present invention are described, but the cosmetic composition and the external use preparation according to the present invention are not limited to the types and compositions recited in these Formulation Examples.

The liquid high purity sugar derivative-modified silicone or a composition including the same according to the present invention can be used for various external use preparations and cosmetic compositions. A specific Formulation Example thereof is one in which components corresponding to "silicone compound No. 1 to 6" in Formulation Examples 1 to 62 of various cosmetic compositions and external use preparations described in Patent Document 28 (Japanese Unexamined Patent Application Publication No. 2012-246446A) are substituted with the liquid high purity sugar derivative-modified silicones No. 1 to No. 8 according to the present invention.

The high purity sugar derivative-modified silicone of the present invention has the advantage that, since a residual amount of hydrophilic modifier having extremely different polarity from the modified silicone is reduced, problems related to poor compatibility at the time of the addition of various starting materials are unlikely to occur when designing a formulation for a cosmetic composition or external use preparation, so the scope of formulation design widens. At the same time, it is also possible to reduce the risk or concerns related to the stability of the final product. Since the composition has high purity, it is advantageous from the perspectives of the tactile feel improving effect, moisturizing effect, minimal degradation phenomena such as odorization over time, surface active effect, emulsification performance, powder dispersion stability, powder surface treatment effect, or the duration of these effects, and the like in comparison to typical sugar derivative-modified silicone compositions with great impurity content. In particular, in a formulation containing a powder or a formulation containing a small amount of water, the characteristics of the high-purity sugar derivative-modified silicone obtained by the present invention make it possible to finely disperse medicinal components or powders into a cosmetic composition or external use preparation more stably than with conventional methods. As a result, a substantial advantage arises in that the effects of the original formulation are amplified, such as an improvement in evenness in application, in cosmetic composition duration or coloring or an improvement in a skin care or UV filter effect. In addition, in a formulation not containing a powder, the characteristics of the high-purity sugar derivative-modified silicone obtained by the present invention make it possible to easily obtain a stable product with excellent transparency, even if the composition has low viscosity.

The following can also be listed as Formulations Examples of the cosmetic composition and external use preparation according to the present invention. Furthermore, if all of the following polyether-modified silicone is replaced by liquid high purity sugar derivative-modified silicone of the present invention (for example, No. 1), it is also possible to design PEG-free formulations. In the list below, "parts" indicates parts by (weight) mass. In the list below, "parts" indicates parts by (weight) mass.

Formulation Example: Liquid Foundation (W/O) Mainly Based on Hydrocarbon-based Cosmetic Composition Base Materials

| (Components) | |
|---|---|
| 1. Isodecane | 20 parts |
| 2. Isohexadecane | 10 parts |
| 3. Isotridecyl isononanoate | 3 parts |
| 4. Glyceryl tricapryl-caprate | 2 parts |
| 5. Polyether-modified silicone (note 1) | 0.5 parts |
| 6. High purity sugar derivative-modified silicone No. 7 | 1.5 parts |
| 7. Organic modified clay mineral (Benton 38V) | 1.5 parts |
| 8. Octyl methoxycinnamate | 5 parts |
| 9. Octyl silane-treated titanium oxide | 8.5 parts |
| 10. Octyl silane-treated red iron oxide | 0.4 parts |
| 11. Octyl silane-treated yellow iron oxide | 1 part |
| 12. Octyl silane-treated black iron oxide | 0.1 parts |
| 13. Dimethicone, dimethicone crosspolymer (note 2) | 2 parts |
| 14. Isododecane/(acrylate/polytrimethylsiloxy methacrylate) copolymer (note 3) | 1 part |
| 15. Trimethylsiloxysilicate | 1 part |
| 16. 1,3-butylene glycol | 5 parts |
| 17. Glycerin | 3 parts |
| 18. Sodium chloride | 0.5 parts |
| 19. Preservative | as appropriate |
| 20. Purified water | remainder |
| 21. Fragrance | as appropriate |

(note 1) ES-5300, manufactured by Dow Corning Toray Co., Ltd.
(note 2) DC9045, manufactured by Dow Corning Corp.
(note 3) FA-4002ID, manufactured by Dow Corning Toray Co., Ltd.

Production Method
Step 1: Components 1, 2, 5, 6, 7, 8, 13, 14, and 15 are stirred to mix.
Step 2: Components 3, 4, and 9 to 12 are kneaded to mix with three rollers.
Step 3: The mixture of step 2 is added to the mixture obtained in step 1 while stirring, and they are further stirred to mix.
Step 4: The water phase in which components 16 to 21 were uniformly dissolved is added, by stirring, to the mixture obtained in step 3 and emulsified (use of an emulsifier), and a container is filled with the mixture to obtain a product.

The obtained W/O liquid foundation has no unpleasant odor, and when used, has excellent emulsification stability, water resistance, and cosmetic durability, and makes skin texture and wrinkles less noticeable. Despite being mainly composed of a hydrocarbon based cosmetic composition base material, the mixture has a lively feel of a smooth silicone feel and is excellent in adhesion.

Formulation Example: W/O Emulsion-type Sunscreen Emulsion

| (Component) | (wt. %) |
|---|---|
| 1. D5 (decamethylcyclopentasiloxane) | 26.6 |
| 2. Caprylyl methicone (note 4) | 5.0 |
| 3. BY 11-018 (note 5) | 5.0 |
| 4. Octyldodecyl myristate | 10.0 |
| 5. Castor oil hydrogenated triisostearic acid PEG-20 | 0.3 |
| 6. Polyether-modified silicone (note 6) | 1.2 |
| 7. High purity sugar derivative-modified silicone No. 3 according to the present invention | 0.8 |
| 8. Disteardimonium hectorite | 0.3 |
| 9. Dimethicone/methicone polymer-treated zinc oxide | 15.0 |
| 10. Aluminum stearate-treated titanium oxide | 13.0 |
| 11. Methylparaben | 0.1 |
| 12. 95% ethanol | 5.0 |
| 13. Magnesium sulfate | 0.7 |
| 14. Fragrance | as appropriate |
| 15. Purified water | 17.0 |

(note 4) FZ-3196, manufactured by Dow Corning Toray Co., Ltd.
(note 5) D5 dilution containing 30% trimethylsiloxy silicic acid, manufactured by Dow Corning Toray Co., Ltd.
(note 6) ES-5300, manufactured by Dow Corning Toray Co., Ltd.

Production Method
A: Thoroughly blend components 1 to 11 to make a uniform dispersion.
B: Blend components 12 to 15 to make a uniform solution.
C: Stir A, and gradually add B and emulsify. (Use of an emulsifier)

Effects
The sunscreen emulsion is substantially free of stickiness, and spreads very easily. A skin sensation of discomfort was slight while having extremely excellent adhesiveness, and a smooth silicone soft feeling was obtained. The emulsion has excellent stability, with minimal change in viscosity, such as increased viscosity, relative to temperature and time. Usability is excellent.

Formulation Example: Bilayered (Shake Before Use to Mix Type) Sun Cut Lotion

| (Component) | (wt. %) |
|---|---|
| 1. D5 (decamethylcyclopentasiloxane) | 23.6 |
| 2. Caprylyl methicone (note 4) | 7.5 |
| 3. DC 670 Fluid (note 7) | 5.0 |
| 4. Liquid paraffin | 3.0 |

-continued

| (Component) | (wt. %) |
|---|---|
| 5. Ethylhexyl methoxycinnamate | 7.5 |
| 6. Polyether-modified silicone (note 6) | 1.0 |
| 7. High purity sugar derivative-modified silicone No. 1 according to the present invention | 1.0 |
| 8. Organic modified bentonite (Benton 38) | 0.2 |
| 9. Methyl hydrogen polysiloxane-treated zinc oxide | 22.5 |
| 10. 95% ethanol | 5.0 |
| 11. 1,3-butylene glycol | 3.0 |
| 12. Sodium citrate | 0.2 |
| 13. Sodium chloride | 0.5 |
| 14. Fragrance | as appropriate |
| 15. Purified water | 20.0 |

(note 4) FZ-3196, manufactured by Dow Corning Toray Co., Ltd.
(note 6) ES-5300, manufactured by Dow Corning Toray Co., Ltd.
(note 7) D5 dilution containing 50% polypropyl silsesquioxane, manufactured by Dow Corning Corp.

Production Method

A: Thoroughly blend components 1 to 9 to make a uniform dispersion.

B: Blend components 10 to 15 to make a uniform solution.

C: Stir A, and gradually add B and emulsify. (Use of an emulsifier)

Effects

Has the refreshing feel of water, spreads very lightly and well. Additionally, because the zinc oxide microparticles can be stably microdispersed due to the excellent particle dispersing effect of the product of the present invention, there is the advantage of not being likely to leave a white residue on the skin after application. Furthermore, there is no discomfort, such as tense feeling, and ultraviolet protection effect is excellent.

Formulation Example: W/O Emulsion-type Sun Cut Cream

| (Component) | (wt. %) |
|---|---|
| 1. EL-8040 ID (note 8) | 5.0 |
| 2. MQ-1640 Flake Resin (note 9) | 1.0 |
| 3. High purity sugar derivative-modified silicone No. 7 according to the present invention | 1.0 |
| 4. Isotridecyl isononanate | 2.0 |
| 5. Isohexadecane | 1.7 |
| 6. Powder-in-oil dispersion (high purity sugar derivative-modified silicone No. 4 according to the present invention/D5/fine particulate titanium oxide = 3/15/12 weight ratio mixture) | 22.5 |
| 7. Powder-in-oil dispersion (high purity sugar derivative-modified silicone No. 4 according to the present invention/D5/microparticle zinc oxide = 1.5/10.5/18 weight ratio mixture) | 31.5 |
| 8. 1,3-butylene glycol | 2.0 |
| 9. Sodium chloride | 0.5 |
| 10. Purified water | 32.8 |

(note 8) Isododecane dilution containing 16% dimethicone cross-polymer, manufactured by Dow Corning Corp.
(note 9) Blend of trimethylsiloxysilicic acid and polypropyl silsesquioxane, manufactured by Dow Corning Corp.

Production Method

A: After blending components 2 to 5 to make a uniform solution, add component 1 and blend thoroughly to make a uniform dispersion.

B: Blend components 8 to 10 to make a uniform solution.

C: While stirring A, gradually add B and emulsify (by using an emulsifier), and then add components 6 and 7 and mix to obtain a homogeneous cream.

Effects

Yields a unique, velvety, thick, and smooth application feel. Excellent ultraviolet protection effect and antiperspirant effect, with a fresh feel during use that is not sticky or greasy.

Formulation Example: Polyol/O Emulsified Vitamin C Compounded Skin Care Cream

| (Component) | (wt. %) |
|---|---|
| 1. D5 (decamethylcyclopentasiloxane) | 17.9 |
| 2. Dimethicone (5 cst) | 5.0 |
| 3. High purity sugar derivative-modified silicone No. 5 according to the present invention | 4.0 |
| 4. 9040 silicone elastomer blend (note 10) | 10.0 |
| 5. Propylene glycol | 7.6 |
| 6. Glycerin | 45.0 |
| 7. Vitamin C | 10.5 |

(note 10) D5 dilution containing 12% dimethicone cross-polymer, manufactured by Dow Corning Corp.

Production Method

A: Thoroughly blend components 1 to 4 to make a uniform dispersion.

B: Mix components 5 to 7 and heat to 70° C. and stir to make a uniform solution.

C: While stirring A, gradually add B and emulsify (by using an emulsifier), and obtain a homogeneous cream.

Effects

Since a stable non-water-based emulsion was obtained, the stability of vitamin C is favorably held. As a result, it was anticipated that the inherent effect of vitamin C which is a physiologically active substance would be mild and sustained on the skin or in the skin.

Formulation Example: Polyol/O Emulsified Vitamin C Compounded Skin External Use Preparation

| (Component) | (wt. %) |
|---|---|
| 1. Caprylyl methicone (note 4) | 3.0 |
| 2. Mineral oil | 3.0 |
| 3. Glyceryl tri (caprylate/caprate) | 3.0 |
| 4. High purity sugar derivative-modified silicone No. 4 according to the present invention | 1.0 |
| 5. Polyether-modified silicone (note 6) | 1.0 |
| 6. EL-8050 ID silicone organic elastomer blend (note 11) | 8.0 |
| 7. Dipropylene glycol | 3.0 |
| 8. Glycerin | 60.0 |
| 9. Vitamin C | 15.0 |

(note 4) FZ-3196, manufactured by Dow Corning Toray Co., Ltd.
(note 6) ES-5300, manufactured by Dow Corning Toray Co., Ltd.
(note 11) Isododecane dilution containing 15% (dimethicone/bis-isobutyl PPG-20) cross-polymer, manufactured by Dow Corning Corp.

Production Method

A: Thoroughly blend components 1 to 6 to make a uniform dispersion.

B: Mix components 7 to 9 and heat to 70° C. and stir to make a uniform solution.

C: While stirring A, gradually add B and emulsify (by using an emulsifier), and obtain a homogeneous cream.

Effects

Since a stable non-water-based emulsion was obtained, the stability of vitamin C is favorably held. As a result, it was anticipated that the inherent effect of vitamin C which is a physiologically active substance would be mild and sustained on the skin or in the skin.

The invention claimed is:

1. A production method for a liquid high purity sugar derivative-modified silicone or a composition thereof, the method comprising the steps of:
   capturing hydrophilic impurities in solid particles by causing an impurity containing composition containing liquid sugar derivative-modified silicone and the hydrophilic impurities derived from a sugar derivative to contact the solid particles, the sugar derivative being a hydrophilic modifier of the sugar derivative-modified silicone, and the solid particles being able to capture the hydrophilic impurities; and separating the sugar derivative-modified silicone and the solid particles;

wherein the sugar derivative-modified silicone is a sugar derivative-modified silicone represented by the following general formula (1):

wherein, $R^1$ represents a monovalent organic group (excluding $R^2$, L, and Q), a hydrogen atom or a hydroxyl group, and $R^2$ is a substituted or unsubstituted, straight or branched monovalent hydrocarbon group having from 9 to 60 carbon atoms, or a chain organosiloxane group represented by the following general formula (2-1):

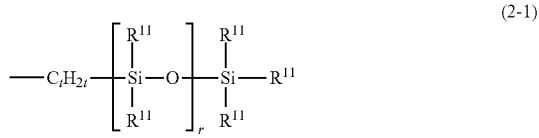

wherein, each $R^{11}$ is independently a substituted or unsubstituted monovalent hydrocarbon group having from 1 to 30 carbons, hydroxyl groups, or hydrogen atoms, and at least one of the $R^{11}$ is the monovalent hydrocarbon group; t is a number in a range of 2 to 10, and r is a number in a range of 1 to 500, or the following general formula (2-2):

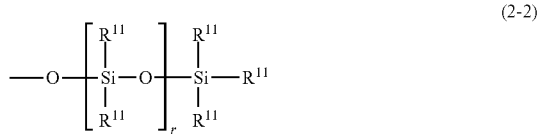

wherein, $R^{11}$ and r are as described above, and $L^1$ represents a silylalkyl group having a siloxane dendron structure and represented by the following general formula (3) when i=1:

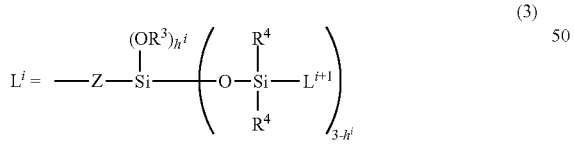

wherein, each $R^3$ independently represents a substituted or unsubstituted, straight or branched monovalent hydrocarbon group having from 1 to 30 carbons, each $R^4$ independently represents an alkyl group or phenyl group having from 1 to 6 carbons, Z represents a divalent organic group, i represents a generation of the silylalkyl group represented by $L^i$ and is an integer of 1 to k when k is a number of generations that is a number of repetitions of the silylalkyl group, the number of generations k is an integer from 1 to 10, $L^{i+1}$ is the silylalkyl group when i is less than k, and $R^4$ when i=k, and $h^i$ is a number in a range of 0 to 3, Q represents a sugar derivative group, and a, b, c, and d are numbers respectively in ranges of $1.0 \leq a \leq 2.5$, $0 \leq b \leq 1.5$, $0 \leq c \leq 1.5$, and $0.0001 \leq d \leq 1.5$.

2. The production method according to claim 1, wherein the solid particles include one or more material selected from a silicon atom-free low molecular organic compound, a silicon atom-free non-crosslinked hydrophilic high molecular organic compound, a silicon atom-free crosslinked hydrophilic high molecular organic compound, a salt, a mineral derived material, and activated carbon.

3. The production method according to claim 2, wherein the solid particles include the silicon atom-free crosslinked hydrophilic high molecular organic compound.

4. The production method according to claim 1, wherein the solid particles are porous.

5. The production method according to claim 1, wherein the solid particles include silicon dioxide.

6. The production method according to claim 1, wherein the solid particles include at least one type of hydrogen bond forming substance and/or at least one type of ionic bond forming substance and/or a hydrate thereof.

7. The production method according to claim 1, wherein the separating step includes filtering using filtration material.

8. The production method according to claim 1, wherein the impurity containing compositions are caused to come into contact with the solid particles in the capturing step after dilution using a solvent, the solvent being a good solvent for the sugar derivative-modified silicone and a poor solvent for the hydrophilic impurities.

9. The production method according to claim 8, further comprising the step(s) of:
heating and/or depressurizing the composition and removing the solvent after the separating step.

10. The production method according to claim 1, wherein the sugar derivative group is a group derived from monosaccharides, disaccharides, or oligosaccharides.

11. The production method according to claim 1, wherein the sugar derivative group is a sugar alcohol group-containing organic group.

12. The production method according to claim 1, wherein the sugar derivative-modified silicone is modified using a sugar alcohol group-containing organic group represented by the following general formula (4-1):

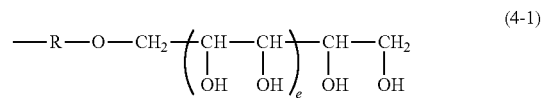

wherein, R represents a divalent organic group, and e is 1 or 2, or the following general formula (4-2):

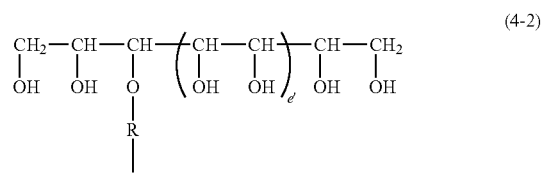

wherein, R is as described above; and e' is 0 or 1.

13. The production method according to claim 1, wherein the sugar derivative-modified silicone is a sugar derivative-modified crosslinked silicone.

* * * * *